(12) United States Patent
Hashimoto et al.

(10) Patent No.: US 8,288,016 B2
(45) Date of Patent: Oct. 16, 2012

(54) FUSED POLYCYCLIC COMPOUND AND ORGANIC LIGHT-EMITTING DEVICE USING THE COMPOUND

(75) Inventors: Masashi Hashimoto, Tokyo (JP); Satoshi Igawa, Fujisawa (JP); Naoki Yamada, Inagi (JP); Takayuki Horiuchi, Tokyo (JP); Shinjiro Okada, Kamakura (JP)

(73) Assignee: Canon Kabushiki Kaisha, Tokyo (JP)

( * ) Notice: Subject to any disclaimer, the term of this patent is extended or adjusted under 35 U.S.C. 154(b) by 147 days.

(21) Appl. No.: 13/056,351

(22) PCT Filed: Jul. 28, 2009

(86) PCT No.: PCT/JP2009/063718
§ 371 (c)(1),
(2), (4) Date: Jan. 28, 2011

(87) PCT Pub. No.: WO2010/016450
PCT Pub. Date: Feb. 11, 2010

(65) Prior Publication Data
US 2011/0127908 A1 Jun. 2, 2011

(30) Foreign Application Priority Data
Aug. 4, 2008 (JP) ................... 2008-200354

(51) Int. Cl.
*H01L 51/54* (2006.01)
*C07C 211/61* (2006.01)
*C07C 13/62* (2006.01)

(52) U.S. Cl. ........ 428/690; 428/917; 313/504; 313/506; 564/308; 585/27

(58) Field of Classification Search .................. None
See application file for complete search history.

(56) References Cited

U.S. PATENT DOCUMENTS

| | | | |
|---|---|---|---|
| 6,613,454 B2 | 9/2003 | Ara et al. | 428/690 |
| 6,815,090 B1 | 11/2004 | Tagami et al. | 428/690 |
| 6,818,327 B2 | 11/2004 | Tagami et al. | |
| 7,858,210 B2 | 12/2010 | Hashimoto et al. | |
| 2004/0214043 A1 | 10/2004 | Tagami et al. | |
| 2006/0024523 A1 | 2/2006 | Tagami et al. | |
| 2007/0003788 A1 | 1/2007 | Tagami et al. | |
| 2008/0074045 A1 | 3/2008 | Tagami et al. | |
| 2008/0224603 A1 | 9/2008 | Hashimoto et al. | |
| 2009/0121625 A1 | 5/2009 | Ohrui et al. | |
| 2009/0134788 A1 | 5/2009 | Yamada et al. | |
| 2009/0278446 A1 | 11/2009 | Igawa et al. | 313/504 |
| 2009/0278447 A1 | 11/2009 | Saitoh et al. | |
| 2009/0295279 A1 | 12/2009 | Igawa et al. | 313/504 |
| 2010/0176716 A1 | 7/2010 | Igawa et al. | |
| 2010/0327274 A1 | 12/2010 | Okajima et al. | |
| 2011/0095284 A1 | 4/2011 | Watanabe et al. | |

FOREIGN PATENT DOCUMENTS

| | | |
|---|---|---|
| JP | 10-294177 | 11/1998 |
| JP | 10-330295 | 12/1998 |
| JP | 2002-008867 | 1/2002 |
| JP | 2002-110353 | 4/2002 |
| JP | 2005-053806 | 3/2005 |
| JP | 2008-255095 | 10/2008 |
| JP | 2008-285450 | 11/2008 |
| JP | 2008-300753 | 12/2008 |
| WO | WO 01/23497 | 4/2001 |

OTHER PUBLICATIONS

Barry M. Trost, "Antiaromatic Peripheral Systems. Synthesis and Chemistry of Pyracyloquinone", J. Am. Chem. Soc. vol. 91, No. 4, pp. 918-923 (1969). Jeffrey A. Dodge, et al., "Regioselective Synthesis of Substituted Rubrenes", J. Org. Chem. No. 55, pp. 4190-4198 (1990).

*Primary Examiner* — Dawn L. Garrett
(74) *Attorney, Agent, or Firm* — Fitzpatrick, Cella, Harper & Scinto

(57) ABSTRACT

Provided is an organic light-emitting device having good durability. The organic light-emitting device includes an anode, a cathode, and organic compound layers interposed between the anode and the cathode, and at least one of the organic compound layers contains a fused polycyclic compound represented by the following general formula [1]:

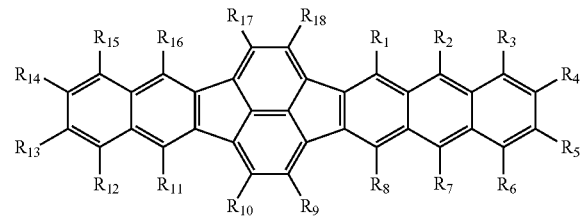

[1]

wherein $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, and $R_{18}$ each represent, independently of one another, a hydrogen atom, a halogen atom, an alkyl group having 1 to 20 carbon atoms, a substituted amino group, a substituted or unsubstituted aryl group, or a substituted or unsubstituted heterocyclic group, provided that at least one of $R_1$ to $R_{18}$ is a substituted phenyl group represented by the following general formula [2]:

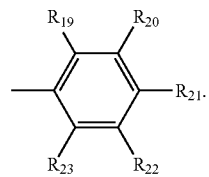

[2]

8 Claims, 3 Drawing Sheets

FORMULA [1]　　FORMULA [2]

FUSED POLYCYCLIC COMPOUND AND ORGANIC LIGHT-EMITTING DEVICE USING THE COMPOUND

TECHNICAL FIELD

The present invention relates to a fused polycyclic compound and a light-emitting device using the compound.

BACKGROUND ART

Recently, a significant progress has been made relating to an organic light-emitting device. The characteristic feature of the device includes that high luminance, a variety of emission wavelengths and a high-speed response can be obtained at a low voltage and also a thin and light-weight light-emitting device can be produced. For these reason, application of an organic light-emitting device in a broad and diverse range has been suggested.

At a practical level, however, optical output with more improved luminance or higher conversion efficiency is required. In addition, there are still a lot of problems associated with durability, for example, time-dependent change due to use for a long period of time or degradation due to atmospheric gas including oxygen, moisture or the like. Furthermore, for an application in a full-color display and the like, light emission of red, green, and blue colors with good color purity is required, but it cannot be said that such needs are completely met at the present moment.

In addition, a large number of aromatic compounds and fused ring aromatic compounds have been researched and proposed as a fluorescent organic compound to be used as a constituent material of as an electron transport layer or a light-emitting layer. However, it is hard to say that a compound capable of sufficiently satisfying emission luminance and durability has been obtained.

The case where any such aromatic compound or fused ring aromatic compound is used as a constituent material of an organic light-emitting device is described in, for example, Japanese Patent Application Laid-Open Nos. 2002-8867, H10-330295, and H10-294177. These patent documents also disclose the application of the aromatic compound or the fused ring aromatic compound to an organic light-emitting device.

DISCLOSURE OF THE INVENTION

On the other hand, the application of an organic light-emitting device to a display apparatus such as a display requires the device to have sufficiently high durability.

In view of the foregoing, an object of the present invention is to provide an organic light-emitting device having good durability. Another object of the present invention is to provide a light-emitting device that can be easily produced at a relatively low cost.

The present invention provides a fused polycyclic compound and a light-emitting device containing the compound, the fused polycyclic compound being represented by the following general formula [1]:

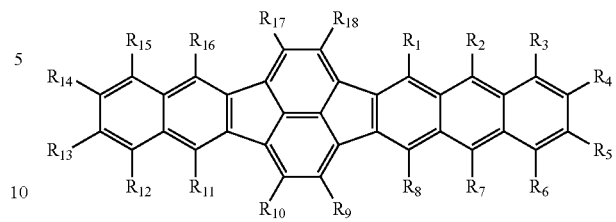

[1]

wherein $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, and $R_{18}$ each represent, independently of one another, a hydrogen atom, a halogen atom, an alkyl group having 1 to 20 carbon atoms, a substituted amino group, a substituted or unsubstituted aryl group, or a substituted or unsubstituted heterocyclic group, provided that at least one of $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, and $R_{18}$ is a substituted phenyl group represented by the following general formula [2]:

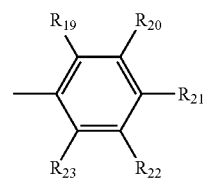

[2]

wherein $R_{19}$, $R_{20}$, $R_{21}$, $R_{22}$, and $R_{23}$ each represent, independently of one another, a hydrogen atom, a halogen atom, an alkyl group having 1 to 20 carbon atoms, a substituted amino group, a substituted or unsubstituted aryl group, or a substituted or unsubstituted heterocyclic group, provided that at least one of $R_{19}$, $R_{20}$, $R_{22}$, and $R_{23}$ is a halogen atom, an alkyl group having 1 to 20 carbon atoms, a substituted amino group, a substituted or unsubstituted aryl group, or a substituted or unsubstituted heterocyclic group.

According to the present invention, there can be provided an organic light-emitting device having good durability. In addition, the light-emitting device of the present invention is also excellent as a display device.

BEST MODE FOR CARRYING OUT THE INVENTION

Figure 1:
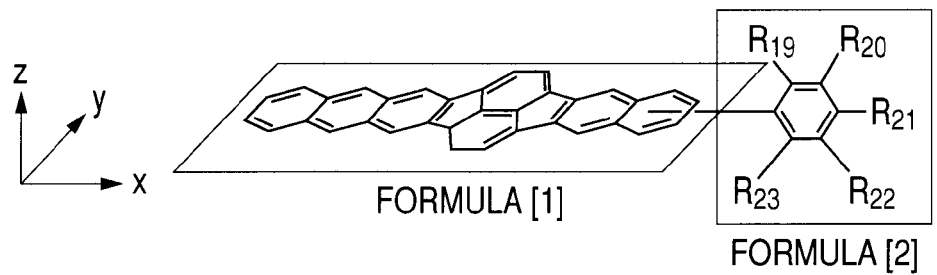
FIG. 1 is a schematic view when a fused polycyclic compound of the present invention is observed three-dimensionally.

Hereinafter, the present invention is described in detail. First, a fused polycyclic compound of the present invention is described. The fused polycyclic compound of the present invention is represented by the following general formula [1].

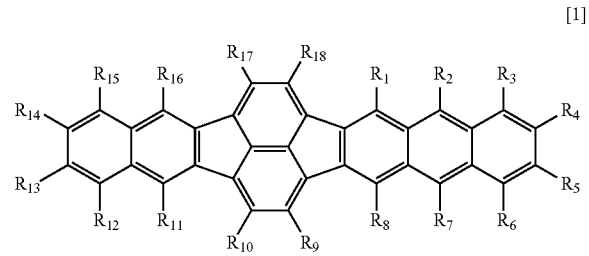

[1]

In the formula [1], $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, and $R_{18}$ each represent, independently of one another, a hydrogen atom, a halogen atom, an alkyl group having 1 to 20 carbon atoms, a substituted amino group, a substituted or unsubstituted aryl group, or a substituted or unsubstituted heterocyclic group.

Examples of the halogen atom represented by $R_1$ to $R_{18}$ preferably include a fluorine atom, a chlorine atom, and a bromine atom. When an organic light-emitting device is produced by a vacuum evaporation method, a fluorine atom is particularly preferable from the viewpoint of sublimation property.

Examples of the alkyl group having 1 to 20 carbon atoms represented by $R_1$ to $R_{18}$ include a methyl group, an ethyl group, an n-propyl group, an isopropyl group, an n-butyl group, a t-butyl group, a pentyl group, an octyl group, a dodecyl group, a cyclohexyl group, a bicyclooctyl group, and an adamantyl group. In addition, when the alkyl group has 2 or more carbon atoms, one methylene group, or two or more non-adjacent methylene groups, in the alkyl group may be substituted by —O— so that, for example, a methoxy group, an ethoxy group, an octyloxy group, a decyloxy group, or the like is formed. Furthermore, a hydrogen atom in the alkyl group may be substituted by a fluorine atom so that, for example, a trifluoromethyl group is formed. Of those alkyl groups, a methyl group, a t-butyl group, a cyclohexyl group, and a trifluoromethyl group is preferred from the viewpoints of the conductivity and sublimation property. A methyl group, a t-butyl group, and a trifluoromethyl group are more preferred, and a methyl group and a t-butyl group are still more preferred.

From the viewpoints of the conductivity and glass transition temperature, the substituted amino group represented by $R_1$ to $R_{18}$ is preferably a dimethylamino group, a diphenylamino group, or a ditolylamino group, and particularly preferably a diphenylamino group.

Examples of the aryl group represented by $R_1$ to $R_{18}$ include a phenyl group, a biphenyl group, a terphenyl group, a fluorenyl group, a naphthyl group, a fluoranthenyl group, an anthryl group, a phenanthryl group, a pyrenyl group, a tetracenyl group, a pentacenyl group, a triphenylenyl group, and a perylenyl group. With a view to the sublimation property, a phenyl group, a biphenyl group, a fluorenyl group, or a naphthyl group is preferred. A phenyl group or a biphenyl group is more preferred.

Examples of the heterocyclic group represented by $R_1$ to $R_{18}$ include a thienyl group, a pyrrolyl group, a pyridyl group, a pyrazyl group, a pyrimidyl group, a pyridazinyl group, a quinolyl group, an isoquinolyl group, a phenanthridinyl group, an acridinyl group, a naphthyridinyl group, a quinoxalinyl group, a quinazolinyl group, a cinnolinyl group, a phthalazinyl group, a phenanthrolyl group, a phenazinyl group, a dibenzofuryl group, a dibenzothiophenyl group, a carbazolyl group, a benzofuryl group, a benzothiophenyl group, an indolyl group, a cycloazyl group, a benzoimidazolyl group, a benzothiazolyl group, and a benzothiadiazolyl group. A pyridyl group is preferred from the viewpoint of the sublimation property.

A substituent which each of the above aryl group and the above heterocyclic group may further have is not particularly limited; the substituent is preferably a halogen atom, an alkyl group having 1 to 20 carbon atoms, a substituted amino group, or an aryl group. Specific examples of each of the halogen atom, the alkyl group, the substituted amino group, and the aryl group are similar to the specific examples of each of the halogen atom, the alkyl group, the substituted amino group, and the aryl group each serving as a substituent to be introduced into each of $R_1$ to $R_{16}$ described above. It should be noted that when the substituent is an alkyl group having 2 or more carbon atoms, one methylene group or two or more non-adjacent methylene groups in the alkyl group may be substituted by —O—. In addition, a hydrogen atom in the alkyl group may be substituted by a fluorine atom. Of those substituents, a fluorine atom, a trifluoromethyl group, a methyl group, an ethyl group, a t-butyl group, a methoxy group, a dimethylamino group, a di-t-butylamino group, a phenyl group, or a pyridyl group is preferred from the viewpoints of the glass transition temperature and sublimation property; a fluorine atom, a trifluoromethyl group, a methyl group, a t-butyl group, or a phenyl group is more preferred, and t-butyl group or a phenyl group is more preferred.

It should be noted that at least one of $R_1$ to $R_{18}$ is a substituted phenyl group represented by the following general formula [2].

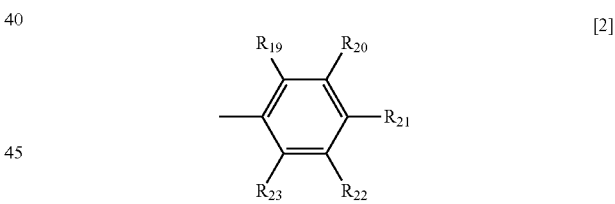

[2]

In the formula [2], $R_{19}$, $R_{20}$, $R_{21}$, $R_{22}$, and $R_{23}$ each represent, independently of one another, a hydrogen atom, a halogen atom, an alkyl group having 1 to 20 carbon atoms, a substituted amino group, a substituted or unsubstituted aryl group, or a substituted or unsubstituted heterocyclic group. Specific examples of each of the halogen atom, the alkyl group, the substituted amino group, the aryl group, and the heterocyclic group represented by each of $R_{19}$ to $R_{23}$, and the substituent which each of the aryl group and the heterocyclic group may have are similar to the specific examples of each of $R_1$ to $R_{18}$ in the formula [1]. It should be noted that at least one of $R_{19}$, $R_{20}$, $R_{22}$, and $R_{23}$ is a halogen atom, an alkyl group having 1 to 20 carbon atoms, a substituted amino group, a substituted or unsubstituted aryl group, or a substituted or unsubstituted heterocyclic group.

The fused polycyclic compound of the present invention particularly preferably has a structure where $R_1$ to $R_{18}$ in the formula [1] and $R_{19}$ to $R_{23}$ in the formula [2] each represent a hydrogen atom or a hydrocarbon group including only carbon atom(s) and hydrogen atom(s). This is because the compound having a structure where $R_1$ to $R_{18}$ and $R_{19}$ to $R_{23}$ each represent a hydrogen atom or a hydrocarbon group may additionally reduce the uptake of, for example, an ionic impurity as one possible cause for the degradation of an organic light-emitting device due to energization as compared to a compound containing a hetero atom having a lone pair of electrons. The reduction of the inclusion of an ionic impurity increases the life of the organic light-emitting device.

The fused polycyclic compound of the present invention has a structure where at least one of the substituents ($R_1$ to $R_{18}$) to be introduced into a fused polycyclic skeleton shown in the formula [1] is a substituted phenyl group where a specific substituent is introduced at a specific position shown in the formula [2].

The effects achieved by the above structure are described below.

FIG. 1 is a three-dimensional schematic view showing the fused polycyclic compound of the present invention. As illustrated in FIG. 1, the fused polycyclic compound of the present invention includes a fused polycyclic skeleton represented by the formula [1] and a substituted phenyl group represented by the formula [2]. As for the three-dimensional positional relationship between the fused polycyclic skeleton and the phenyl group, the skeleton and the group are not in the same plane as illustrated in FIG. 1. In the case where a substituent is introduced into the substituted phenyl group represented by the formula [2] at the position of $R_{21}$, the substituent is introduced on the same plane as the plane including the fused polycyclic skeleton represented by the formula [1] (xy plane). On the other hand, in the case where a substituent is introduced into the substituted phenyl group represented by the formula [2] at the position of $R_{19}$, $R_{20}$, $R_{22}$, or $R_{23}$, the substituent is introduced into a plane (xz plane) misaligned in a vertical direction from the plane of the formula [1] as long as a dihedral angle formed between the plane including the skeleton represented by the formula [1] and the plane including the substituent represented by the formula [2] does not become 0°.

Accordingly, it is considered that when the dihedral angle formed between the plane including the skeleton represented by the formula [1] and the plane including the skeleton represented by the formula [2] becomes 90°, the substituent introduced into $R_{19}$, $R_{20}$, $R_{22}$, or $R_{23}$ in the formula [2] acts most effectively as a sterically-hindering group for the plane including the skeleton represented by the formula [1].

Therefore, in order to suppress the intermolecular stacking of the plane including the skeleton represented by the formula [2], introduction of a substituent of the formula [2] into any of $R_1$, $R_2$, $R_7$, $R_8$, $R_{11}$, and $R_{16}$ in the formula [1] is expected to achieve the highest effect. That is, a substituent in the formula [2] is introduced preferably into any of $R_1$, $R_2$, $R_7$, $R_8$, $R_{11}$ and $R_{16}$ in the formula [1], more preferably into two or more of $R_1$, $R_2$, $R_7$, $R_8$, $R_{11}$, and $R_{16}$.

This is because the substituent in the formula [2] introduced in the substitution positions is strongly affected by steric repulsion of substituents or hydrogen atoms on the both sides. Therefore, the substituent in the formula [2] may be introduced in such a manner that the plane including the introduced substituent in the formula [2] is nearly perpendicular to the plane including the fused polycyclic ring skeleton represented by the formula [1]. As a result, the stacking inhibition effects of the substituent introduced into $R_{19}$, $R_{20}$, $R_{22}$, and $R_{23}$ in the formula [2] are expected to increase.

Lowering of the stacking property of a molecule is expected to achieve the following three effects.

(i) The crystallinity of the molecule itself is expected to lower, resulting in improving stability of an organic thin film. Therefore, when the fused polycyclic compound of the present invention is used as a host or guest of a light-emitting layer (hereinafter, sometimes referred to as "emission layer"), the device can suppress emission degradation due to energization. This is because it is considered that a cause for the emission degradation of an organic light-emitting device due to energization is crystallization of the organic compound.

(ii) Concentration quenching (phenomenon in which emission efficiency is lowered due to an increase in the concentration of a guest in a light-emitting device) can be suppressed. This is because suppression of the stacking property of a molecule may suppress quenching due to stacking of the same molecule and formation of an excimer. Therefore, if the fused polycyclic compound of the present invention is used as a light-emitting material, lowering of the emission efficiency and change in emission color can be suppressed.

(iii) The sublimation property is expected to improve. This is because it is considered that a decrease in the intermolecular interaction decreases the sublimation temperature. Therefore, a sublimation purification method may be employed for purification of the compound. In addition, if the sublimation temperature decreases, it is possible to suppress the thermal decomposition of a material when an organic light-emitting device is produced by a vacuum evaporation method.

The fused polycyclic compound of the present invention can be synthesized via, for example, the following route. However, the present invention is not limited thereto.

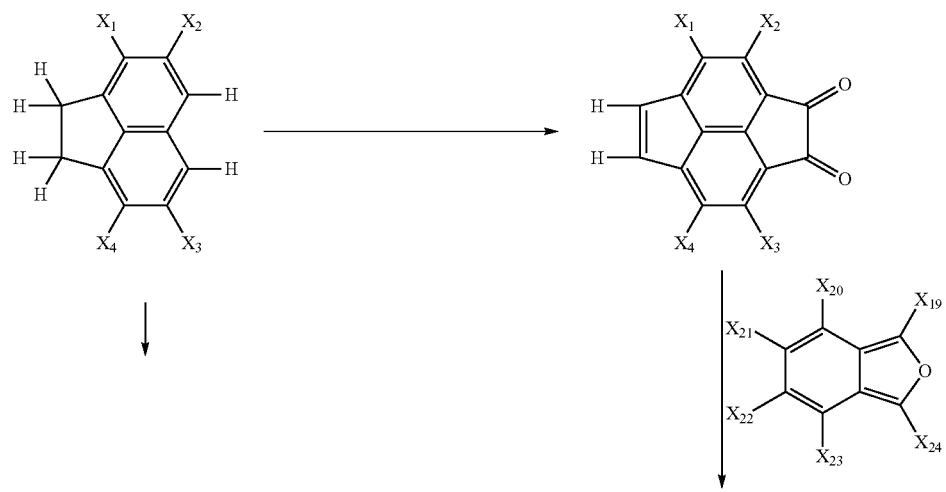

7
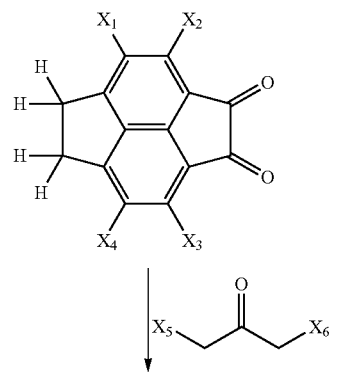
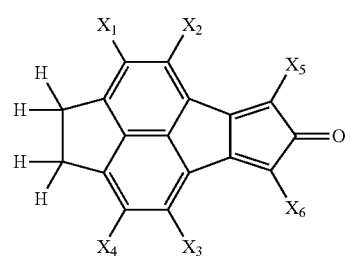
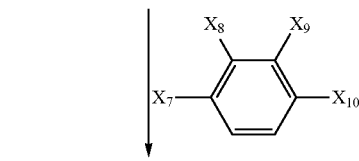
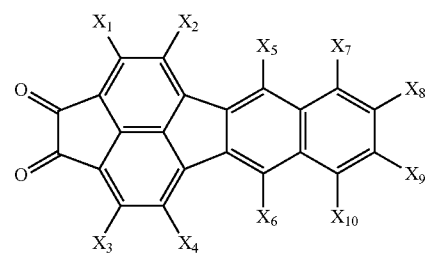
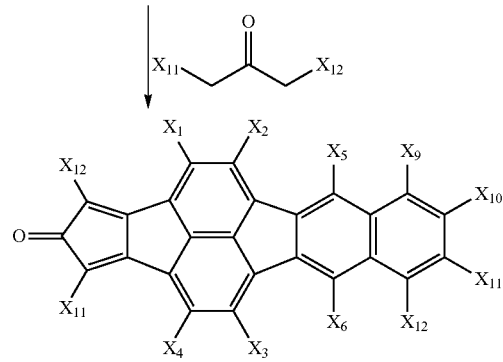
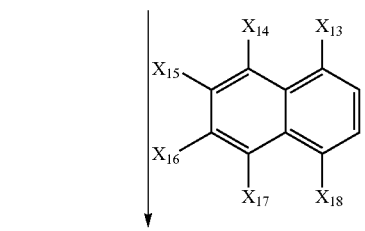
8
-continued
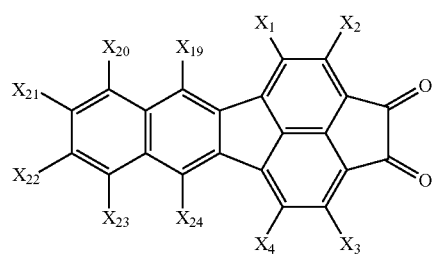
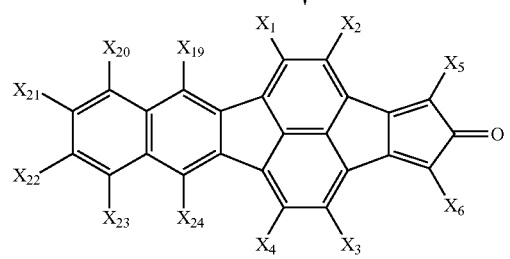
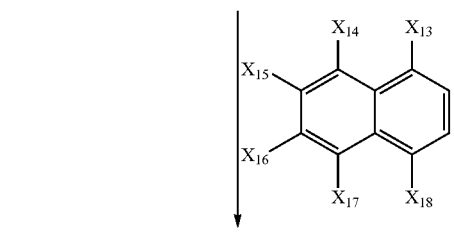
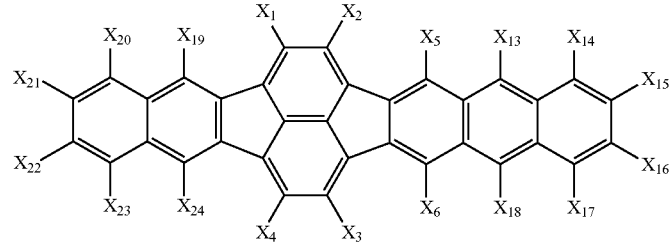

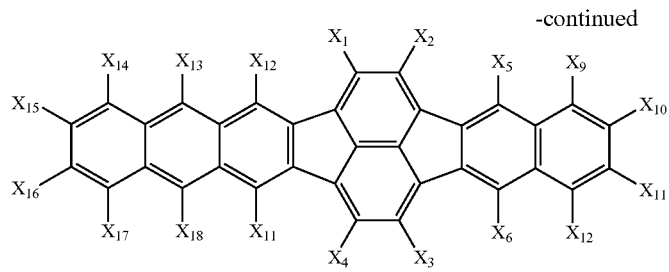

From the viewpoint of stability of the synthesis intermediates, $X_2$, $X_5$, $X_6$, $X_{11}$, $X_{12}$, and $X_{19}$ in the above-mentioned synthesis route are preferably aryl groups. That is, $R_1$, $R_8$, $R_{11}$, and $R_{16}$ in the formula [1] are each preferably an aryl group.

The fused polycyclic compound of the present invention is desirably purified to such a sufficient extent that an impurity is removed from the compound. A cause for emission degradation due to energization is, for example, the inclusion of an impurity. When a polymer compound is used as a component for the device, since it is difficult to remove an impurity in the polymer, the impurity is apt to be incorporated into the device, which causes a reduction in the life of the device. On the other hand, because the compound is a single compound, an impurity can be easily removed from the fused polycyclic compound of the present invention by appropriately employing a purification method such as a recrystallization method, a column chromatography method, or a sublimation purification method. Accordingly, the use of the fused polycyclic compound of the present invention as a component for an organic light-emitting device improves the durability of the organic light-emitting device.

Specific examples of the fused polycyclic compound of the present invention are shown below. However, those are merely representative examples, and the fused polycyclic compound of the present invention is not limited to the examples.

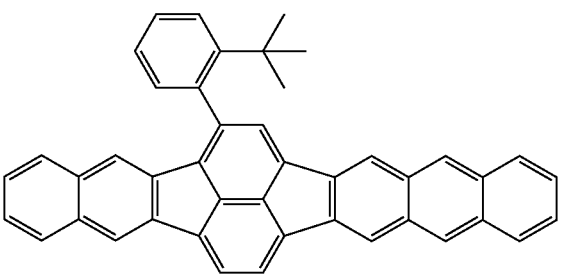

AA-3

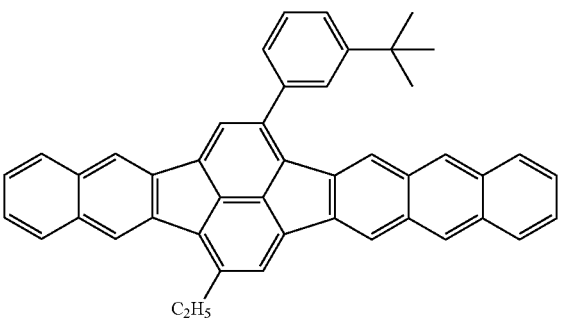

AA-4

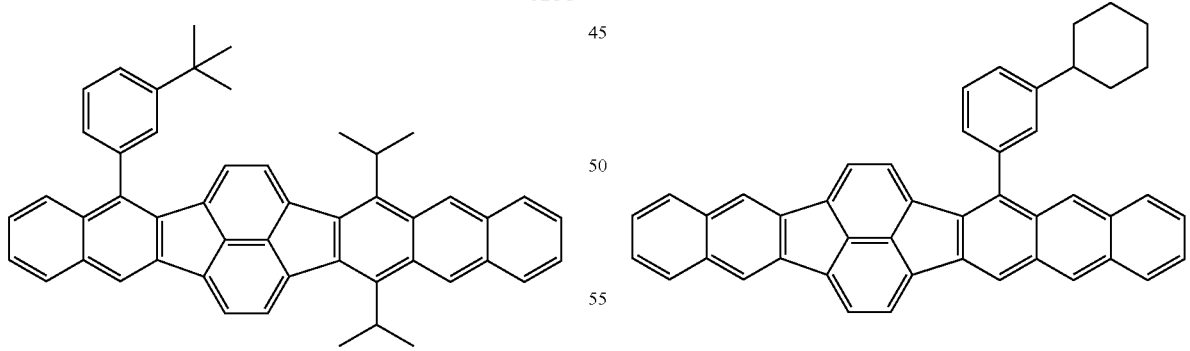

AA-1

AA-5

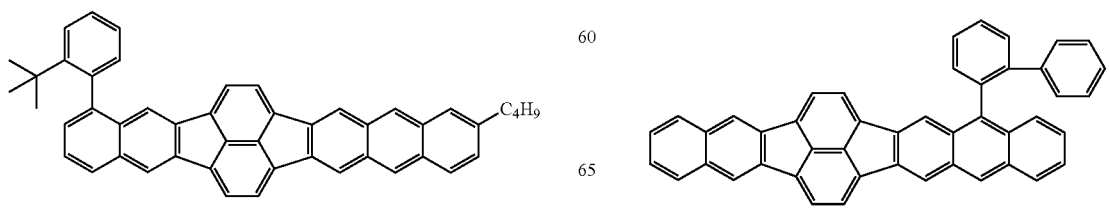

AA-2

AA-6

AA-7
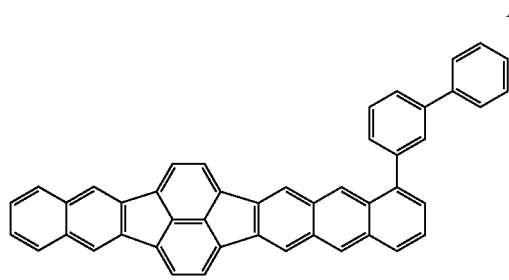
AA-8
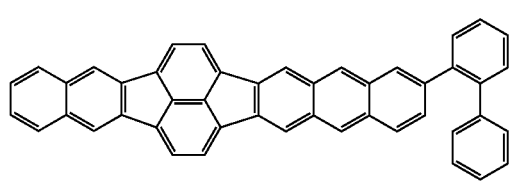
AA-9
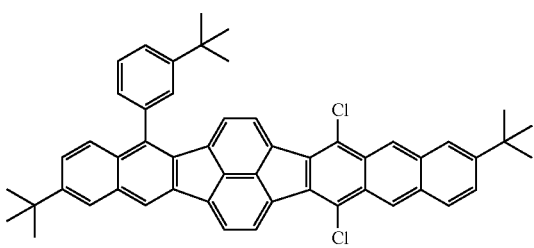
AB-1
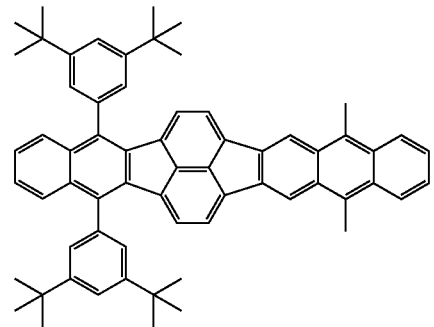
AB-2
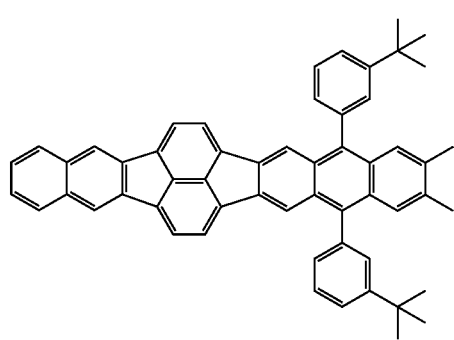
AB-3
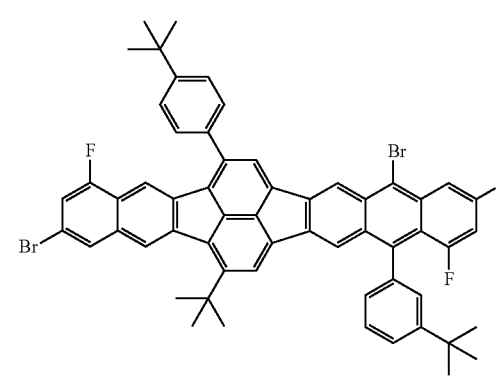
AB-4
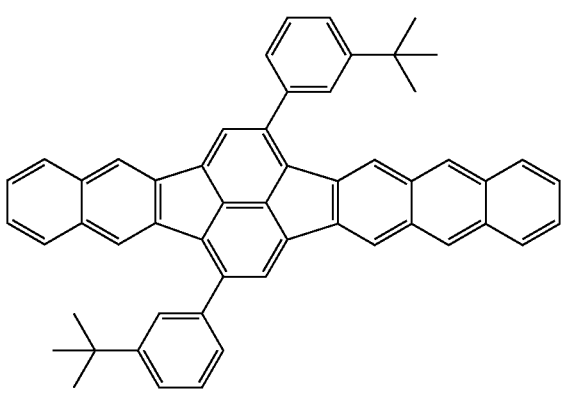
AB-5
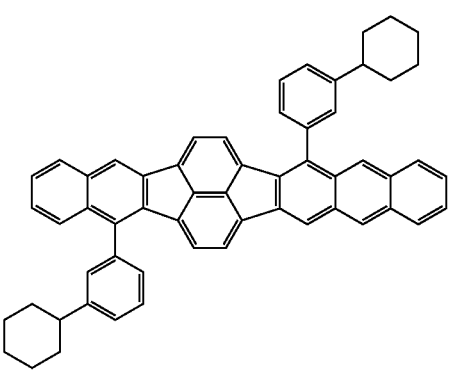
AB-6
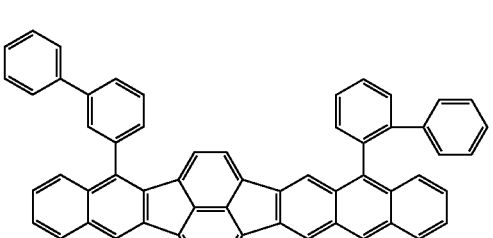

AB-7
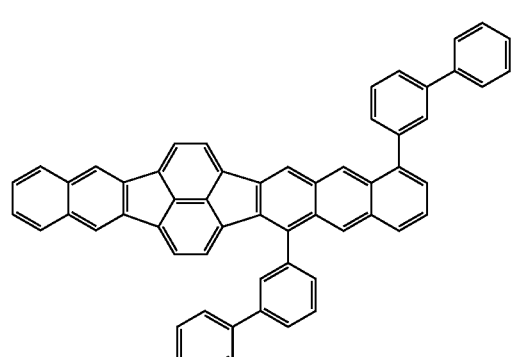
AB-8
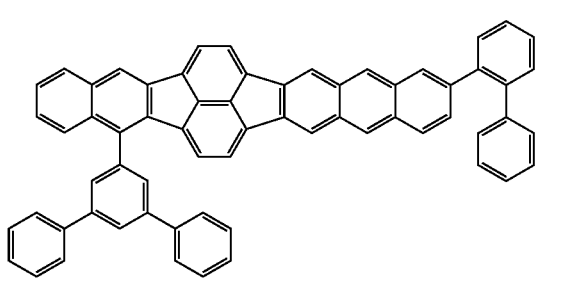
AB-9
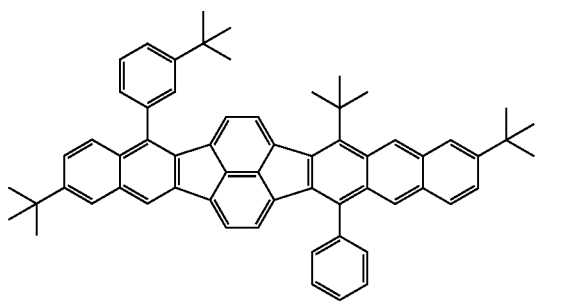
AC-1
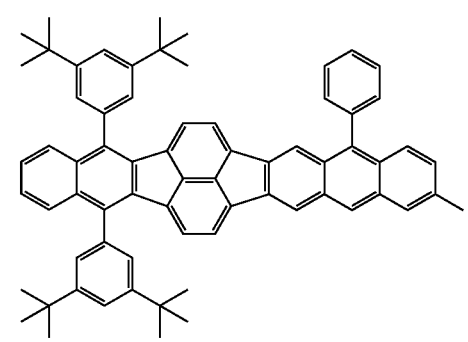
AC-2
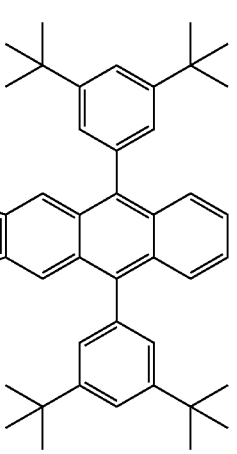
AC-3
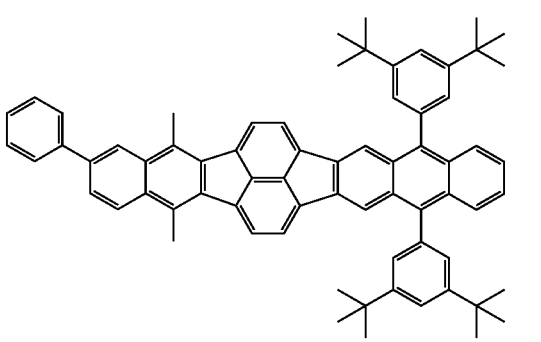
AC-4
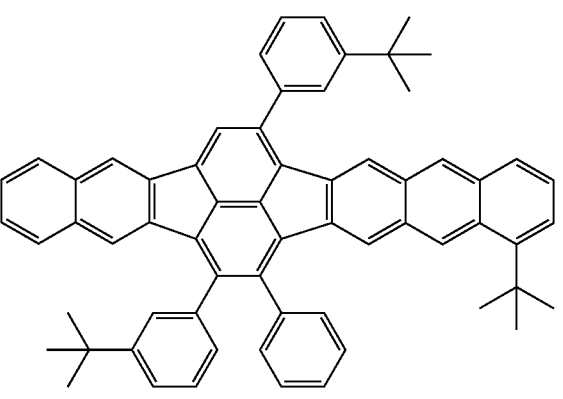

-continued
AC-5
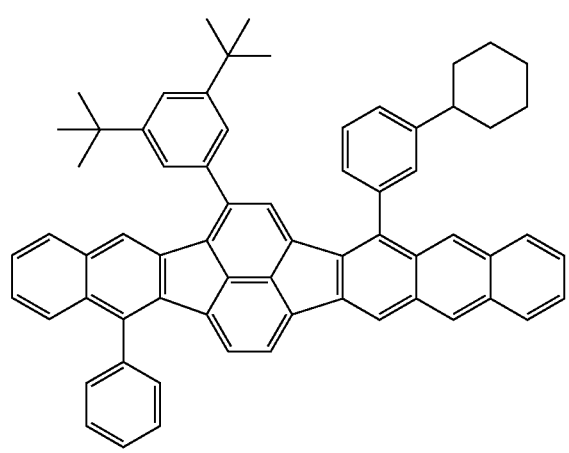
AC-6
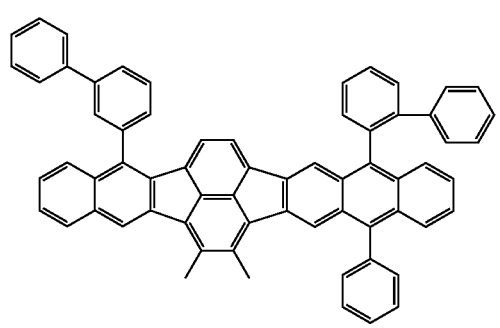
AC-7
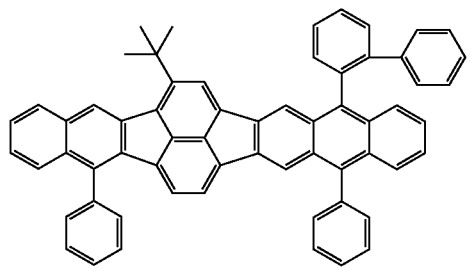
AC-8
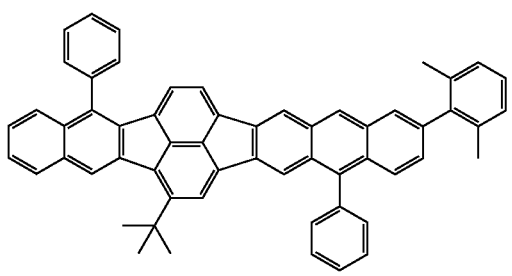
-continued
AC-9
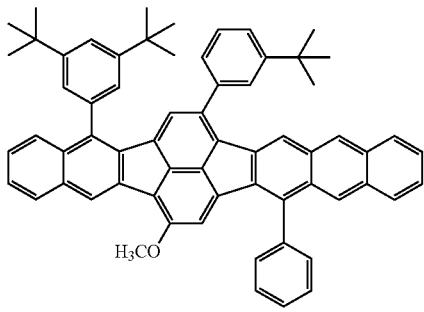
AD-1
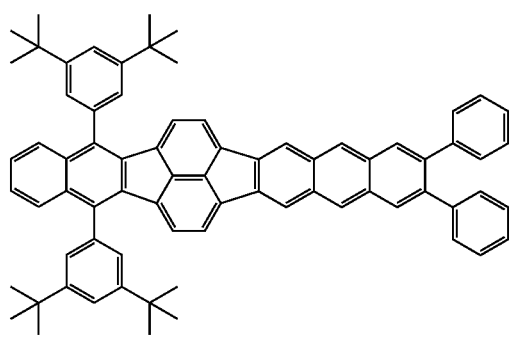
AD-2
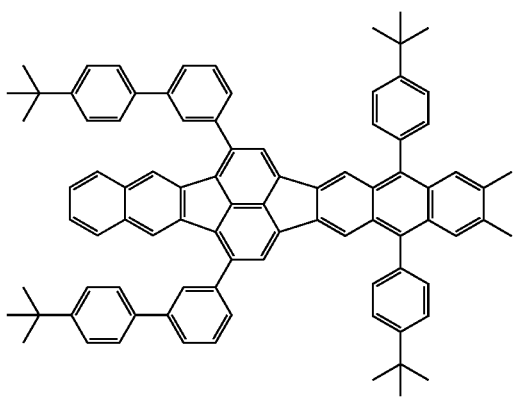
AD-3
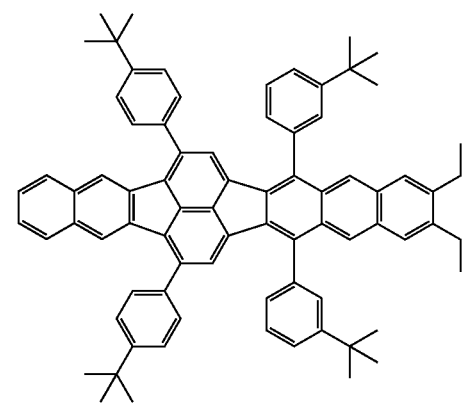

-continued
AD-4
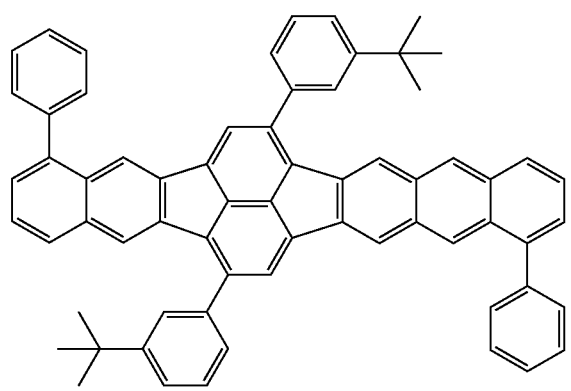
AD-5
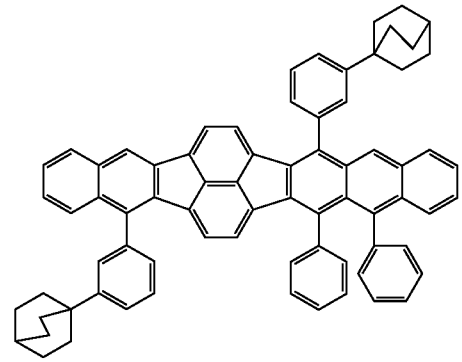
AD-6
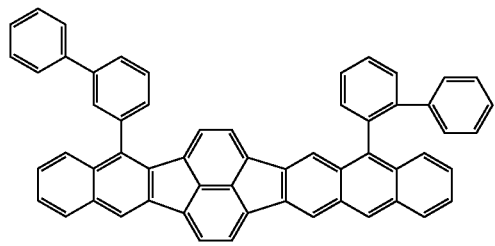
AD-7
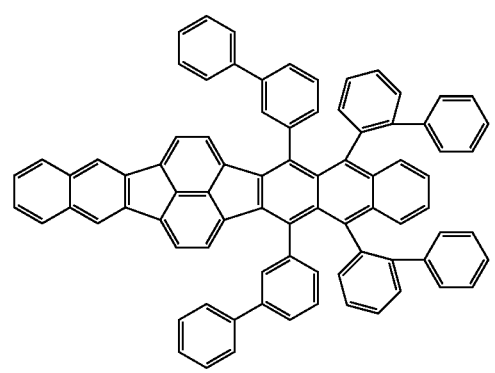
-continued
AD-8
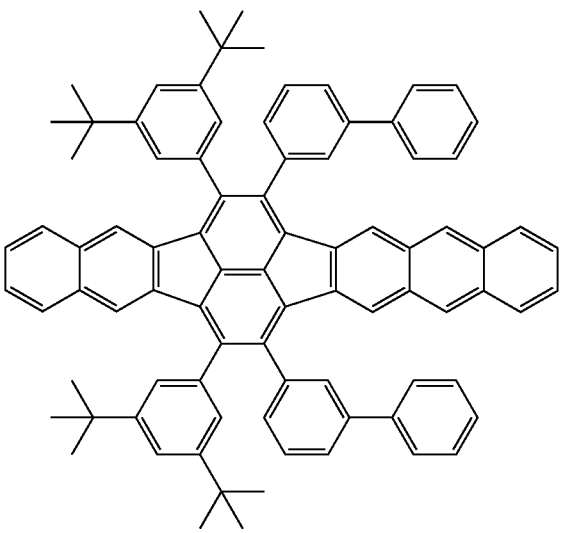
AD-9
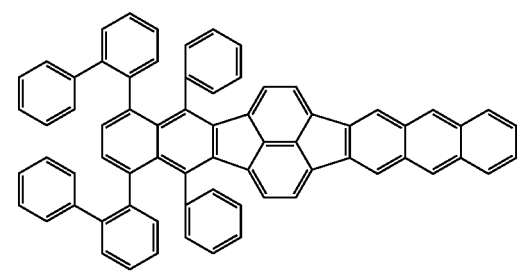
AE-1
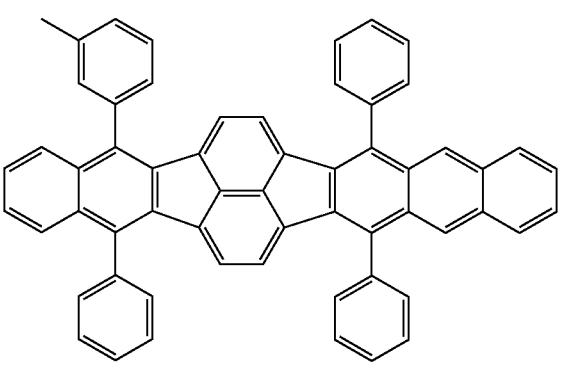
AE-2
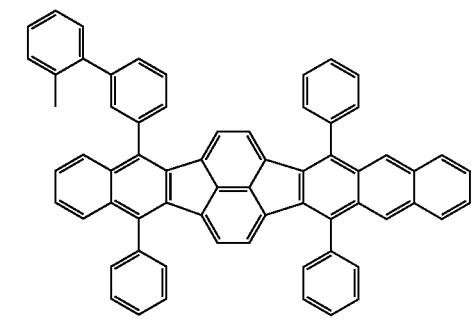

AE-3
AE-4
AE-5
AE-6
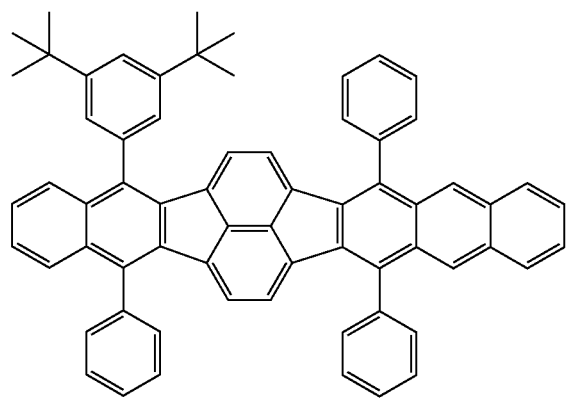
AE-7
AE-8
AE-9
AE-10
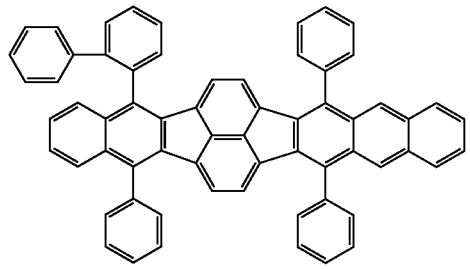
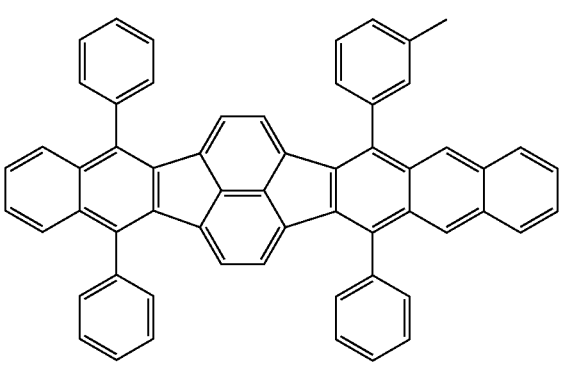
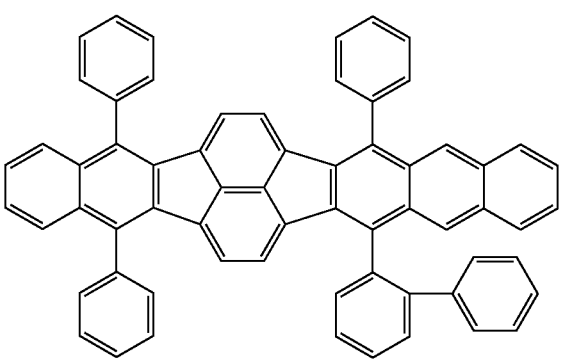
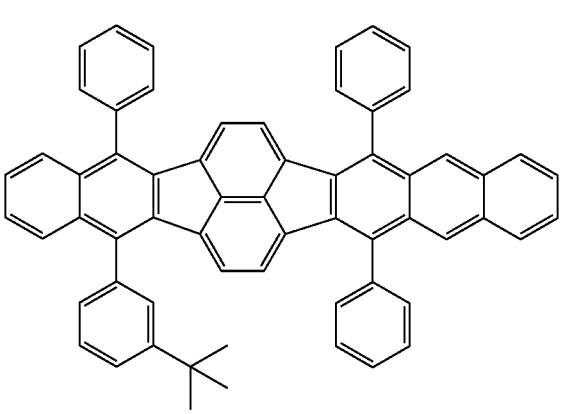

AE-11
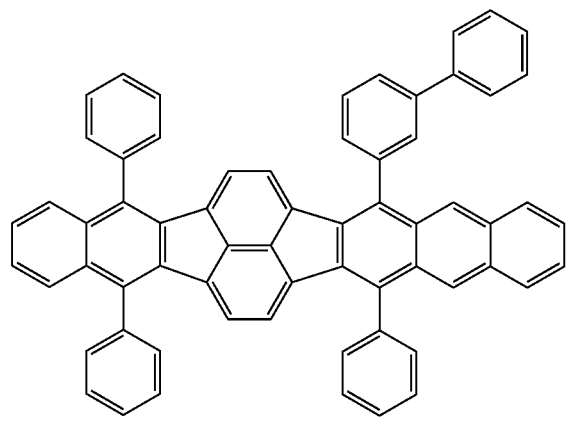
AE-15
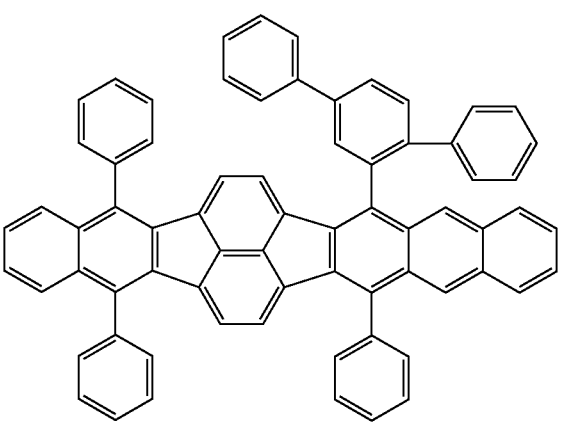
AE12
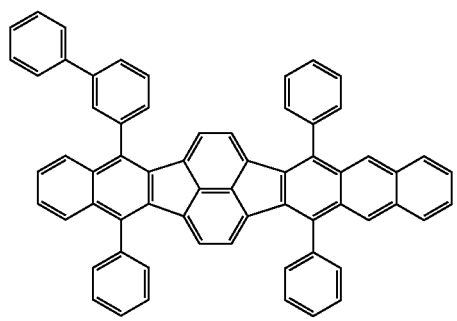
AE-16
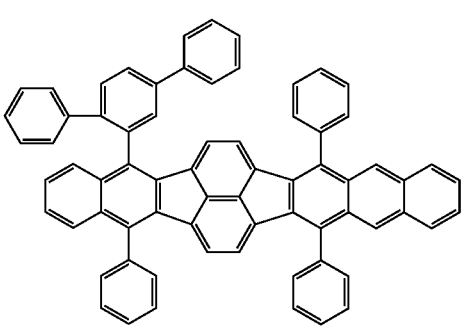
AE-13
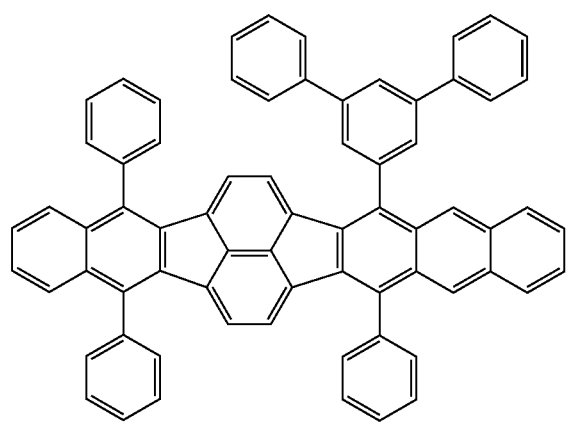
AE-17
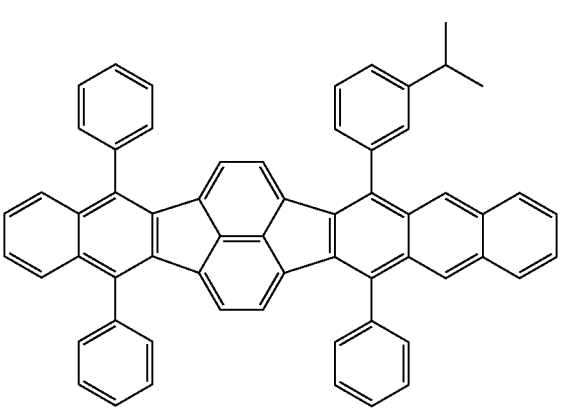
AE-14
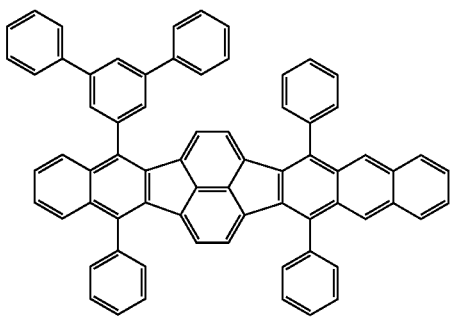
AE-18
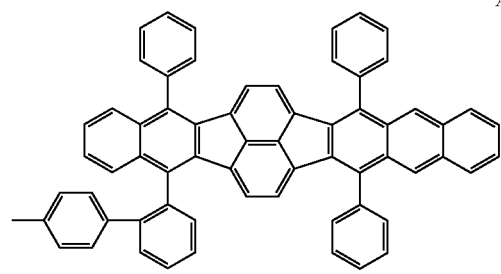

-continued
AE-19
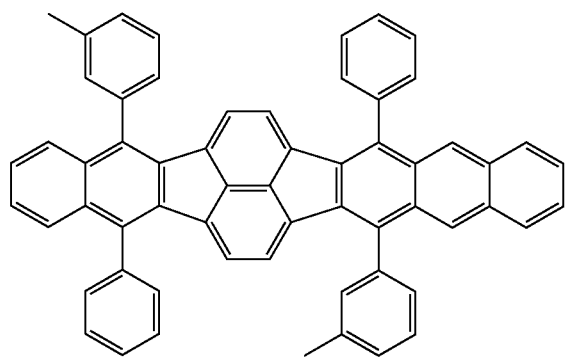
AE-20
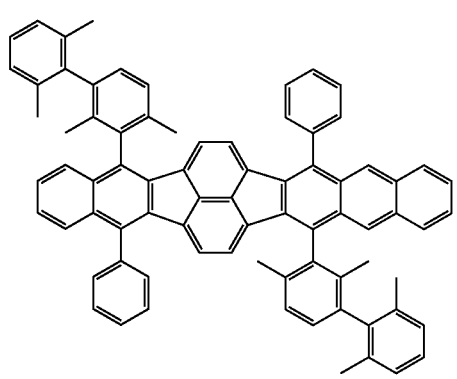
AE-21
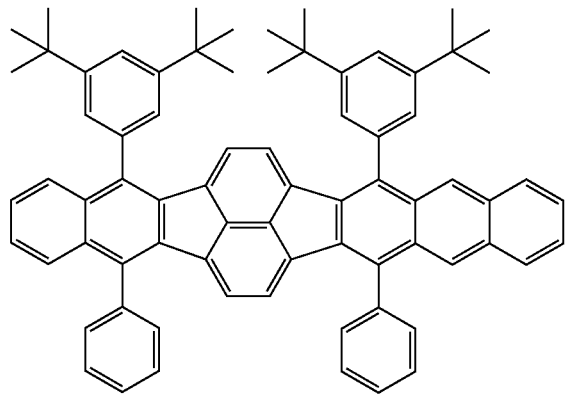
AE-22
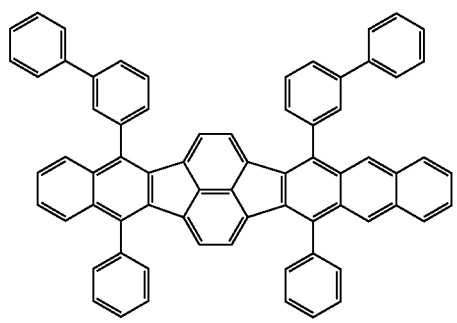
-continued
AE-23
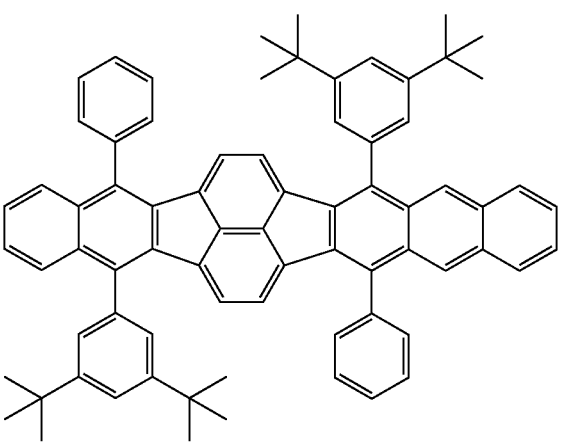
AE-24
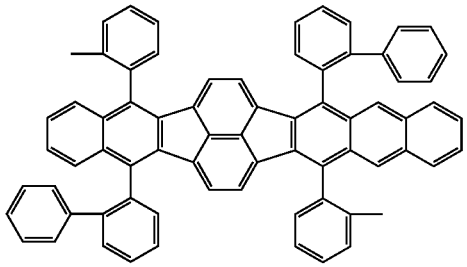
AE-25
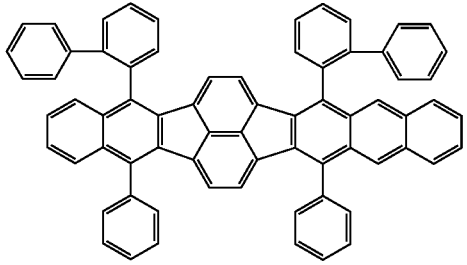
AE-26
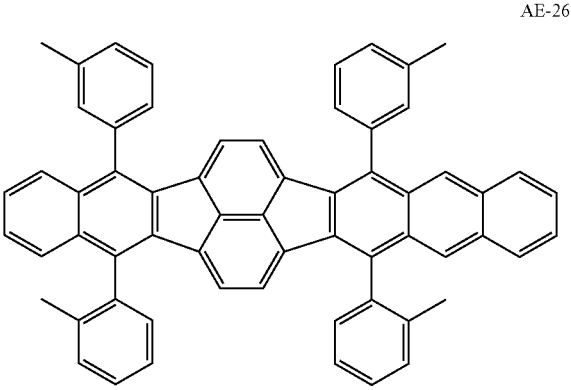

AE-27
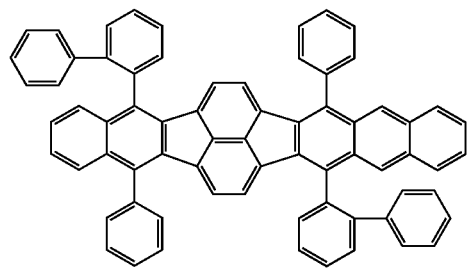
AE-28
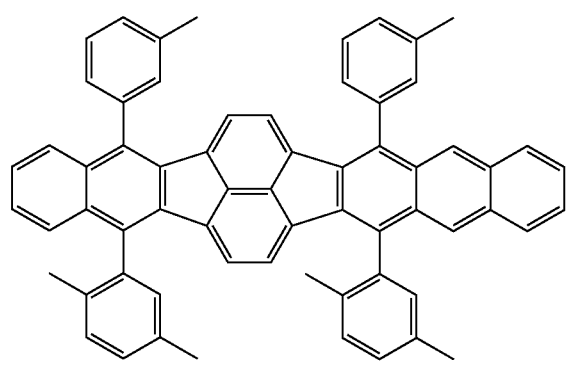
AE-29
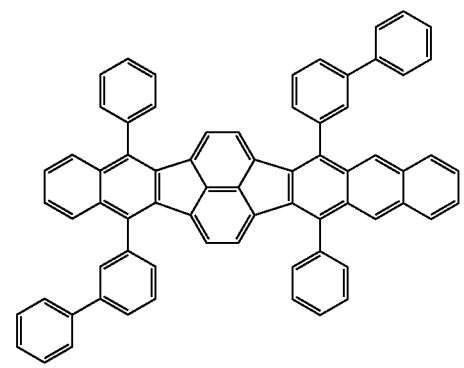
AE-30
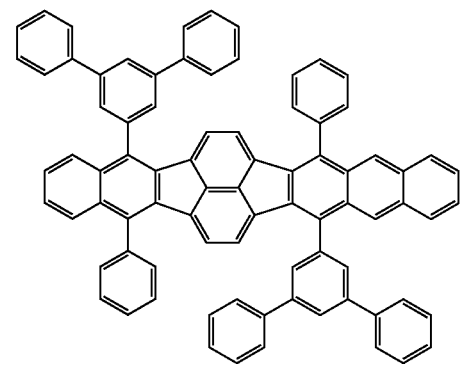
AE-31
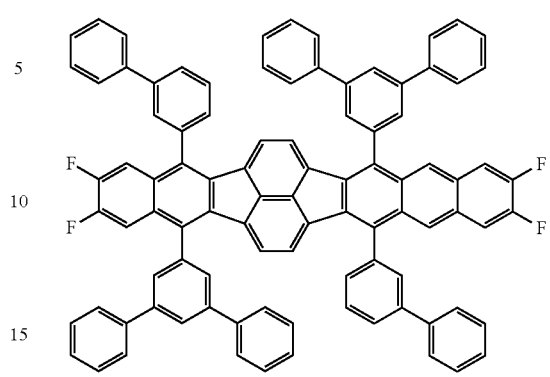
AE-32
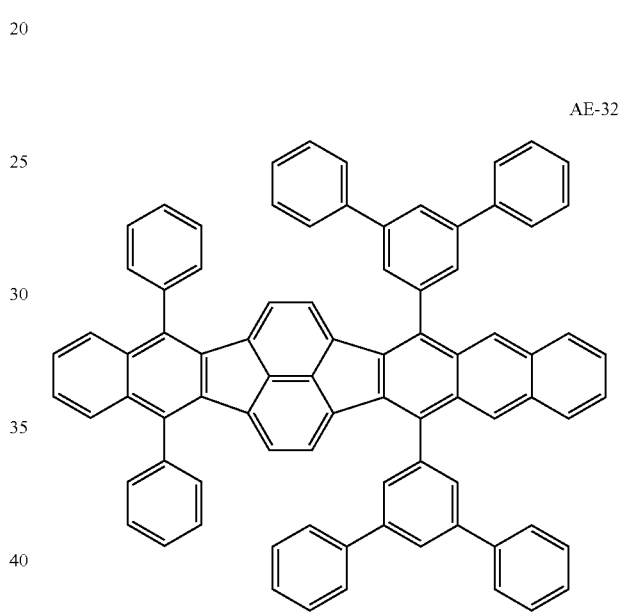
AE-33
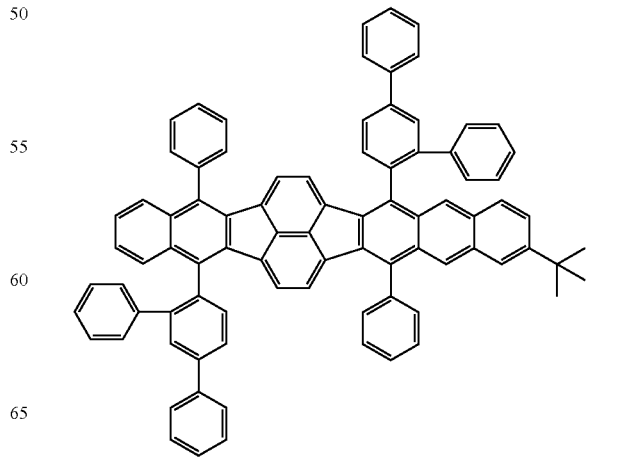

AE-34
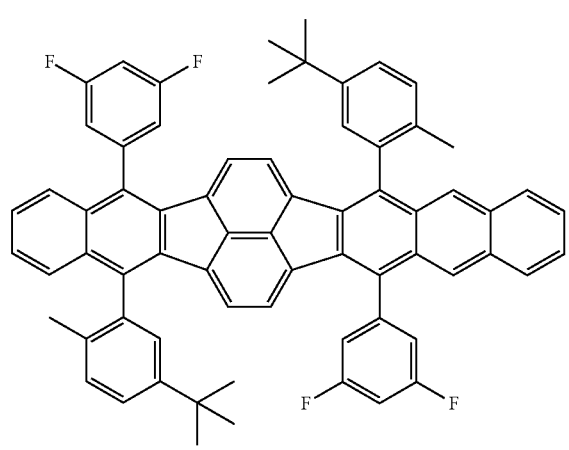
AE-35
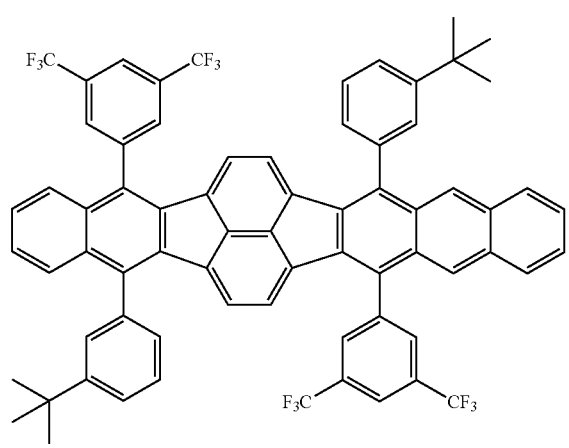
AE-36
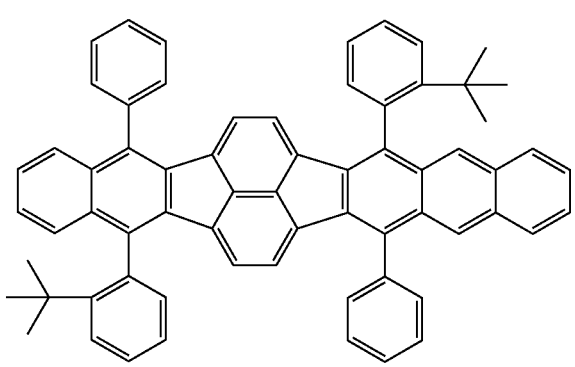
AE-37
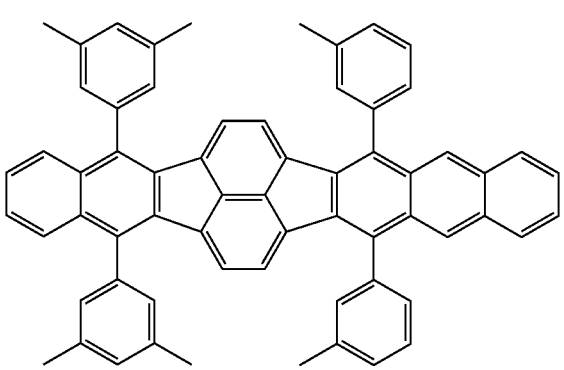
AE-38
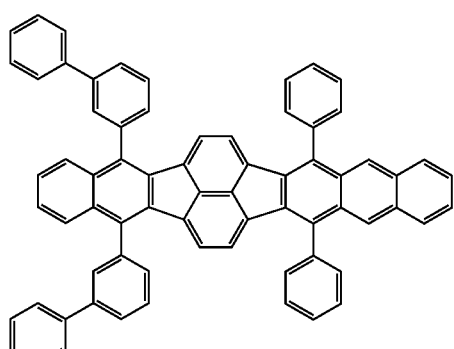
AE-39
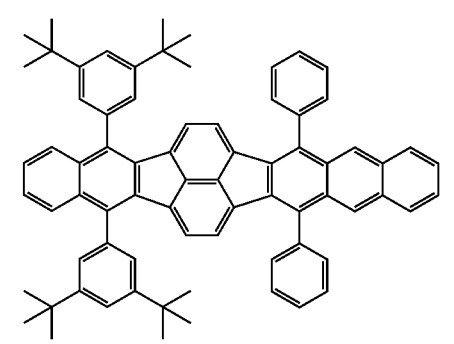
AE-40
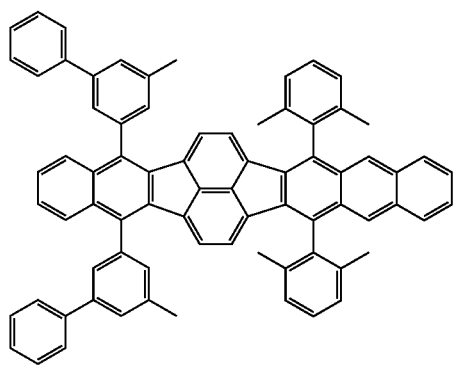

AE-41
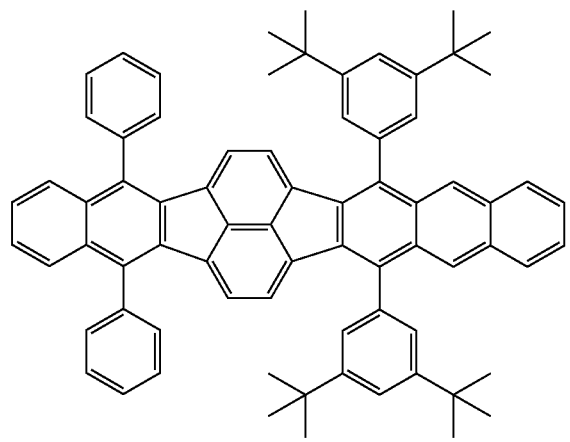
AE-42
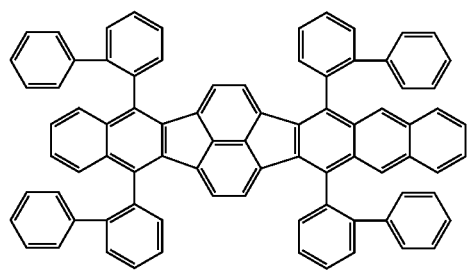
AE-43
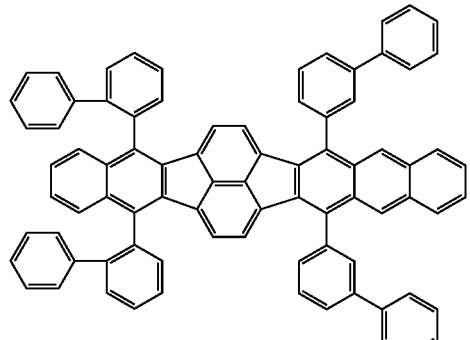
AE-44
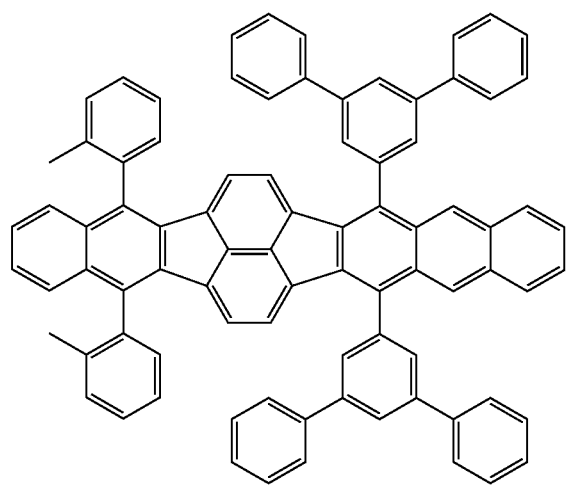
AE-45
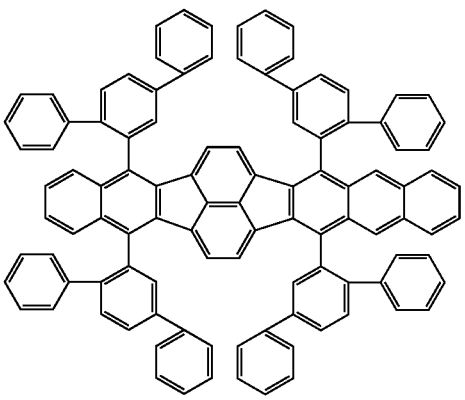
AE-46
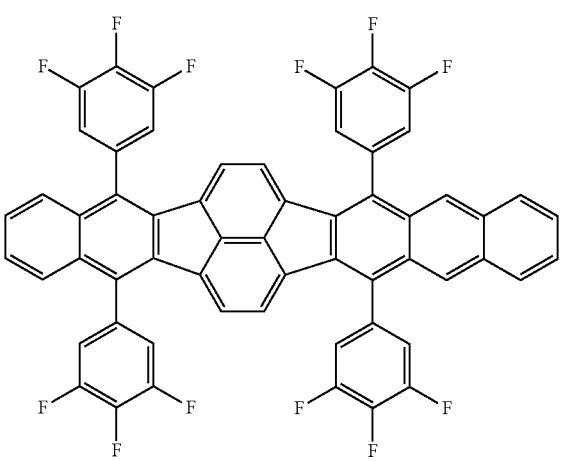
AE-47
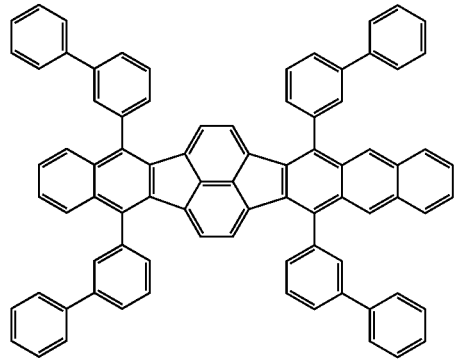
AE-48
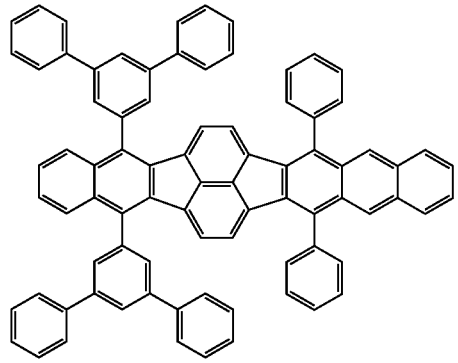

-continued
AE-49
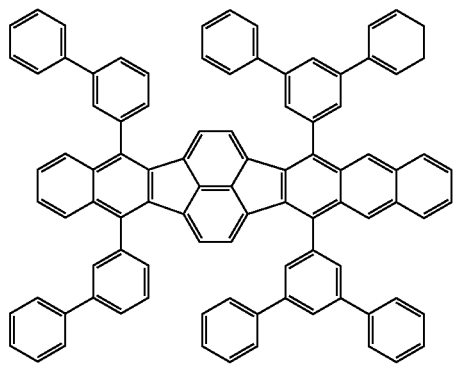
AE-52
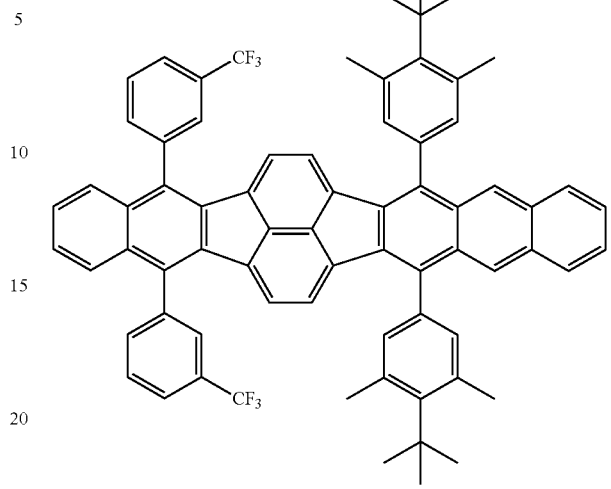
AE-50
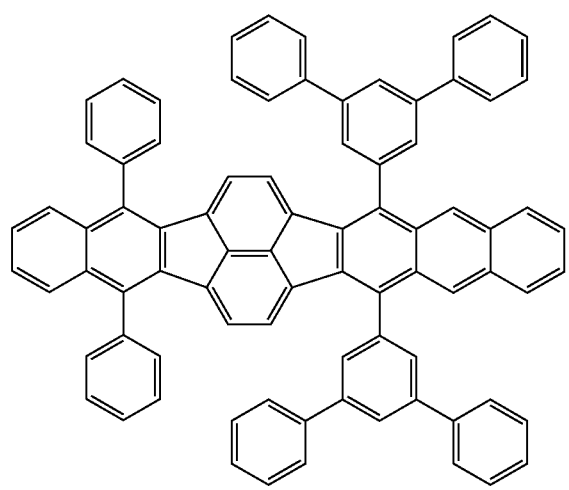
AE-53
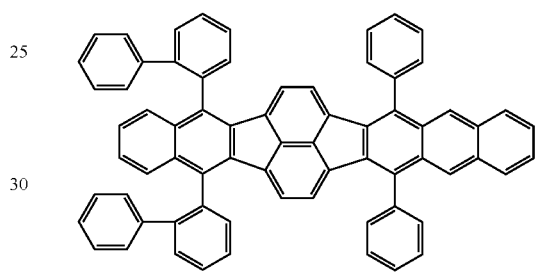
AE-54
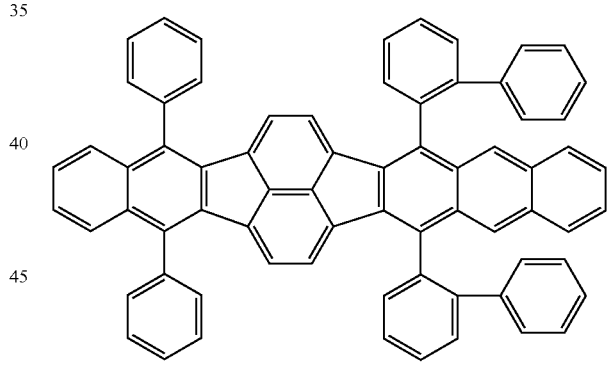
AE-51
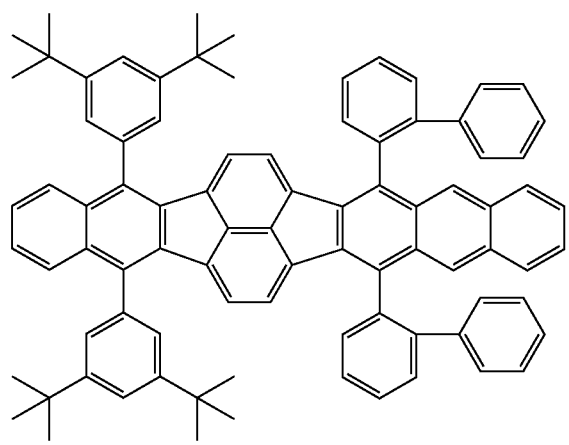
AE-55
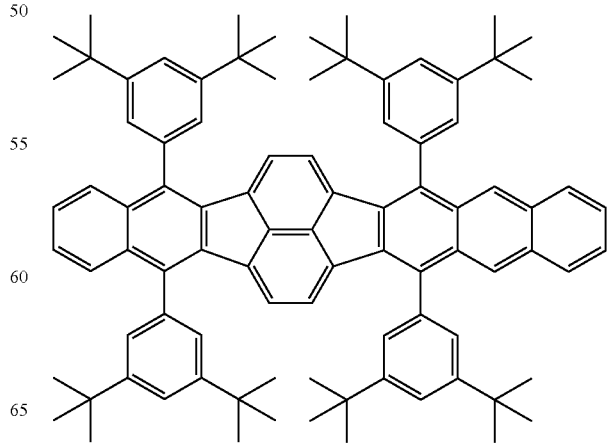

AE-56
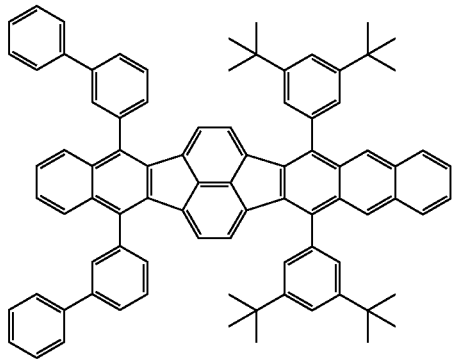
AE-59
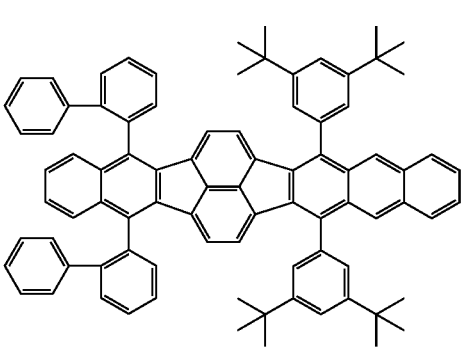
AE-57
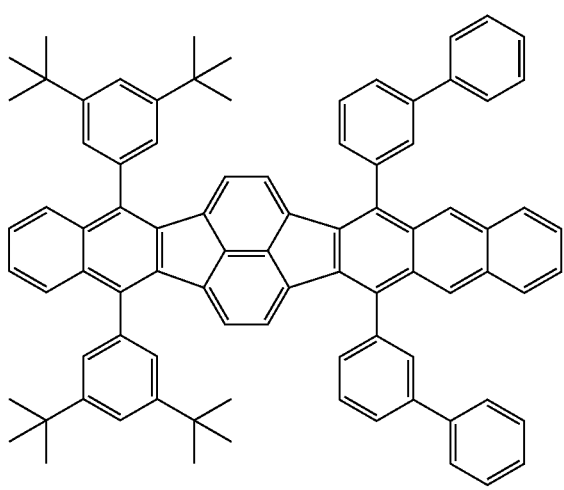
AE-60
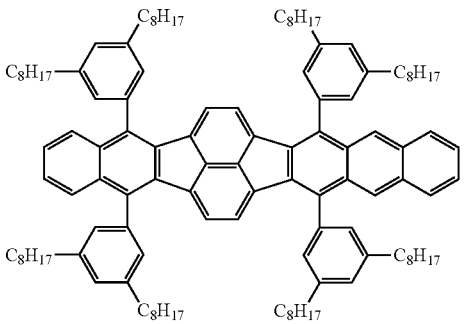
AE-61
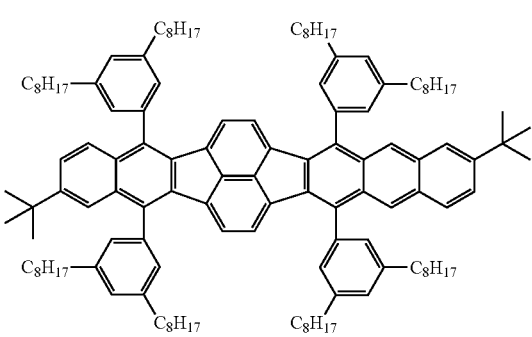
AE-58
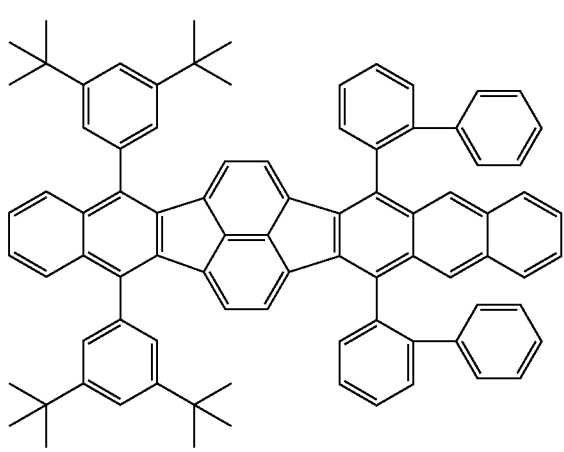
AE-62
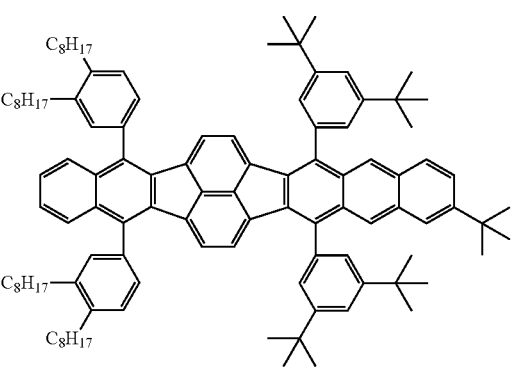

AE-63
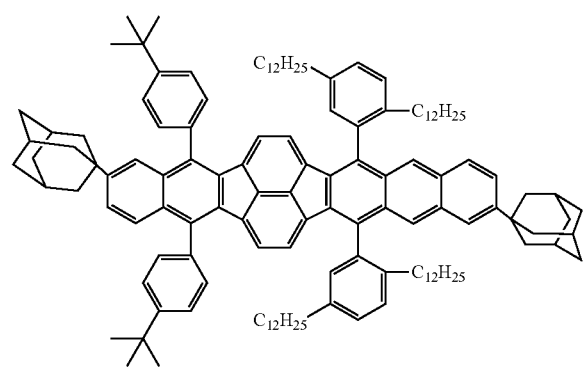
AE-66
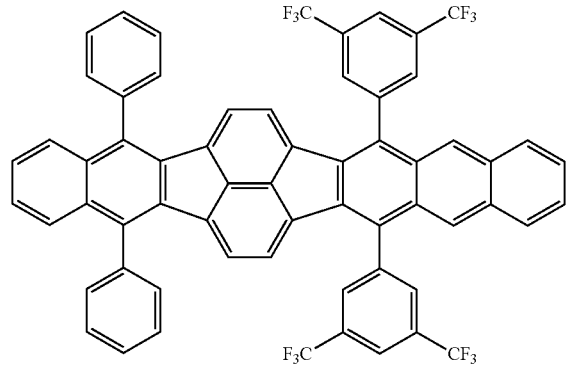
AE-64
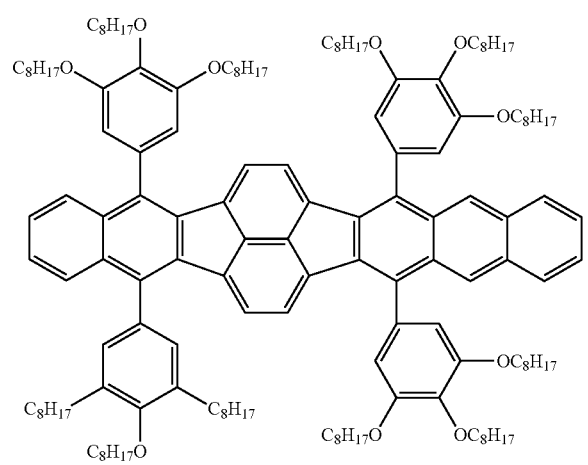
AE-67
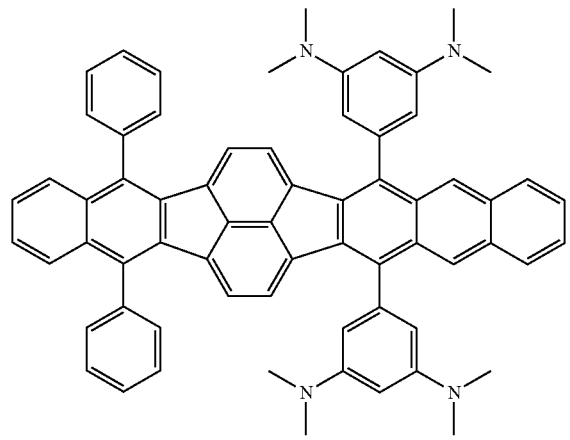
AE-65
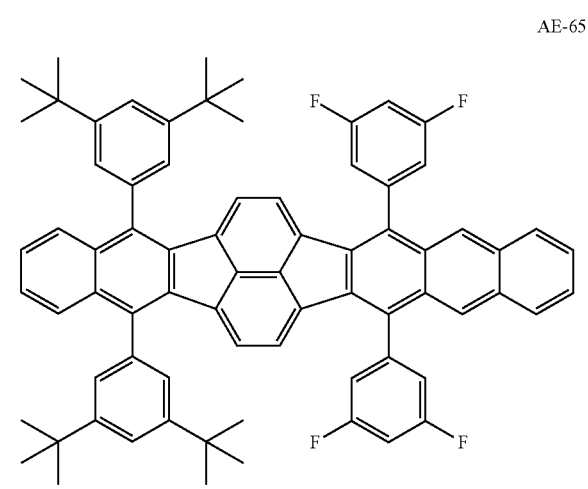
AE-68
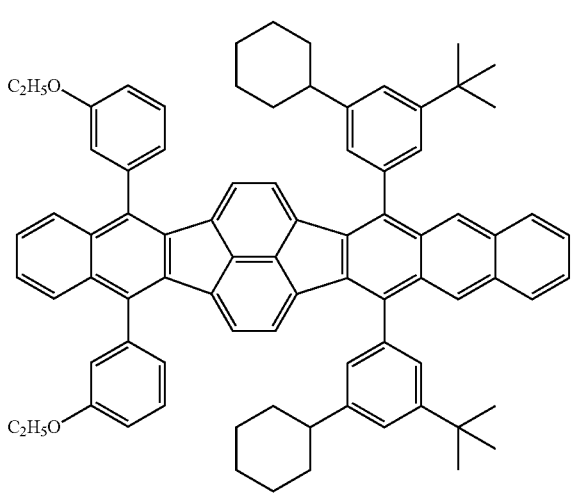

AE-69
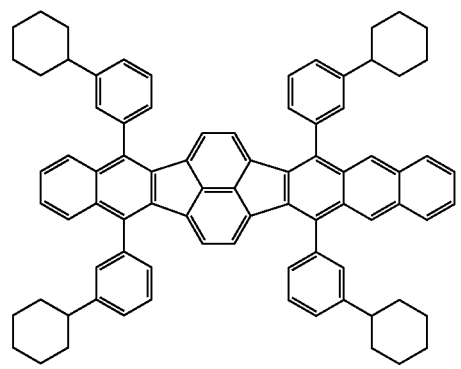
AF-1
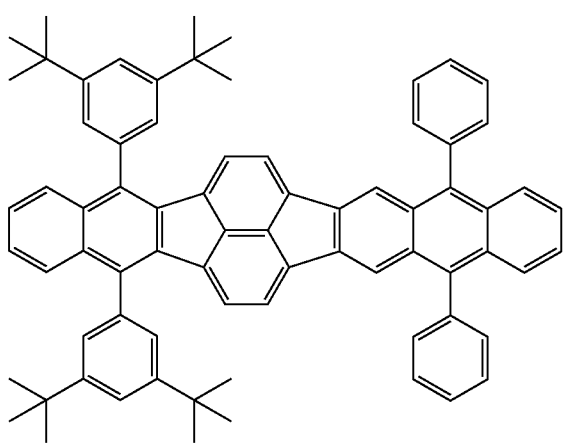
AF-2
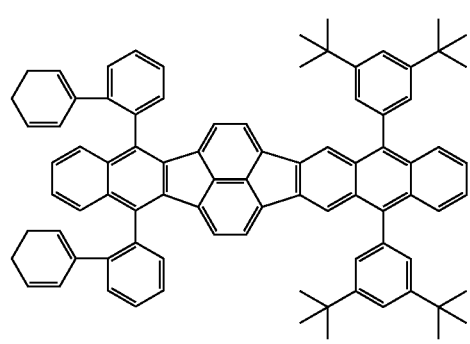
AF-3
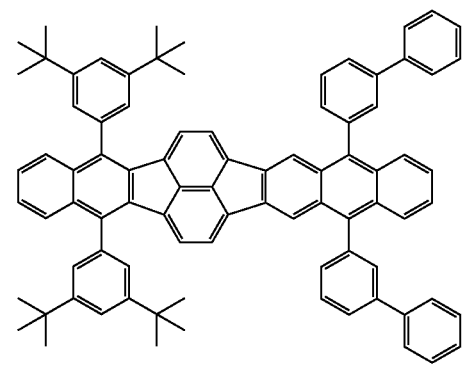
AF-4
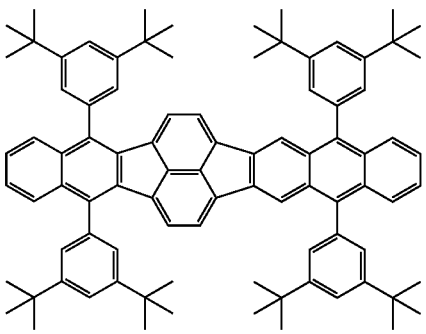
AF-5
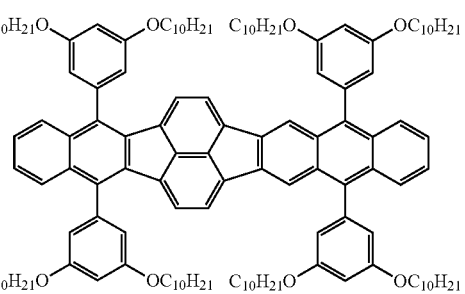
AF-6
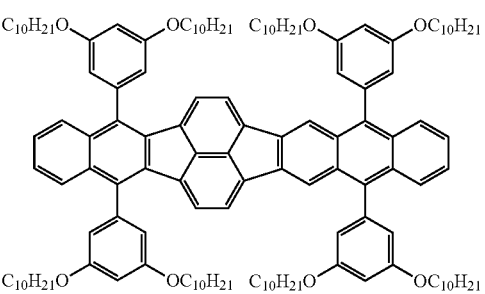
AF-7
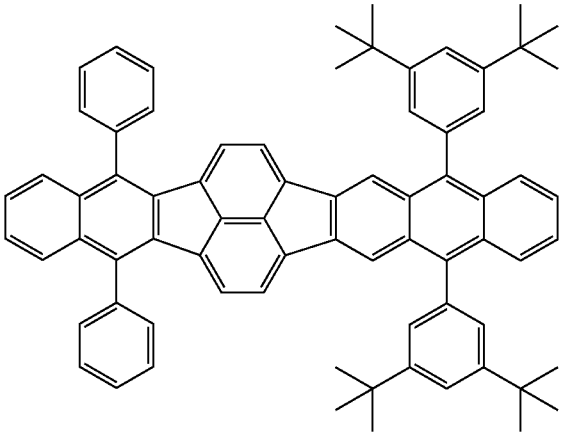

AF-8
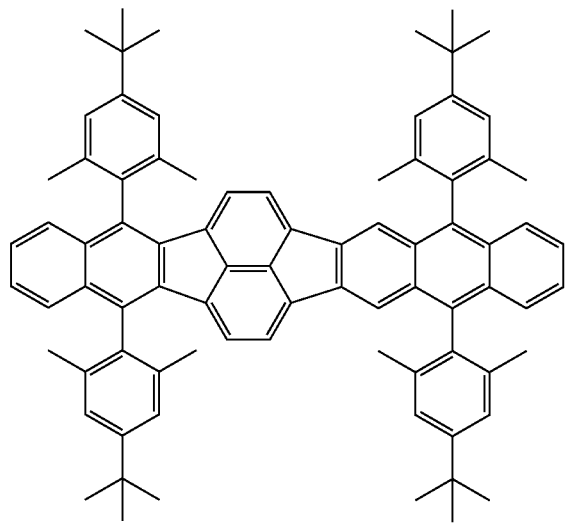
AF-9
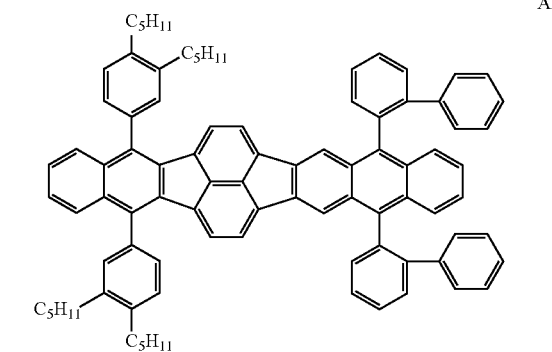
AF-10
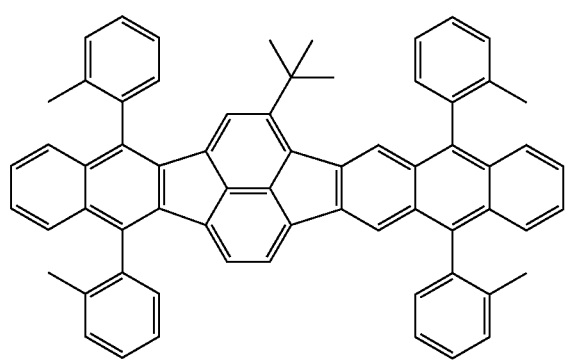
AF-11
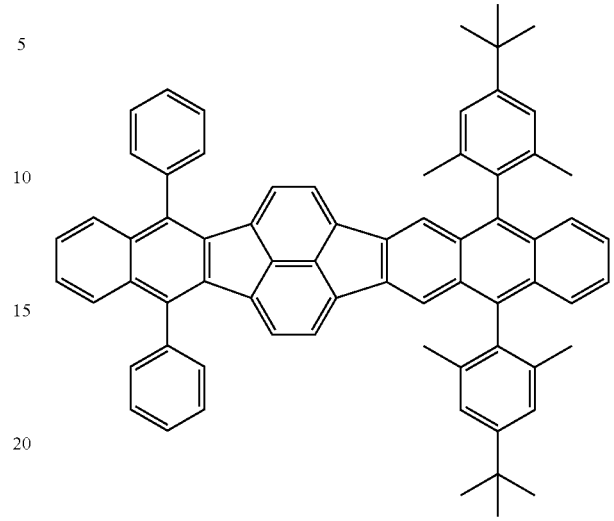
AF-12
AF-13
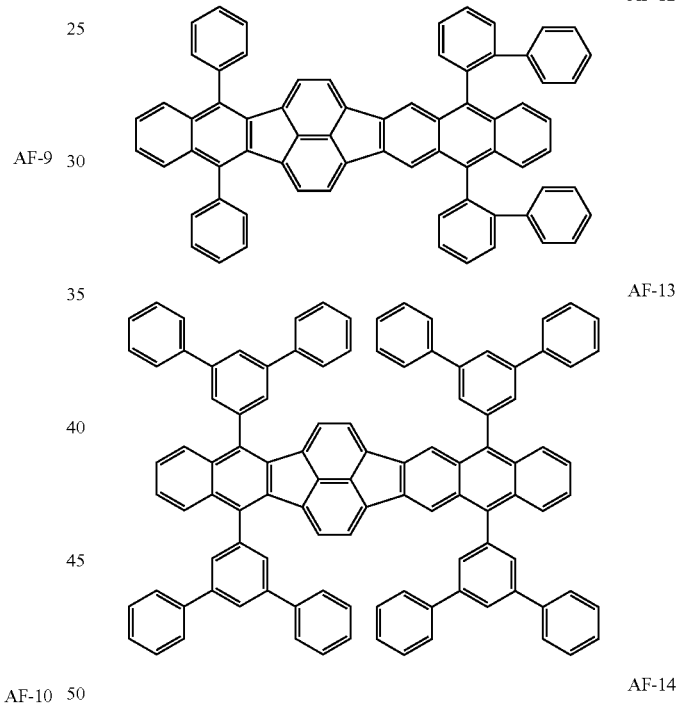
AF-14
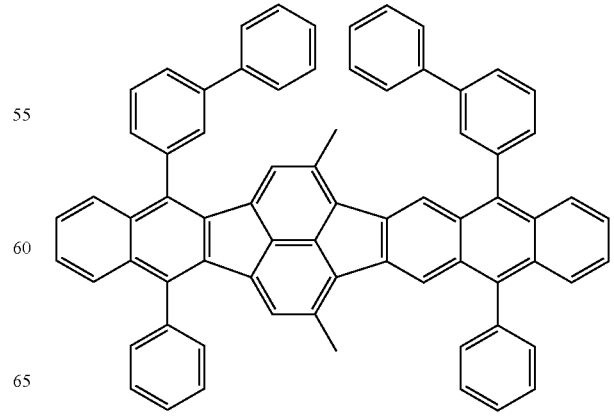

AF-15
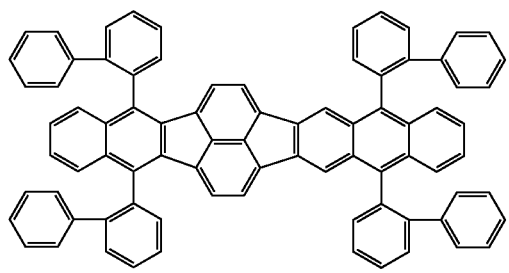
AF-16
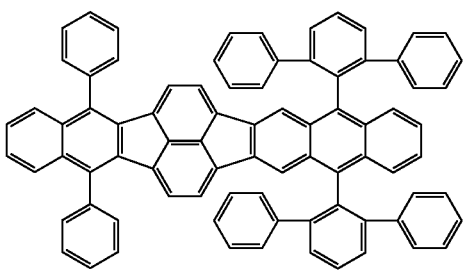
AF-17
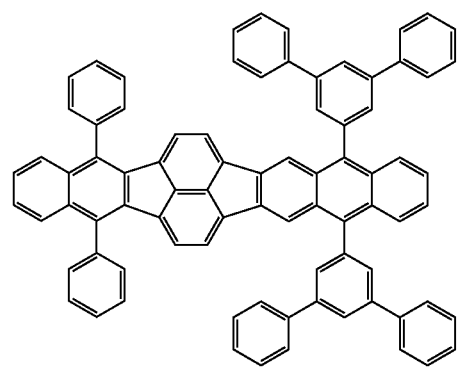
AF-18
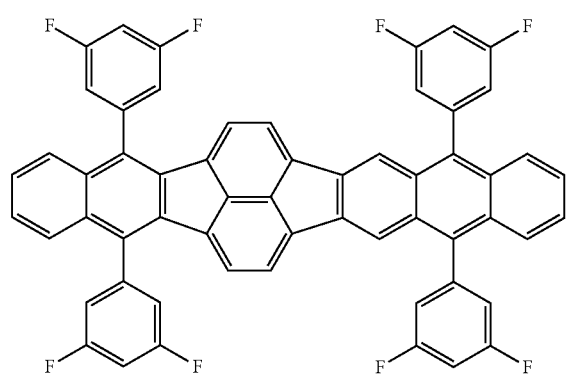
AG-1
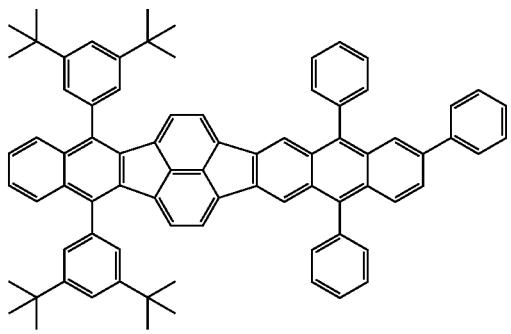
AG-2
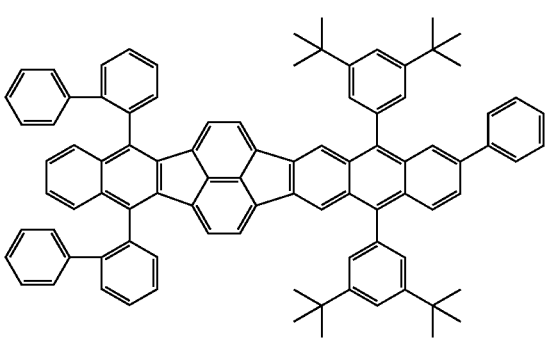
AG-3
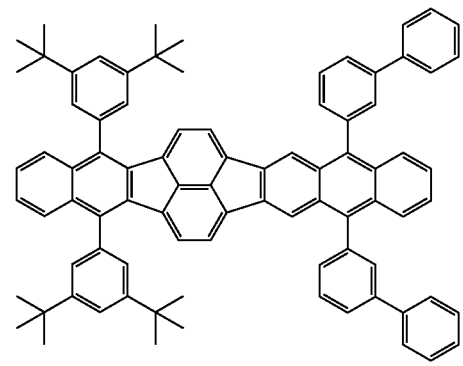
AG-4
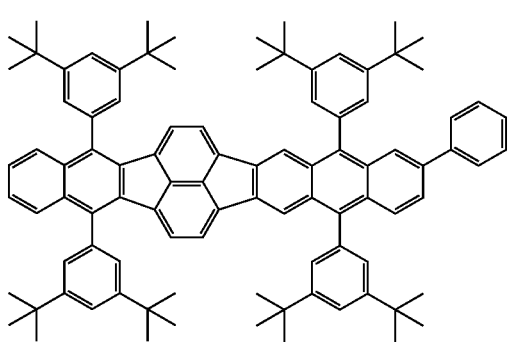

AG-5
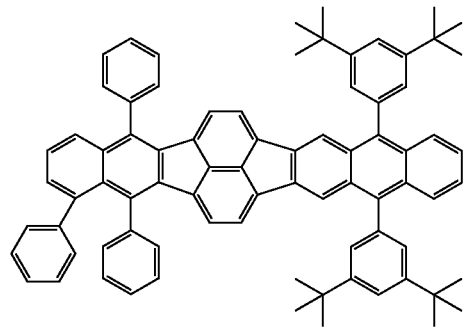
AG-6
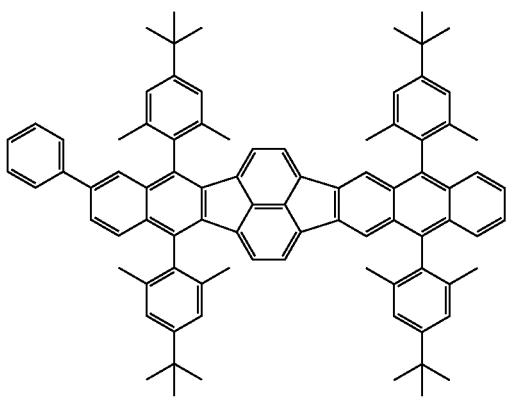
AG-7
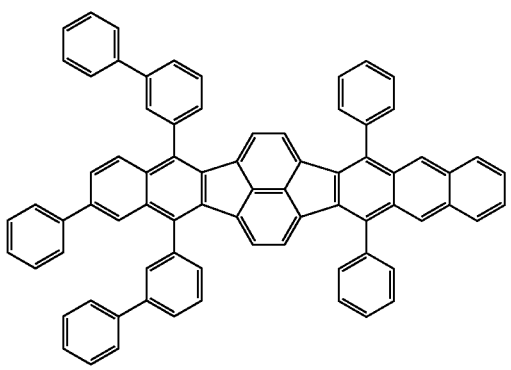
AG-8
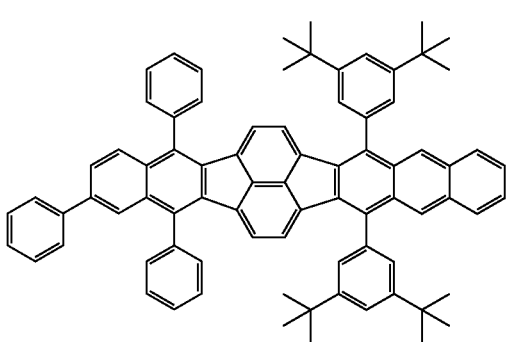
AG-9
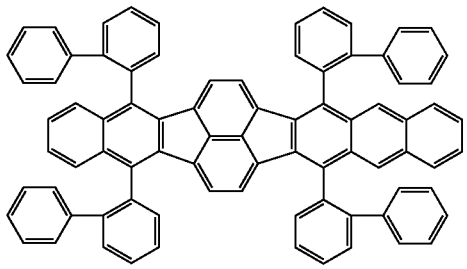
AG-10
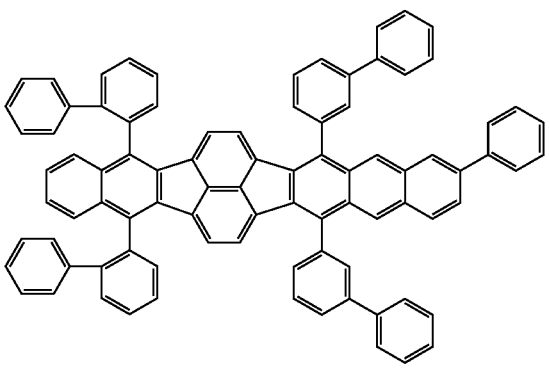
AG-11
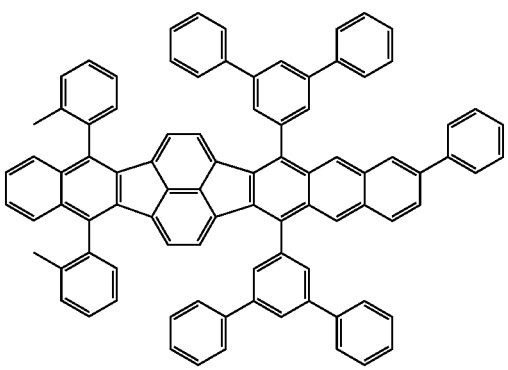
AG-12
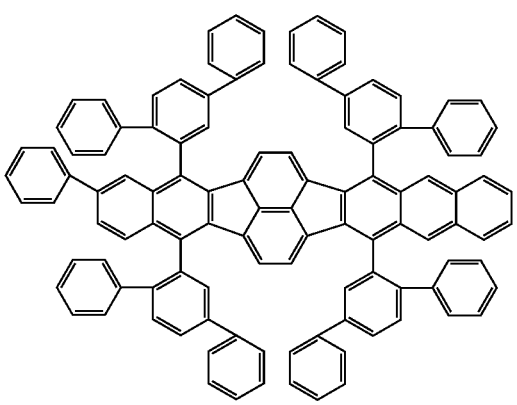

-continued
AG-13
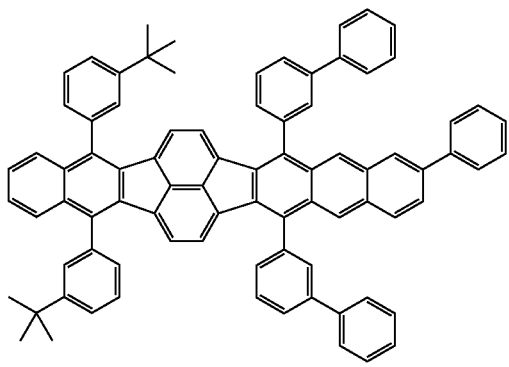
AG-14
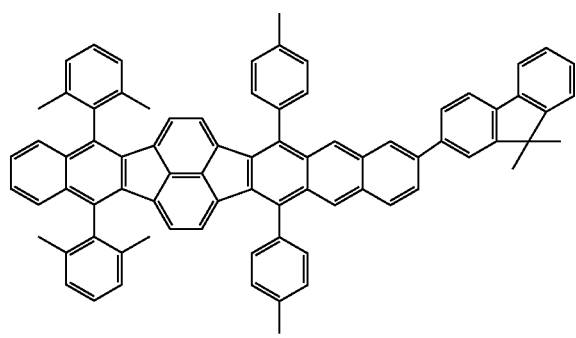
AG-15
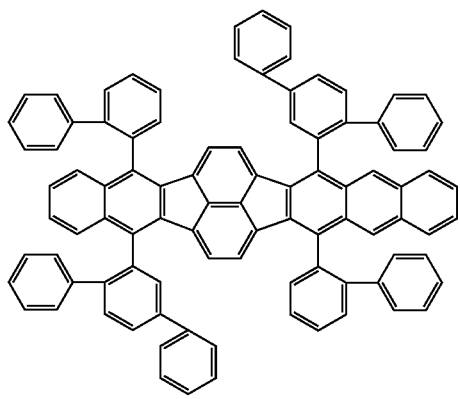
AG-16
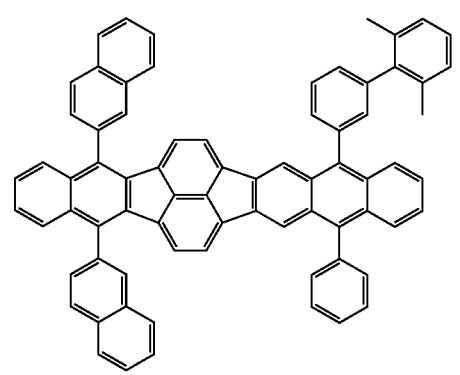
-continued
AG-17
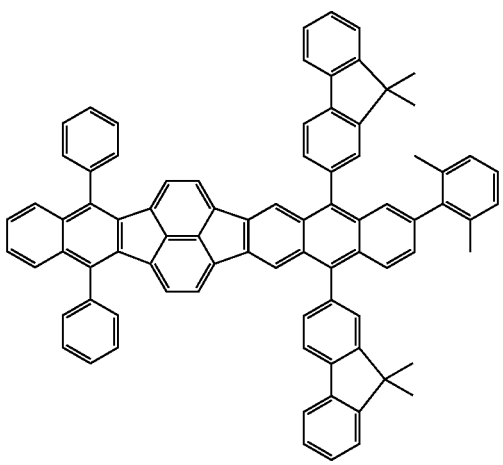
AG-18
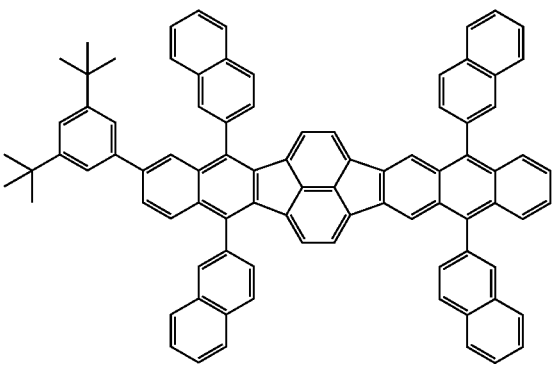
AG-19
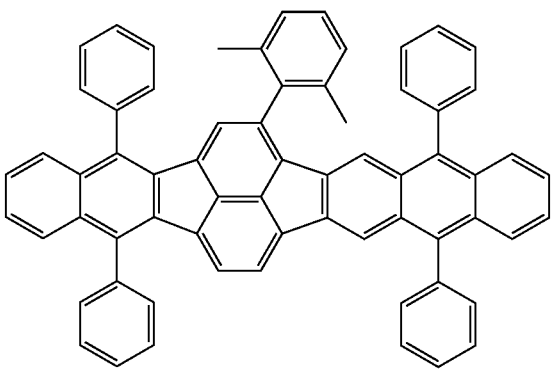
AG-20
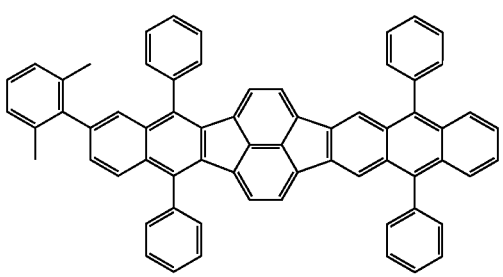

-continued
AG-21
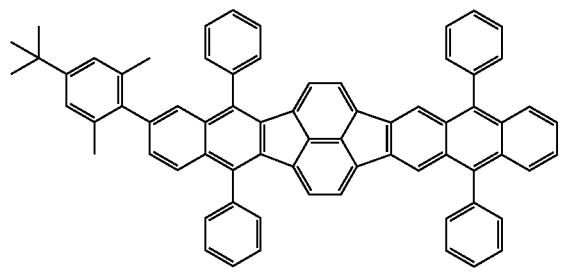
AG-22
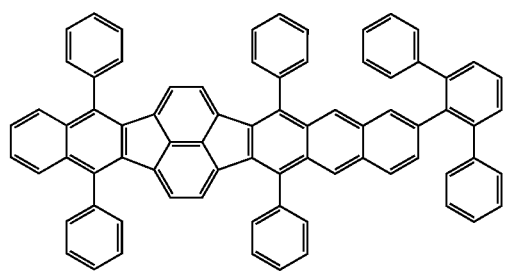
AG-23
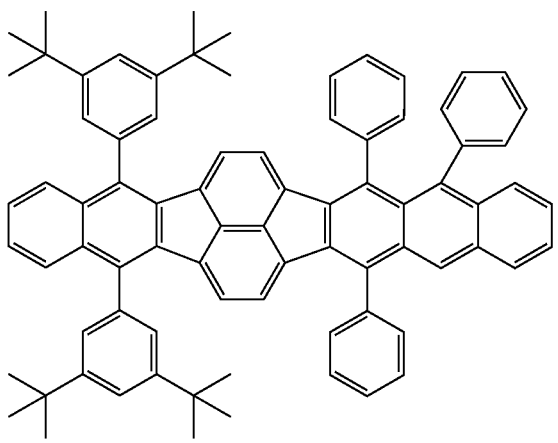
AG-24
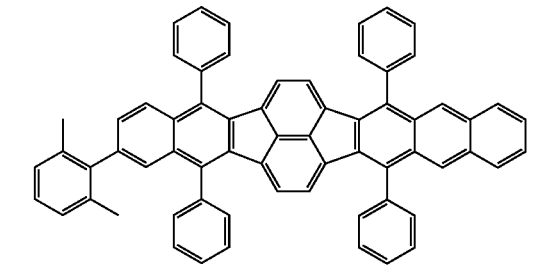
AG-25
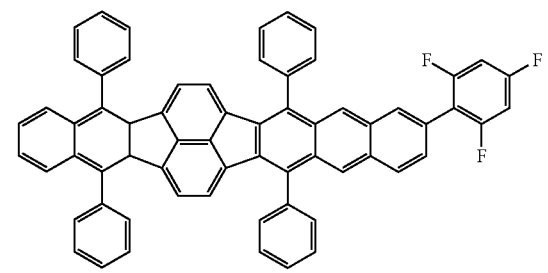
-continued
AG-26
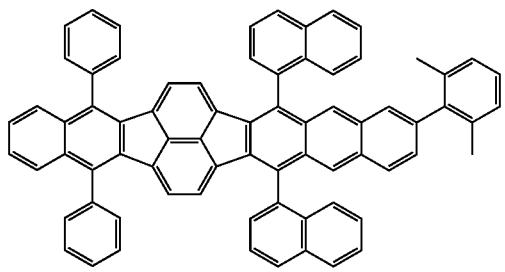
AG-27
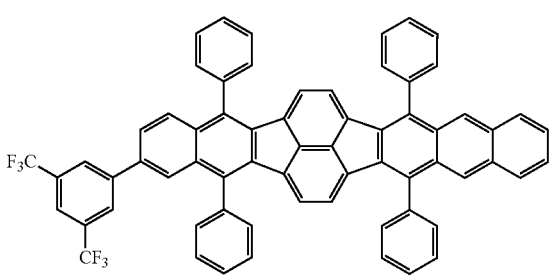
AG-28
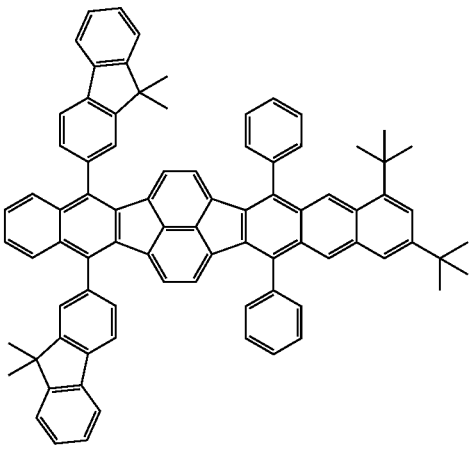
AG-29
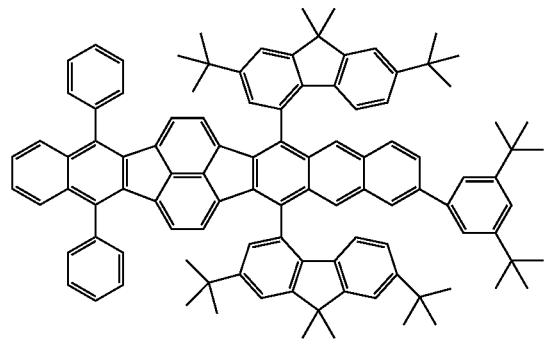

AG-30
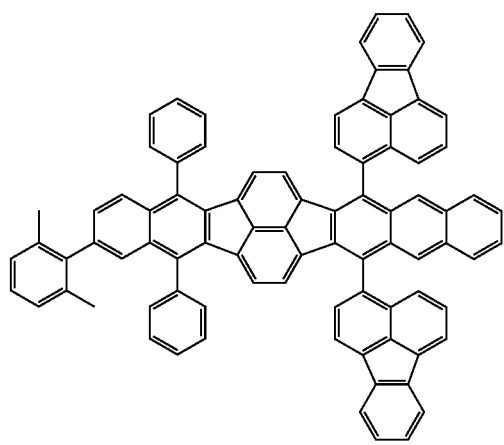
AH-1
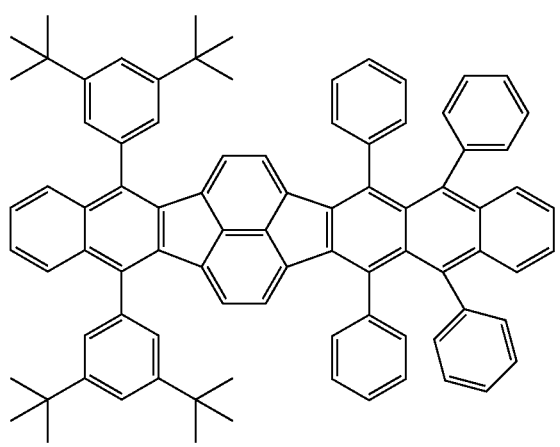
AH-2
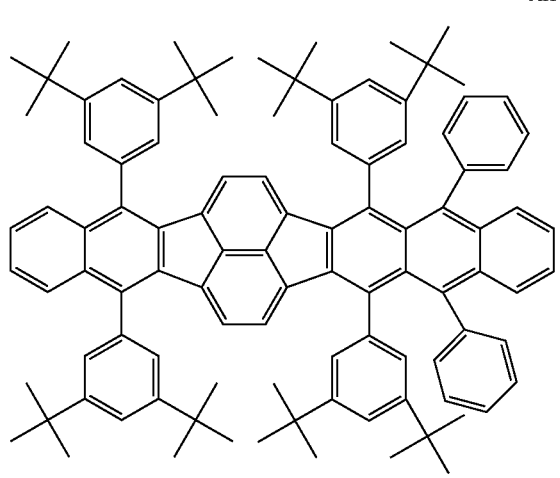
AH-3
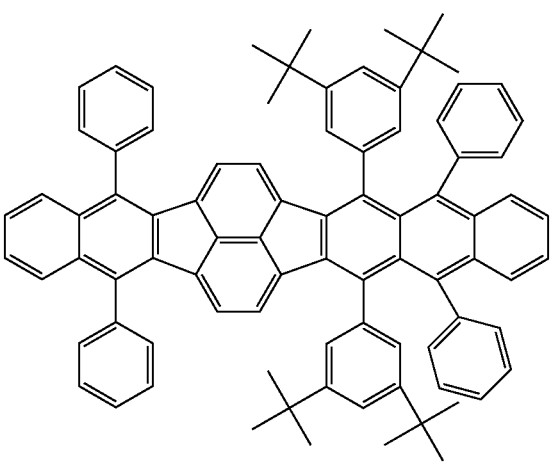
AH-4
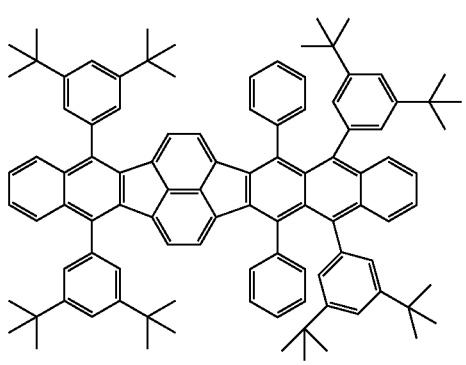
AH-5
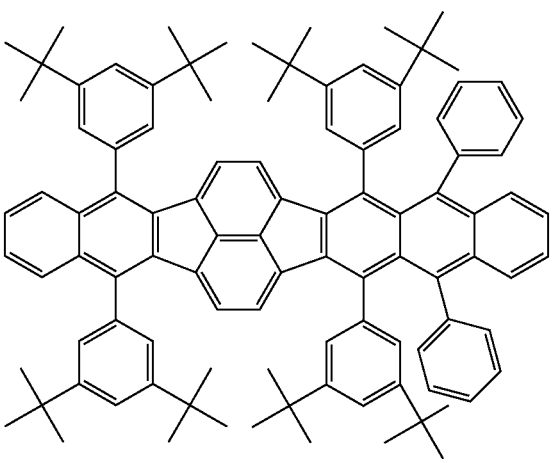
AH-6
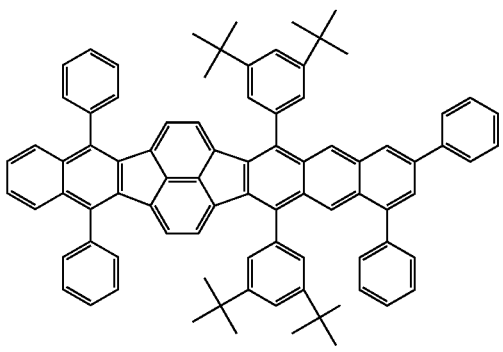

AH-7
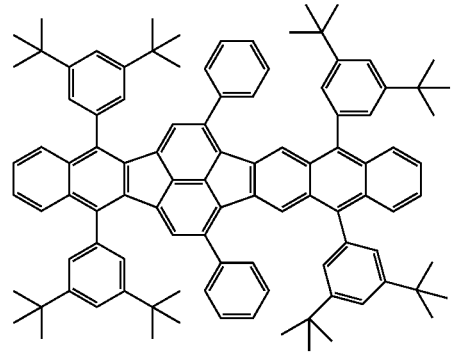
AH-8
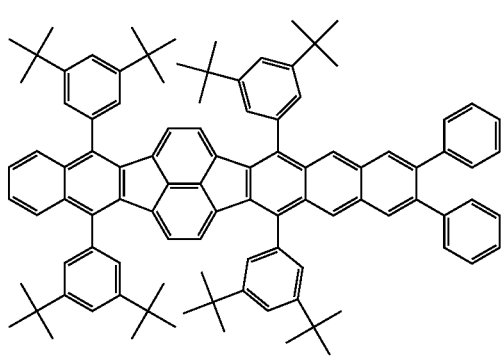
AH-9
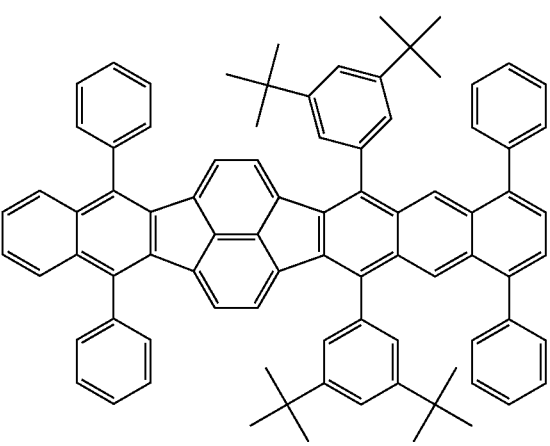
AH-10
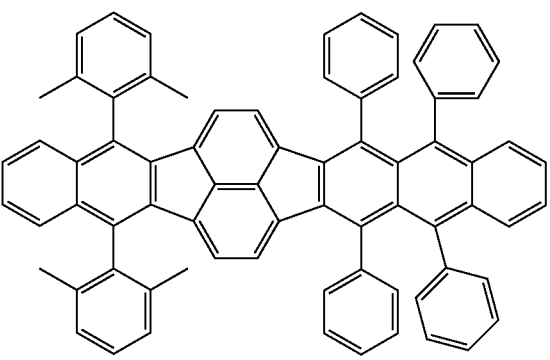
AH-11
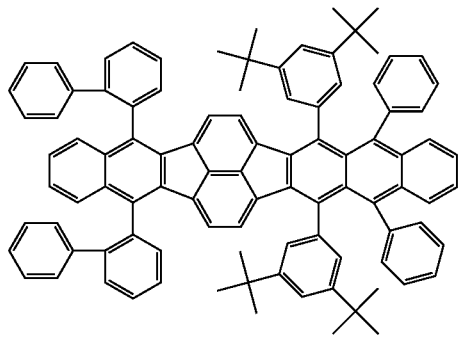
AH-12
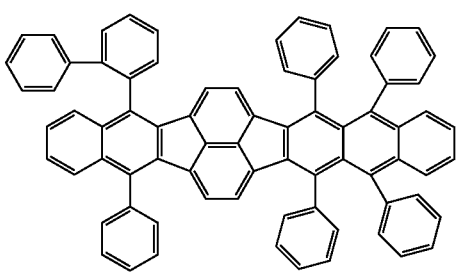
AH-13
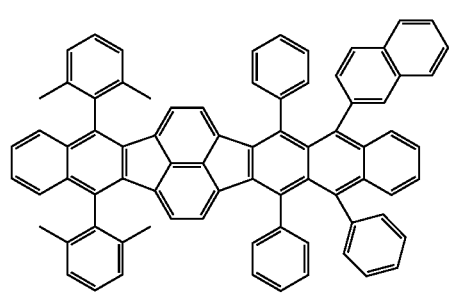
AH-14
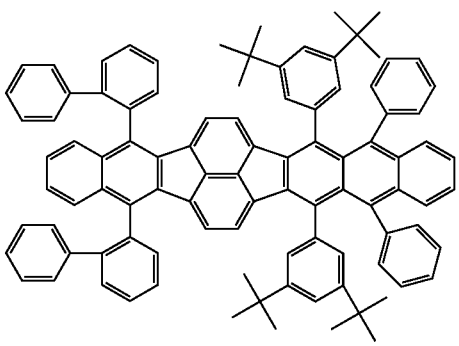
AH-15
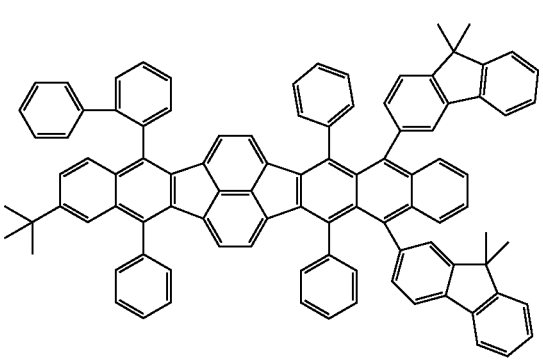

AI-1
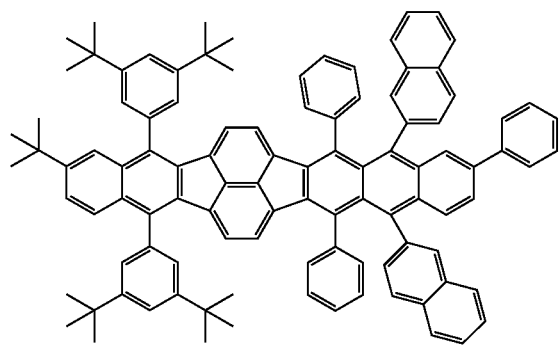
AK-1
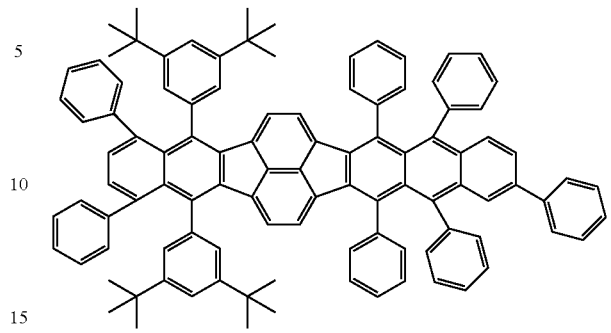
AK-2
AJ-1
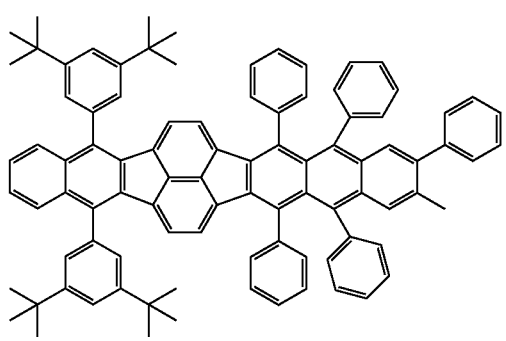
AL-1
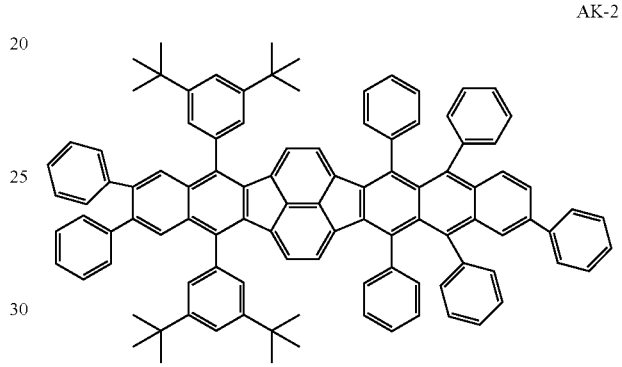
AJ-2
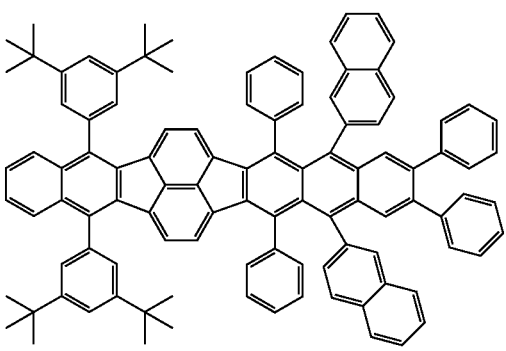
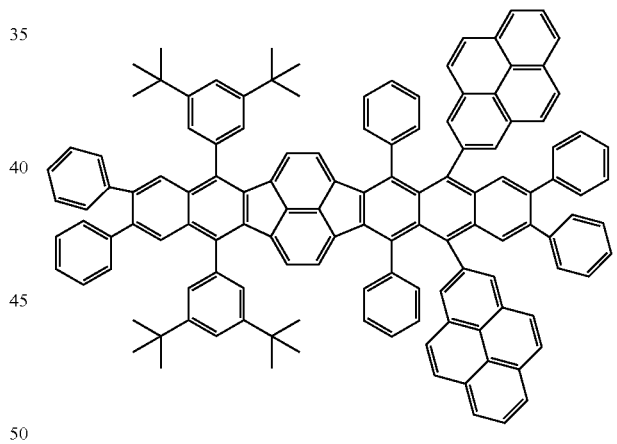
AL-2
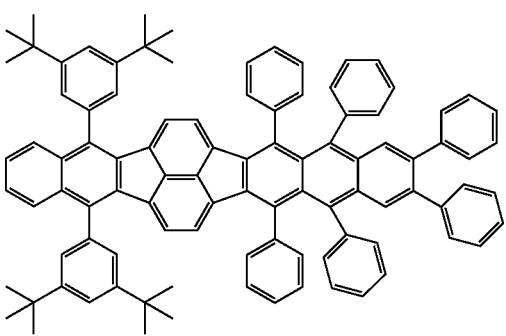
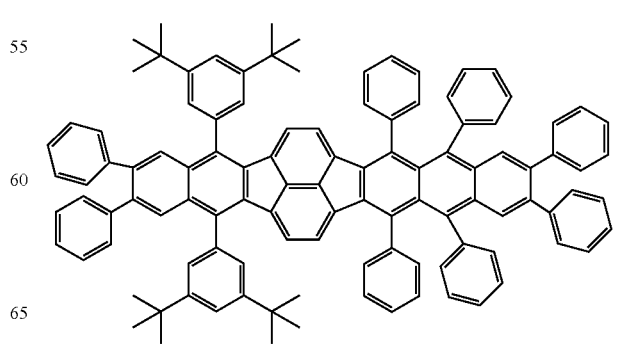

AM-1
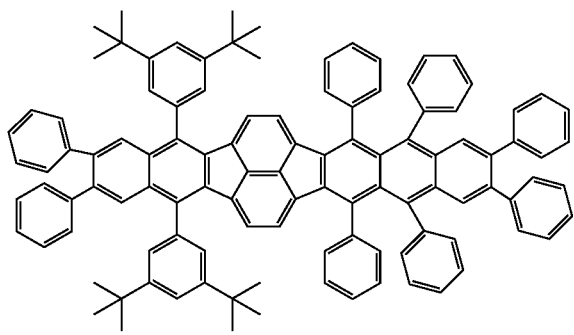
AQ-1
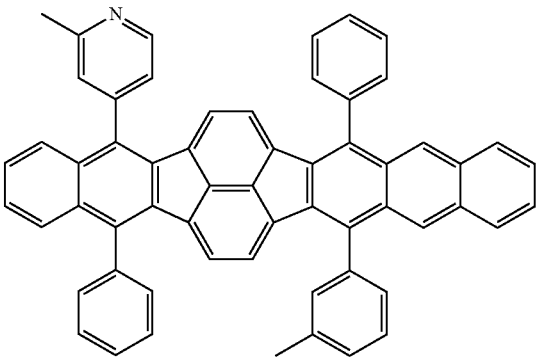
AN-1
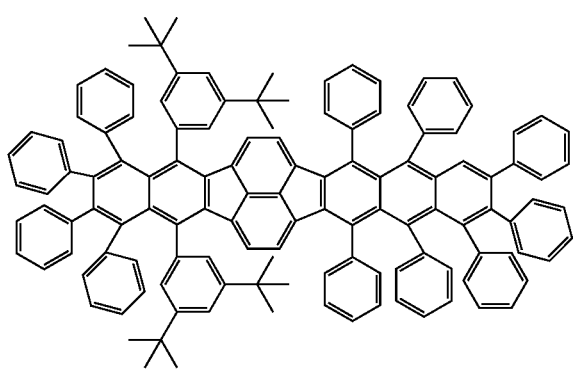
AQ-2
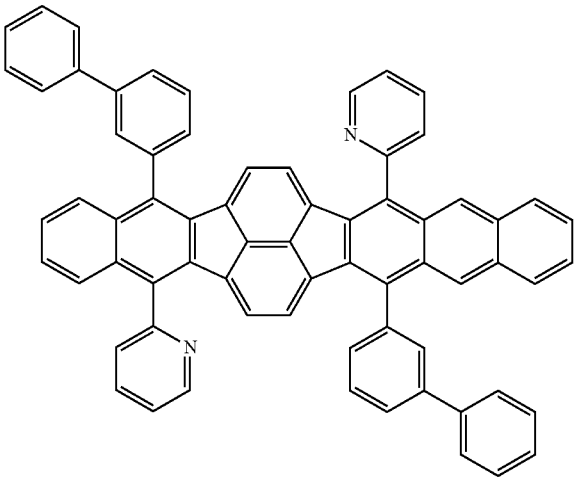
AO-1
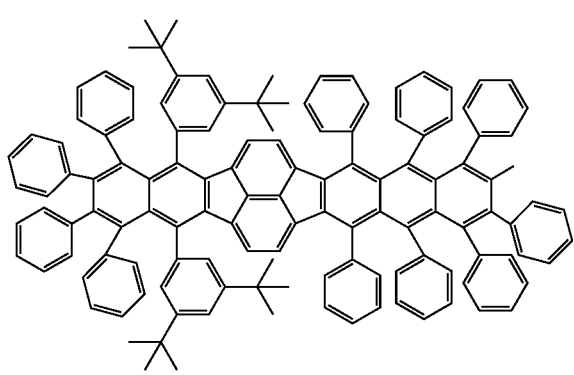
AP-1
AQ-3
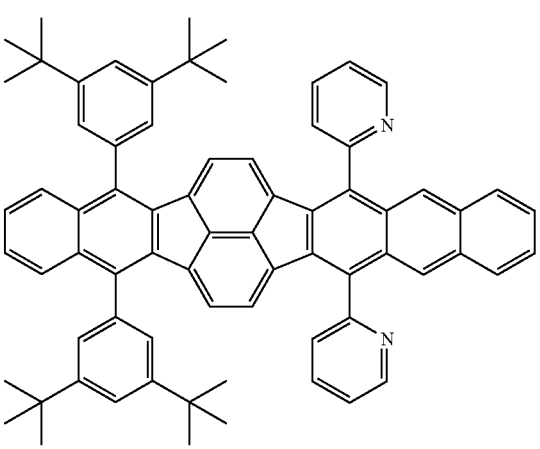

AQ-4
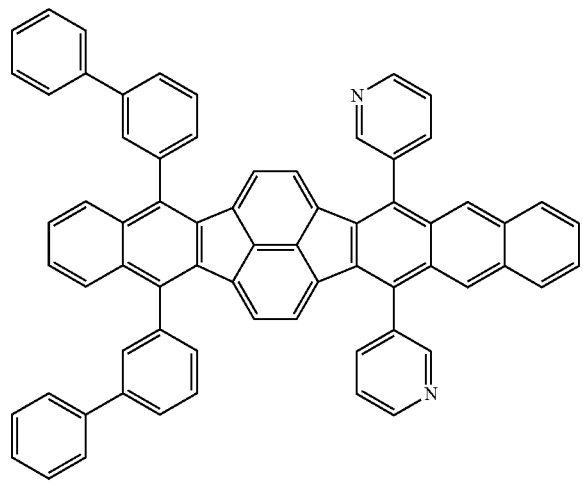
AQ-7
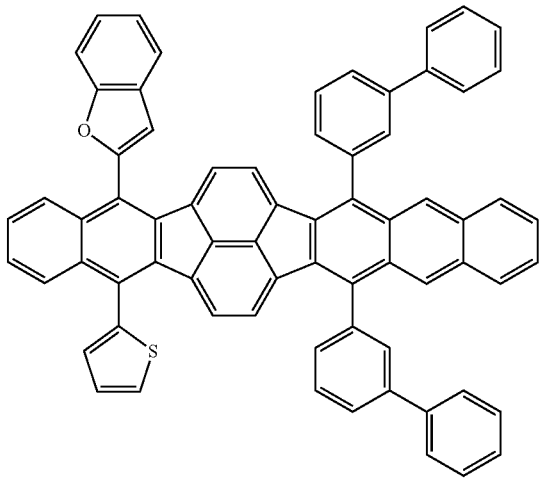
AQ-5
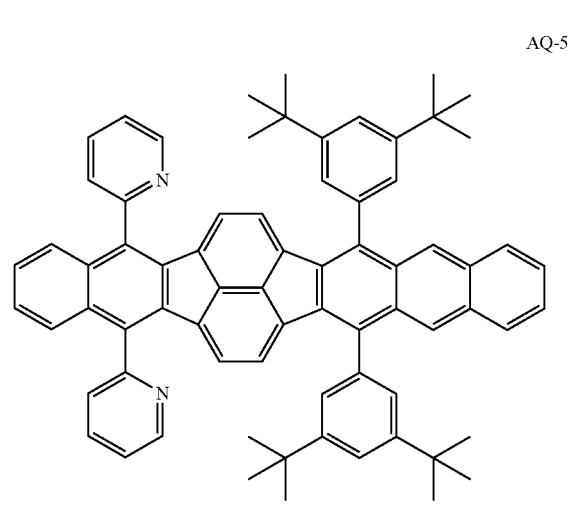
AQ-8
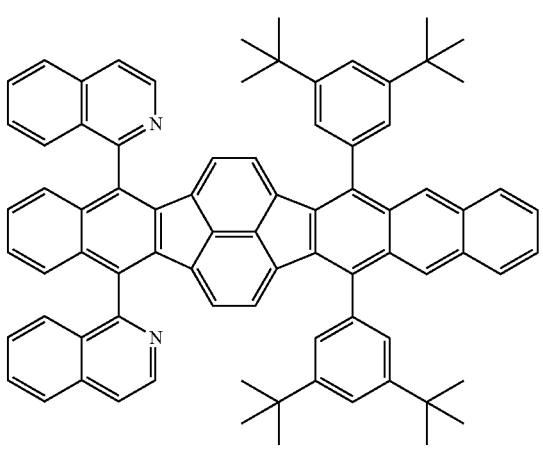
AQ-6
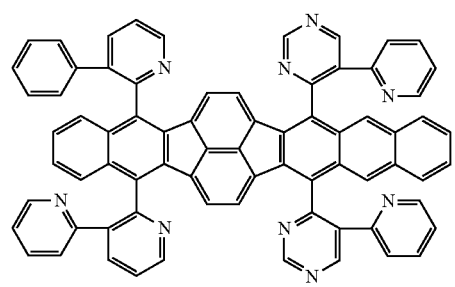
AQ-9
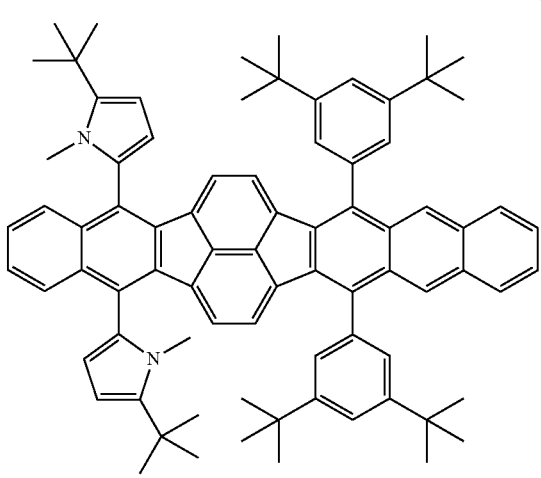

AQ-10
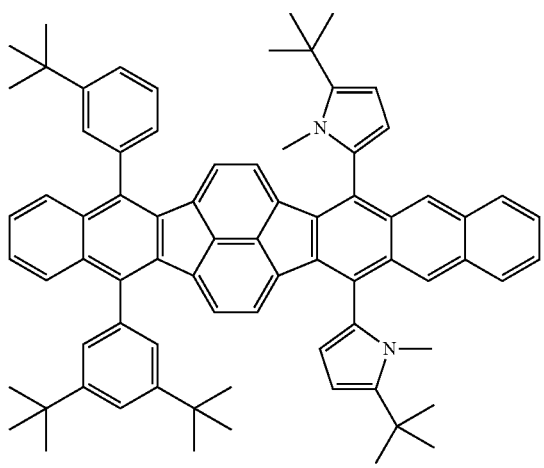
AQ-13
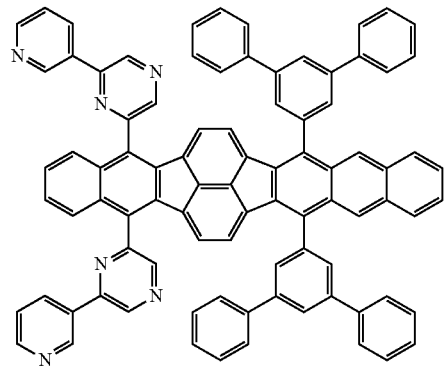
AQ-14
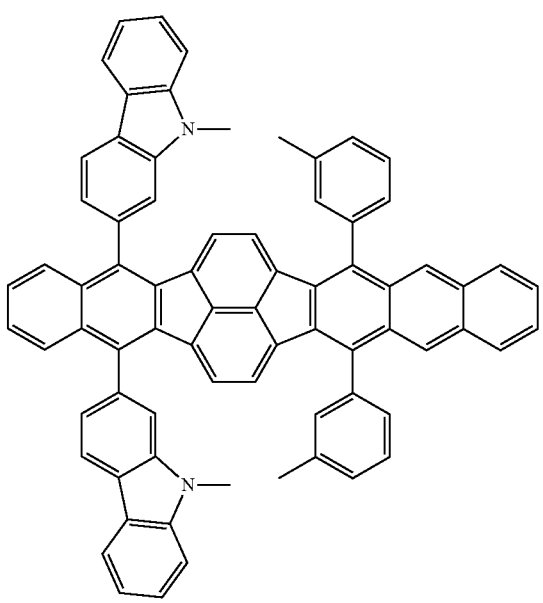
AQ-11
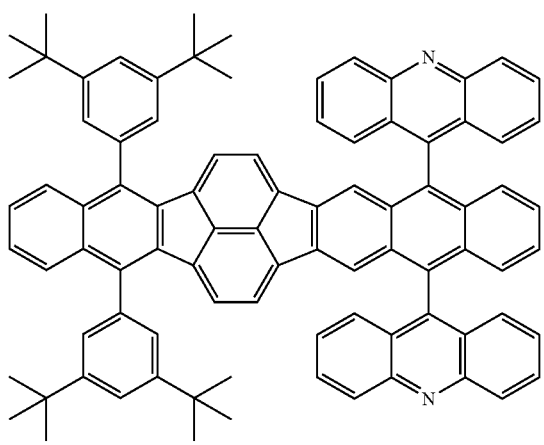
AQ-12
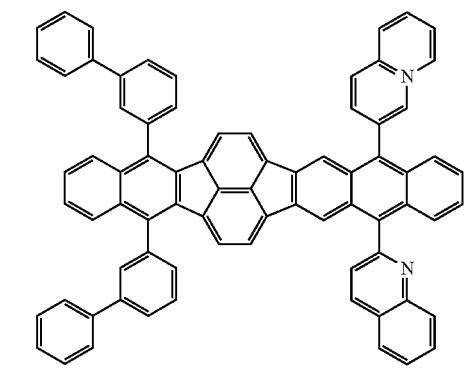
AQ-15
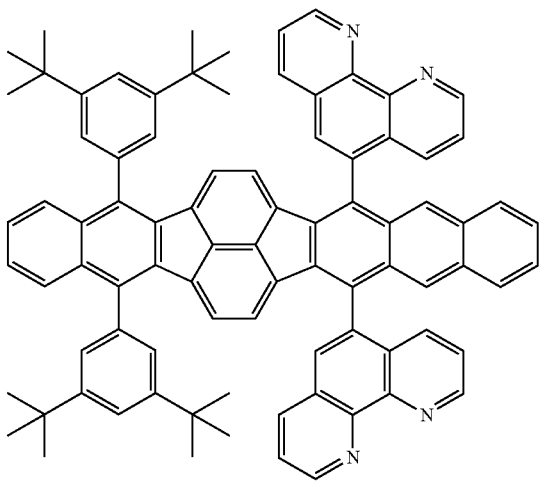

AR-1
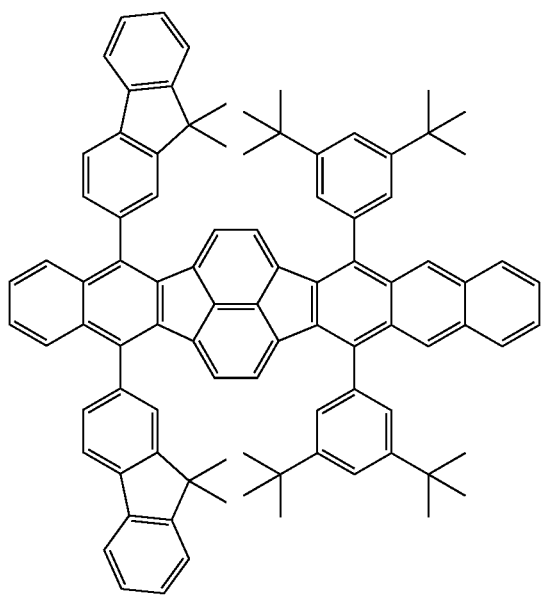
AR-2
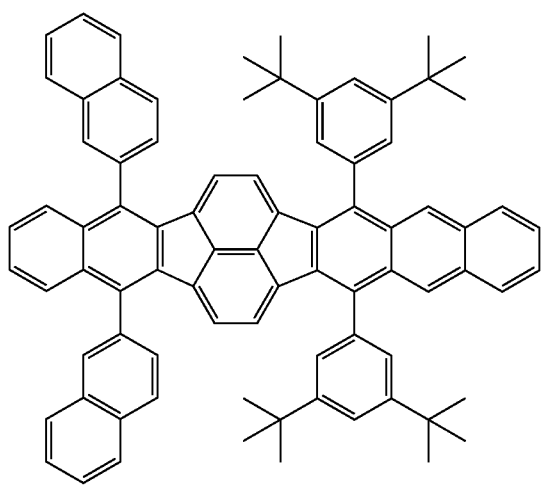
AR-3
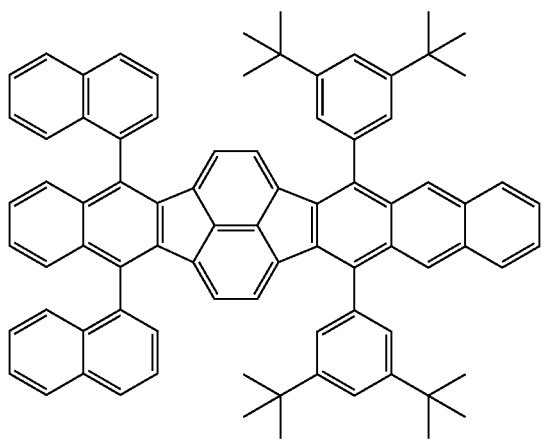
AR-4
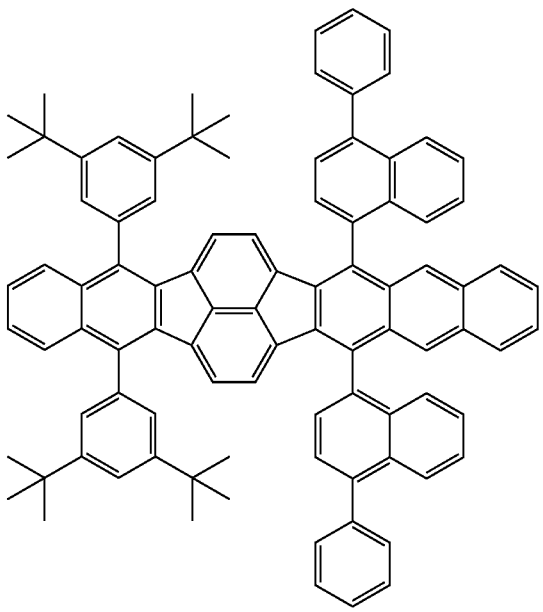
AR-5
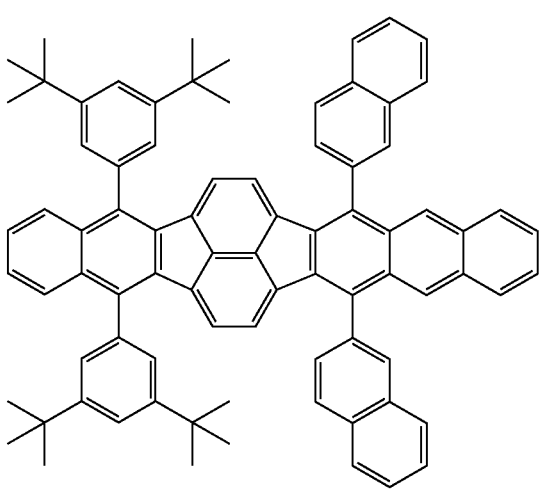

AR-6
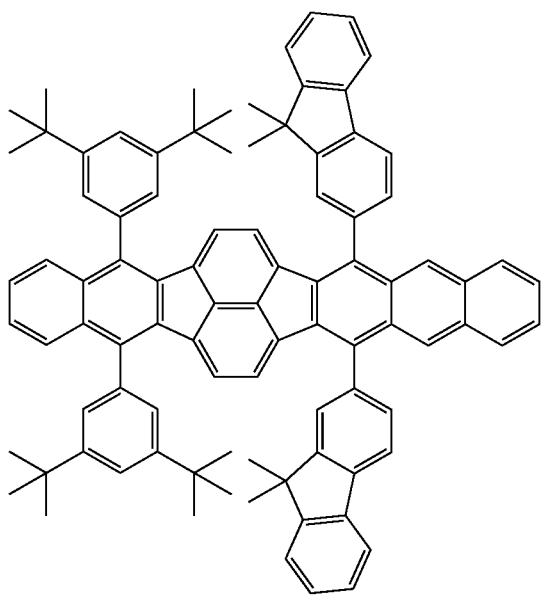
AR-9
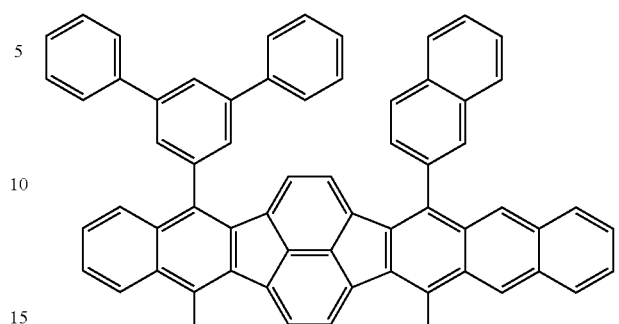
AR-7
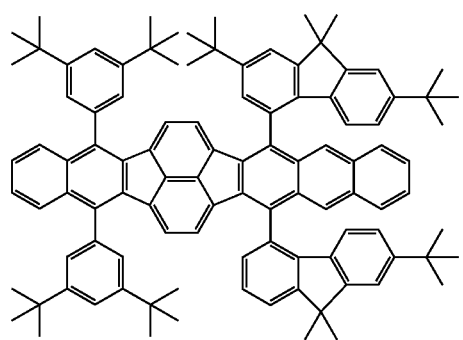
AR-10
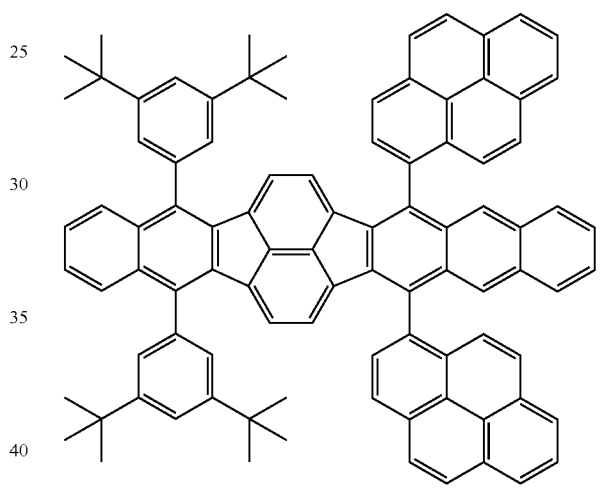
AR-8
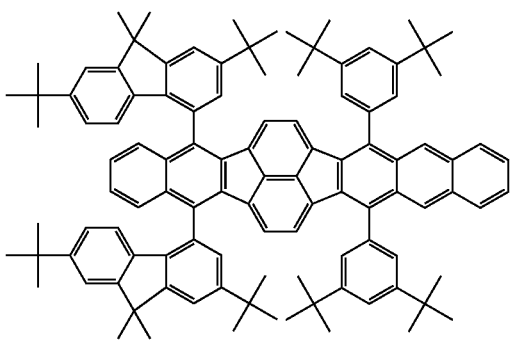
AR-11
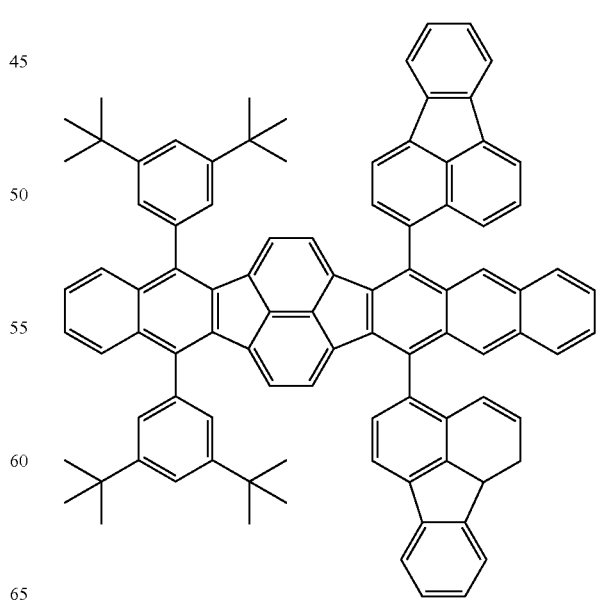

AR-12
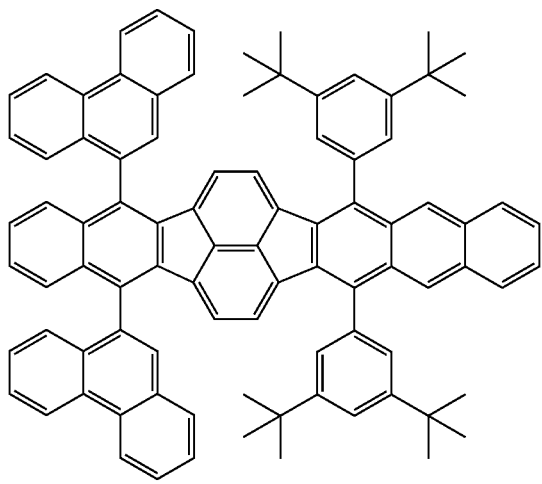
AR-15
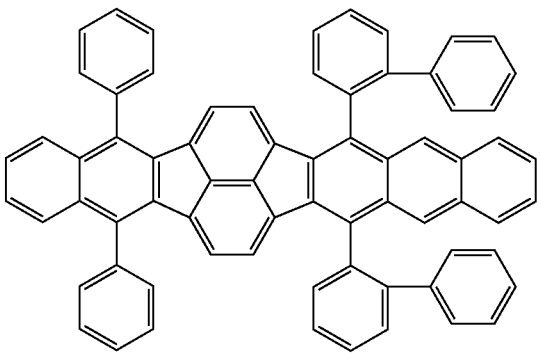
AR-13
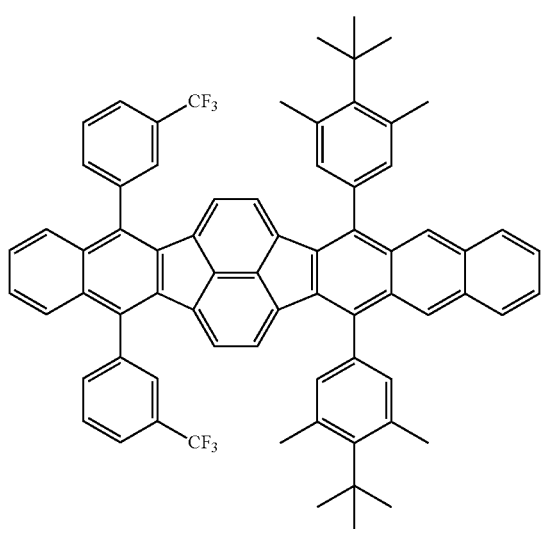
AR-25
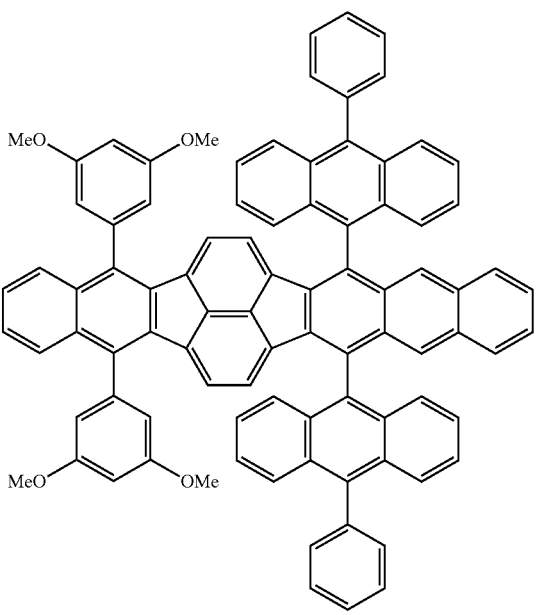
AR-14
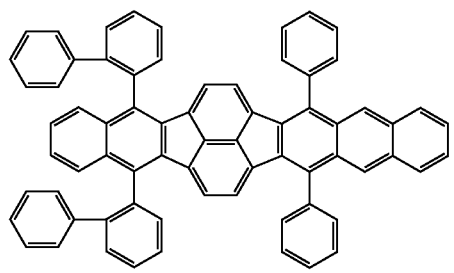
AR-26
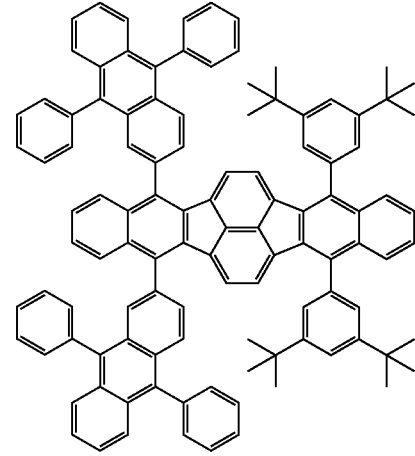

AR-27
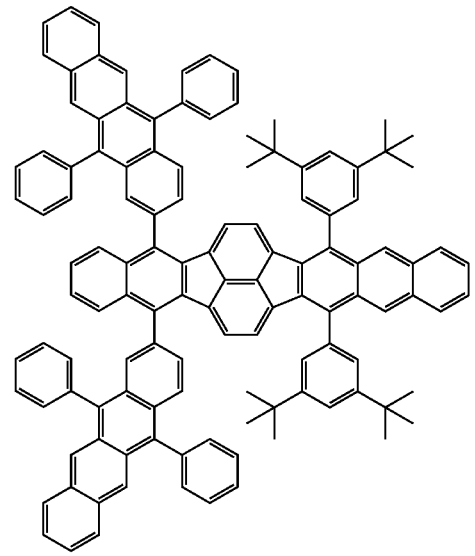
AR-16
AR-17
AR-18
AR-19
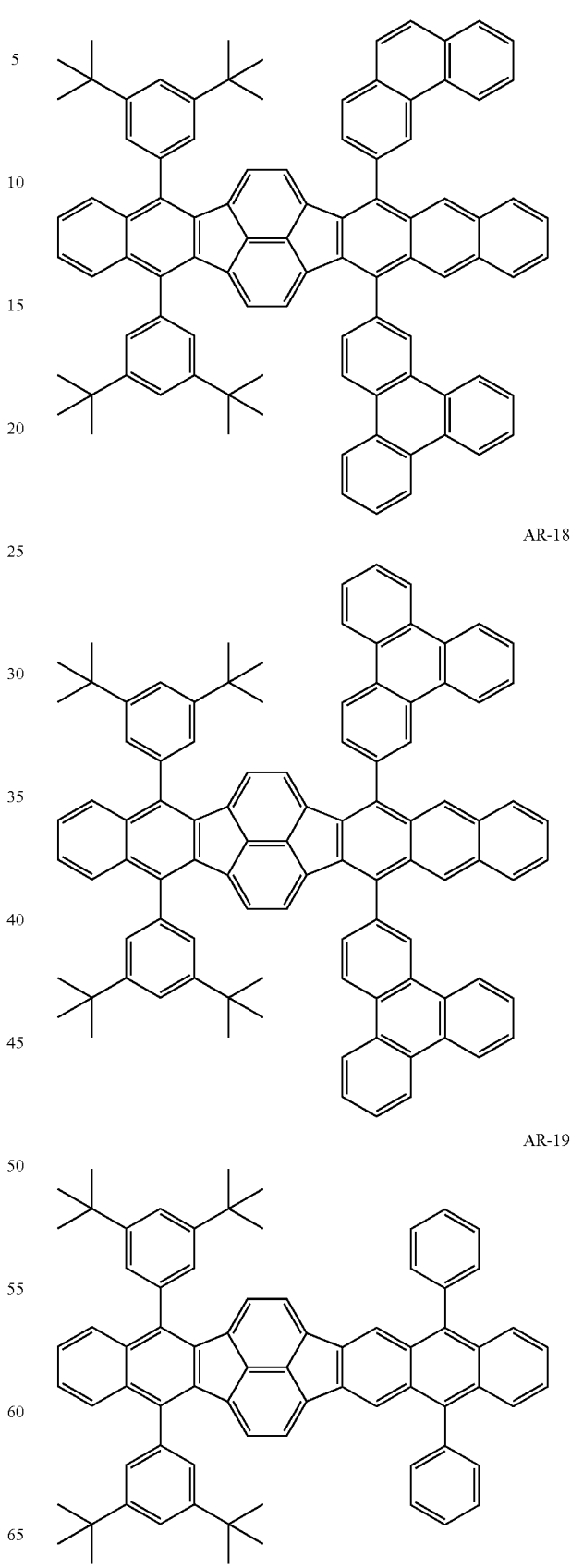

-continued

AR-20
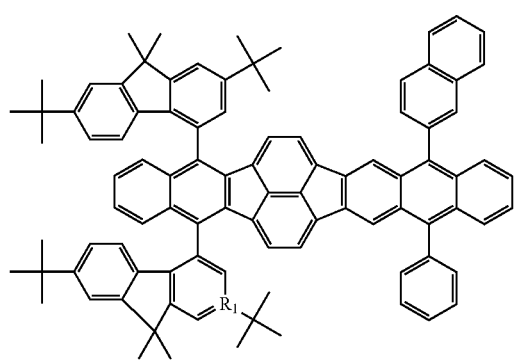

AR-21
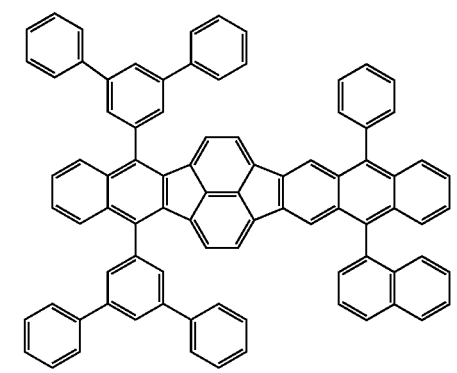

AR-22
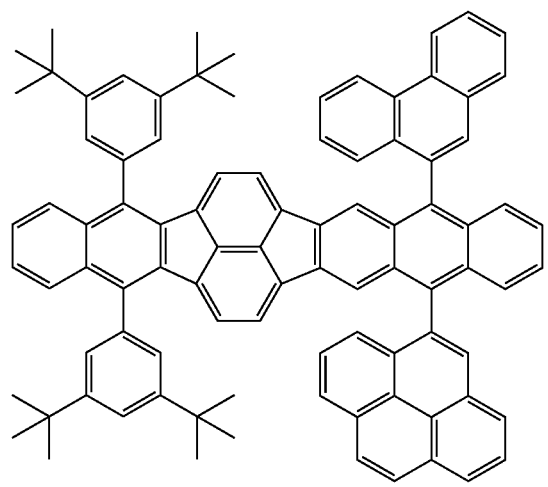

-continued

AR-23
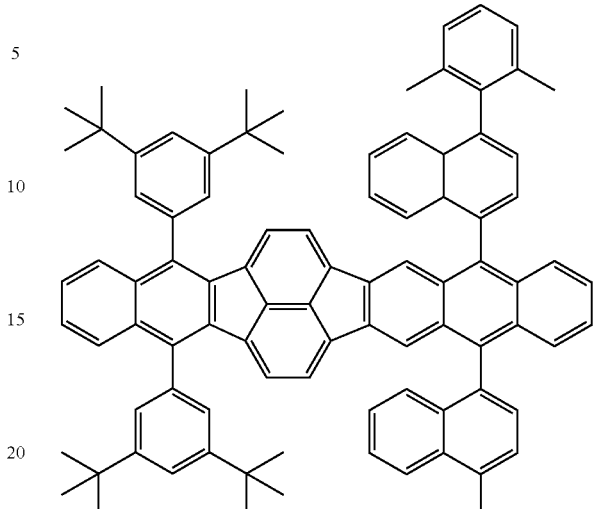

AR-24
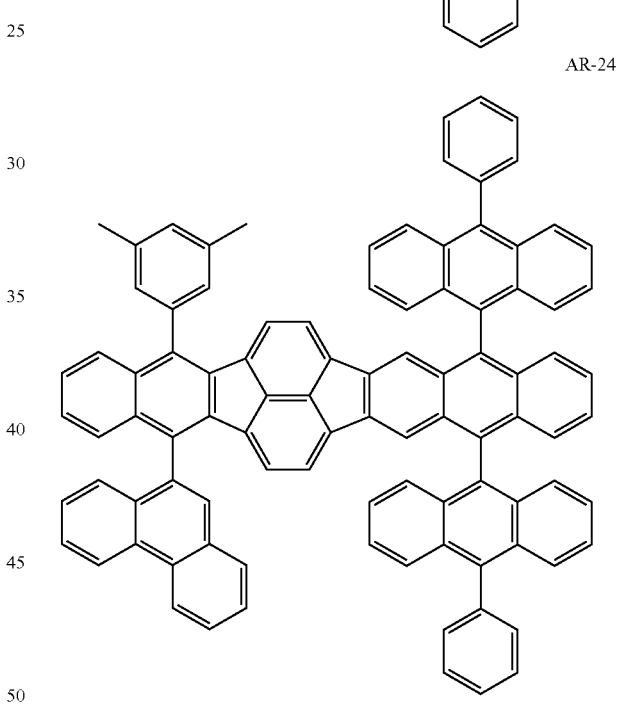

Next, the organic light-emitting device of the present invention will be described in detail.

The organic light-emitting device of the present invention is composed of an anode, a cathode and an organic compound layer which is interposed between the anode and the cathode. The organic light-emitting device of the present invention is preferably a device in which a voltage is applied between the anode and the cathode to emit light.

Herein below, with reference to the drawings, the organic light-emitting device of the present invention is explained in detail.

First, symbols included in the drawings are explained. Reference numeral 1 denotes a substrate, reference numeral 2 denotes an anode, reference numeral 3 denotes an emission layer, reference numeral 4 denotes a cathode, reference numeral 5 denotes a hole transport layer, reference numeral 6 denotes an electron transport layer, reference numeral 7 denotes a hole injection layer, reference numeral 8 denotes a hole/exciton blocking layer, and reference numerals 10, 20, 30, 40, 50 and 60 denote an organic light-emitting device.

Figure 2:
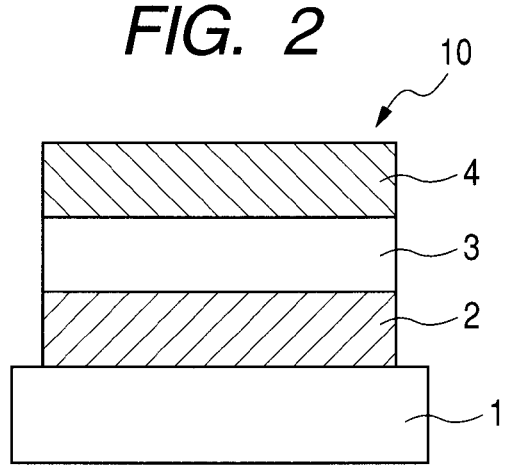
FIG. 2 is a cross-sectional view illustrating a first embodiment of the organic light-emitting device of the present invention.

FIG. 2 is a cross-sectional view showing a first embodiment of the organic light-emitting device of the present invention. In the organic light-emitting device 10 of FIG. 2, an anode 2, an emission layer 3 and a cathode 4 are sequentially formed on a substrate 1. This organic light-emitting device 10 is useful when the emission layer 3 is composed of an organic compound which has hole transporting property, electron transporting property and light-emitting property all together. In addition, it is also useful even for the case in which a mixture containing organic compounds each having any one of hole transporting property, electron transporting property and light-emitting property is used.

Figure 3:
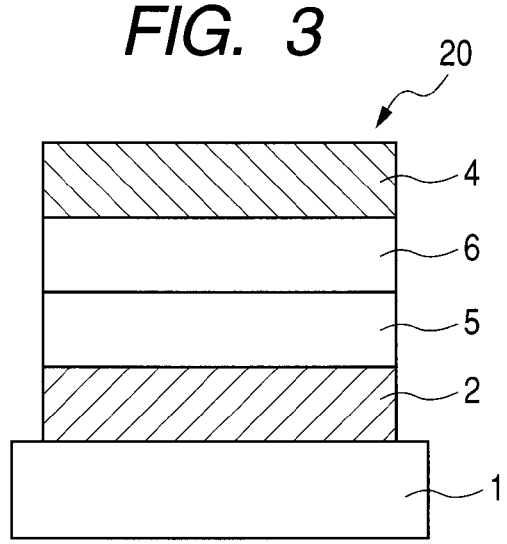
FIG. 3 is a cross-sectional view illustrating a second embodiment of the organic light-emitting device of the present invention.

FIG. 3 is a cross-sectional view showing a second embodiment of the organic light-emitting device of the present invention. In the organic light-emitting device 20 of FIG. 3, an anode 2, a hole transport layer 5, and an electron transport layer 6 and a cathode 4 are sequentially formed on a substrate 1. This organic light-emitting device 20 is useful when a light-emitting organic compound which has any one of hole transporting property and electron transporting property is used in combination with an organic compound which has either electron transporting property or hole transporting property. In addition, in this organic light-emitting device 20, the hole transport layer 5 or the electron transport layer 6 also serves as an emission layer.

Figure 4:
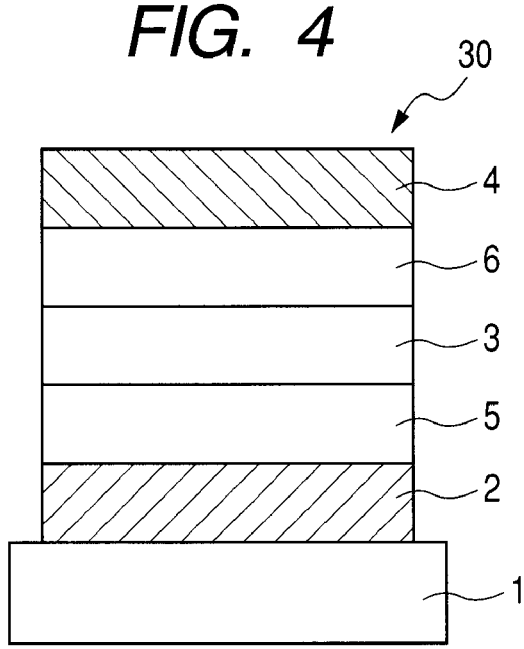
FIG. 4 is a cross-sectional view illustrating a third embodiment of the organic light-emitting device of the present invention.

FIG. 4 is a cross-sectional view showing a third embodiment of the organic light-emitting device of the present invention. In the organic light-emitting device 30 of FIG. 4, an emission layer 3 is additionally provided between the hole transport layer 5 and the electron transport layer 6 of the organic light-emitting device 20 of FIG. 3. In this organic light-emitting device 30, carrier transport and light emission are separated from each other, and it is used in an appropriate combination with organic compounds which have hole transporting property, electron transporting property and light-emitting property. Thus, the freedom in selecting the material is remarkably increased and at the same time various kinds of organic compounds having different emission wavelengths can be used, and diversification of the emission hue can be realized. Furthermore, with effective confinement of carriers or excitons within the emission layer 3 at a central region, the emission efficiency of the organic light-emitting device 30 can be also improved.

Figure 5:
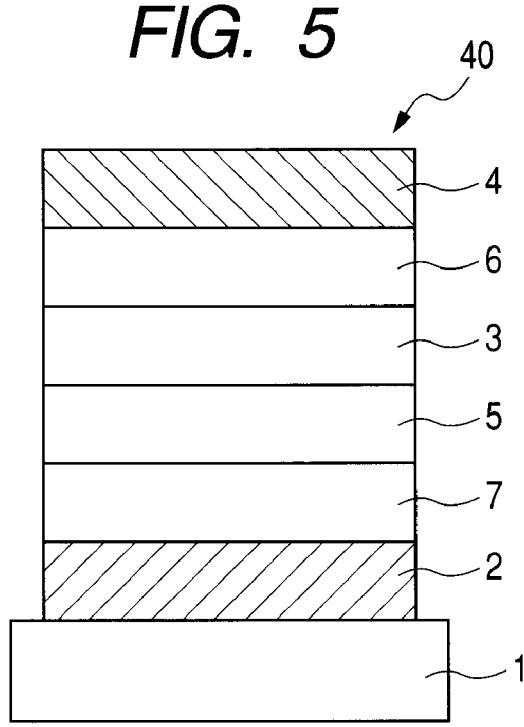
FIG. 5 is a cross-sectional view illustrating a fourth embodiment of the organic light-emitting device of the present invention.

FIG. 5 is a cross-sectional view showing the fourth embodiment of the organic light-emitting device of the present invention. In the organic light-emitting device 40 of FIG. 5, a hole injection layer 7 is additionally provided between the anode 2 and the hole transport layer 5 of the organic light-emitting device 30 of FIG. 4. In the organic light-emitting device 40, by additionally providing the hole injection layer 7, the adhesiveness between the anode 2 and the hole transport layer 5 or the hole injectability is improved, and the drive voltage can be effectively lowered.

Figure 6:
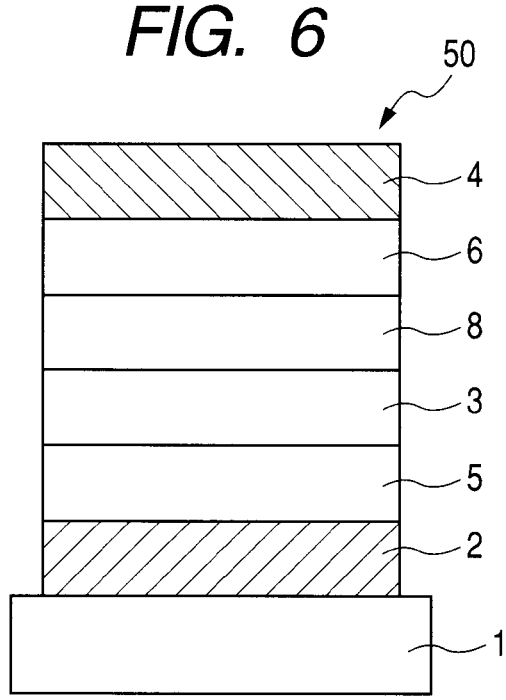
FIG. 6 is a cross-sectional view illustrating a fifth embodiment of the organic light-emitting device of the present invention.

FIG. 6 is a cross-sectional view showing a fifth embodiment of the organic light-emitting device of the present invention. In the organic light-emitting device 50 of FIG. 6, a layer (hole/exciton blocking layer 8) which inhibits leakage of holes or excitons to the cathode 4 side is additionally provided between the emission layer 3 and the electron transport layer 6 of the organic light-emitting device 30 of FIG. 4. When an organic compound having a very high ionization potential is used as the hole/exciton blocking layer 8, the emission efficiency of the organic light-emitting device 50 can be effectively improved.

Figure 7:
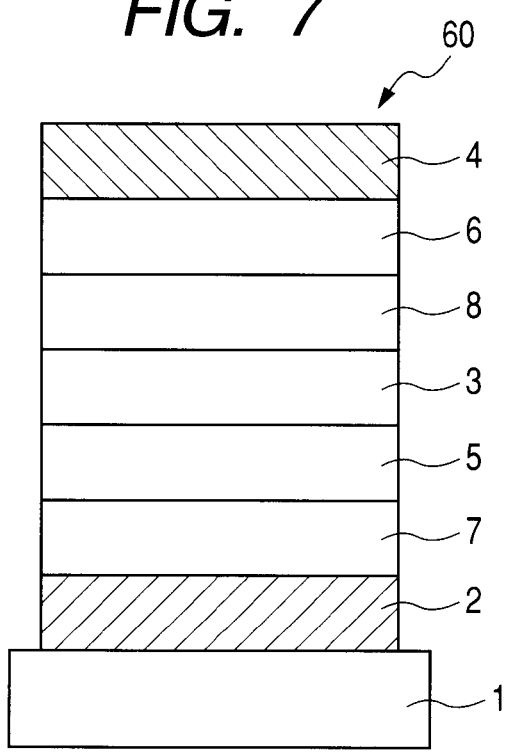

FIG. 7 is a cross-sectional view illustrating a sixth embodiment of the organic light-emitting device of the present invention. The organic light-emitting device 60 illustrated in FIG. 7 is different from the organic light-emitting device 40 illustrated in FIG. 5 in that the hole/exciton-blocking layer 8 is additionally provided between the emission layer 3 and the electron transport layer 6. The use of an organic compound having an extremely high ionization potential as the hole/exciton blocking layer 8 improves the emission efficiency of the organic light-emitting device 60.

It should be noted that the device constitutions illustrated in FIGS. 2 through 7 are merely very basic constitutions, and the constitution of the organic light-emitting device containing the fused polycyclic compound of the present invention is not limited to those constitutions. For example, an insulating layer, an adhesive layer, or an interference layer may be provided at an interface between an electrode and an organic layer. Furthermore, a hole transport layer 5 may be composed of two layers having different ionization potentials.

The fused polycyclic compound of the present invention can be used in any one of the embodiments illustrated in FIGS. 2 to 7. At that time, the fused polycyclic compound of the present invention may be used alone, or multiple compounds may be used in combination.

The fused polycyclic compound of the present invention can be used as a material for forming a layer formed of an organic compound such as any one of the emission layer 3, the hole transport layer 5, the electron transport layer 6, the hole injection layer 7, and the hole/exciton blocking layer 8 illustrated in FIGS. 2 to 7. At that time, each layer may be formed of one kind of the fused polycyclic compound, or may be formed of a combination of two or more kinds of the fused polycyclic compounds.

The fused polycyclic compound of the present invention is preferably contained in the emission layer 3. Here, the emission layer 3 may be formed of only the fused polycyclic compound of the present invention and is preferably formed of a host and a guest. In the case where the emission layer 3 is formed of a host and a guest, the host may be the fused polycyclic compound of the present invention, and preferably, the guest is the fused polycyclic compound of the present invention.

When the fused polycyclic compound of the present invention is used as a host for the emission layer 3, the light-emitting material as a guest is not particularly limited, but is preferably a fluorescent material. In addition, when the fused polycyclic compound of the present invention is used as a host for the emission layer 3, the content of the compound is preferably 50 wt % or more to 99.9 wt % or less, or more preferably 80 wt % or more to 99.9 wt % or less with respect to the entirety of the materials which constitutes the emission layer 3.

When the fused polycyclic compound of the present invention is used as a guest (light-emitting material) for the emission layer 3, the content of the compound is preferably 0.1 wt % or more to 50 wt % or less, or more preferably 0.1 wt % or more to 20 wt % or less with respect to the entirety of the materials which constitutes the emission layer 3.

The compound of the present invention represented by the general formula [1] can be used in any layer in the organic light-emitting device, and the compound can also be used together with, for example, a conventionally known hole transporting material, matrix material, light-emitting material, or electron transporting material as needed.

Examples of those compounds are enumerated below. However, the present invention is not limited to the examples.

Hole Transporting Material
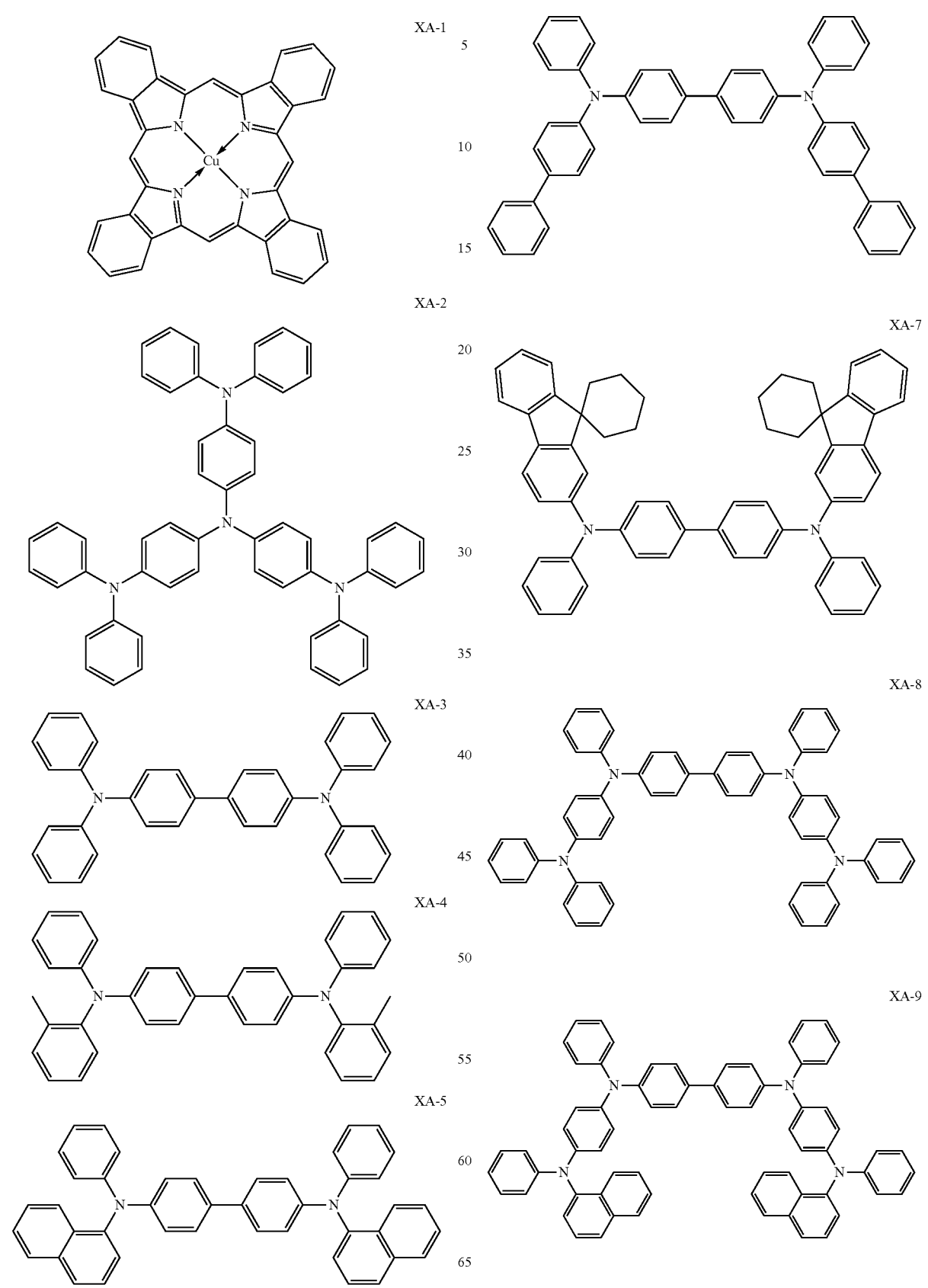

XA-10
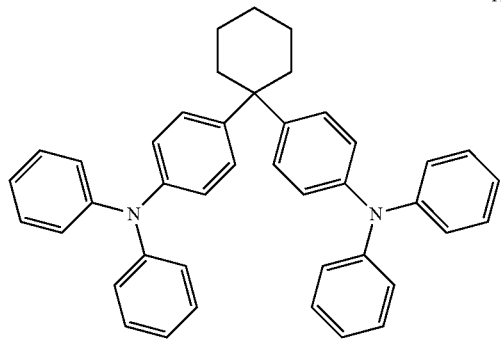
XB-2
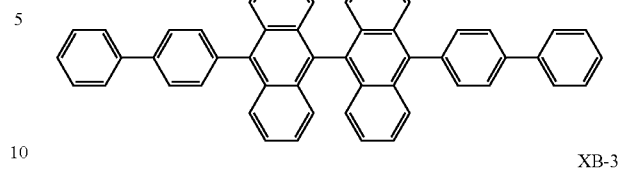
XB-3
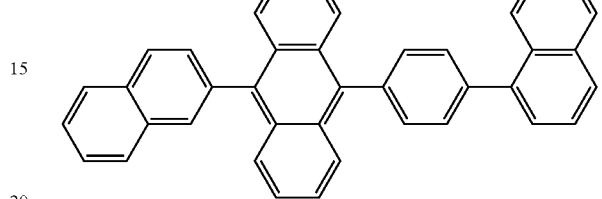
XA-11
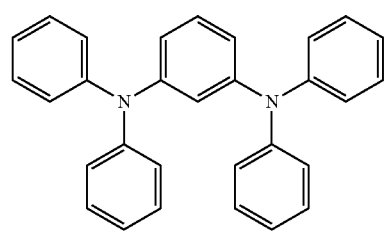
XB-4
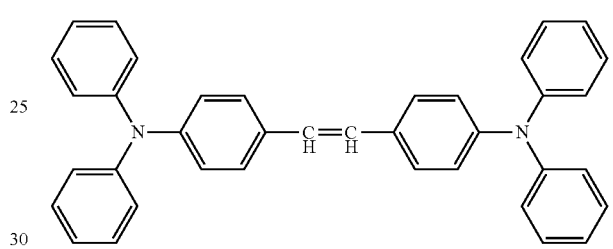
XA-12
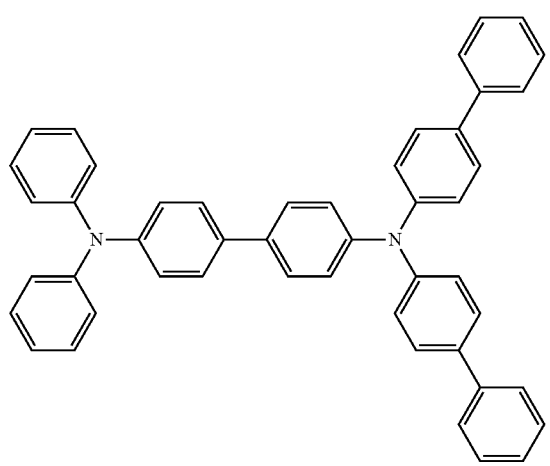
XB-5
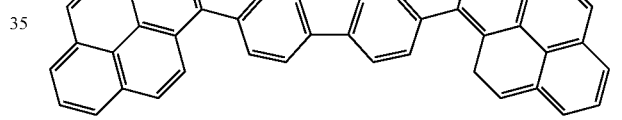
XB-6
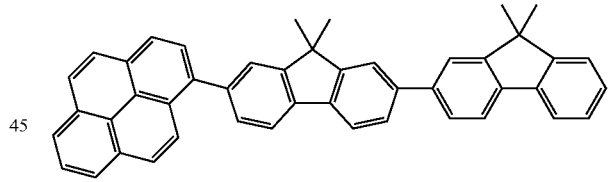
Matrix Material
XB-7
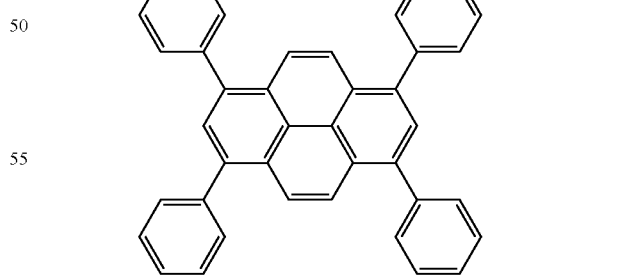
XB-1
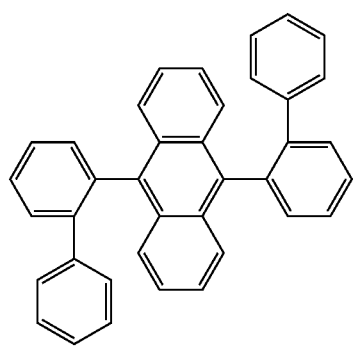
XB-8
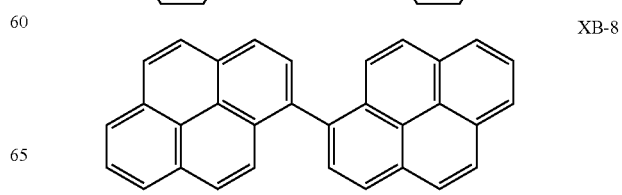

-continued
Light Emitting Material
XB-9
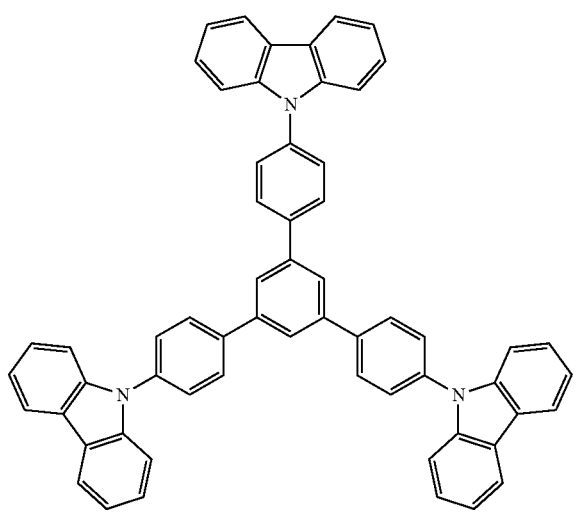
XC-1
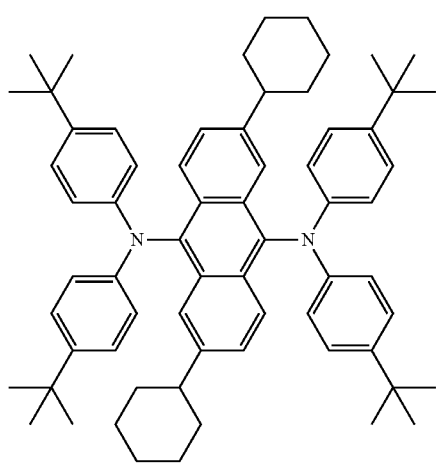
XB-10
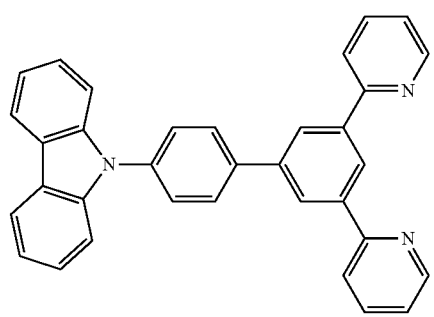
XC-2
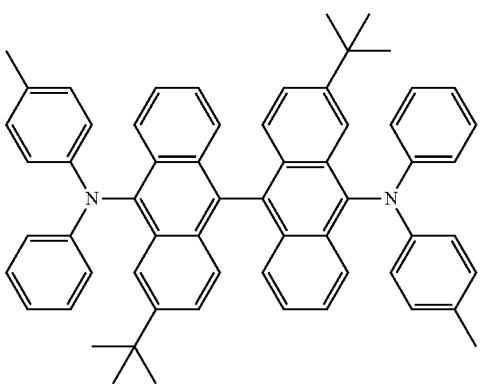
XB-11
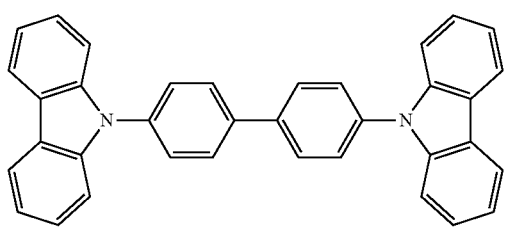
XC-3
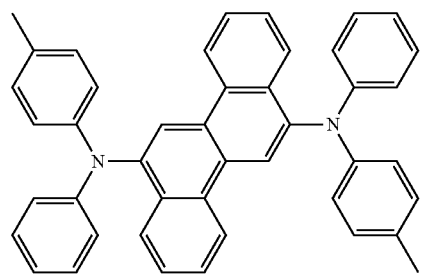
XB-12
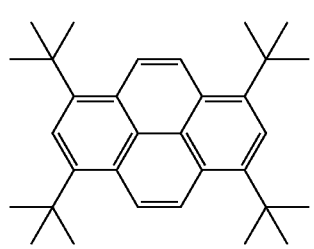
XC-4
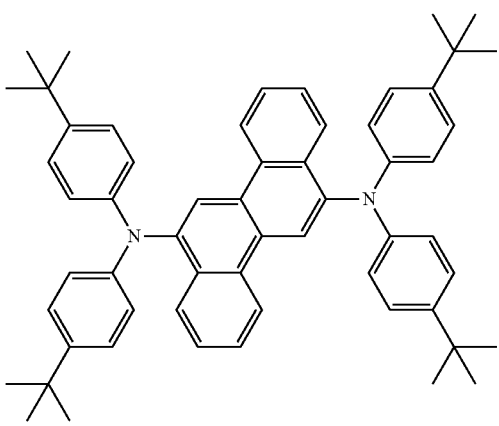

XC-5
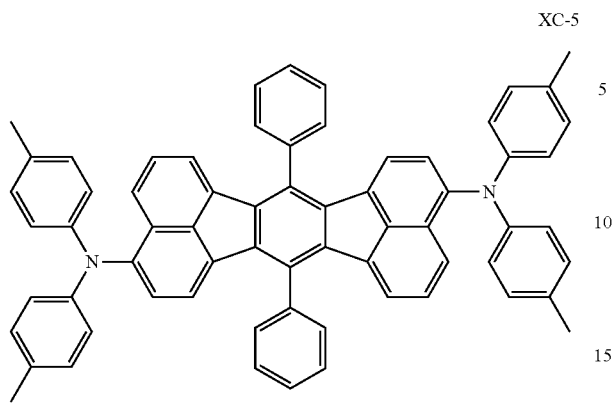
XC-6
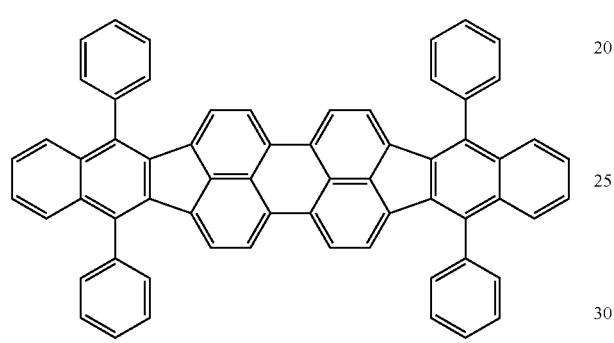
XC-7
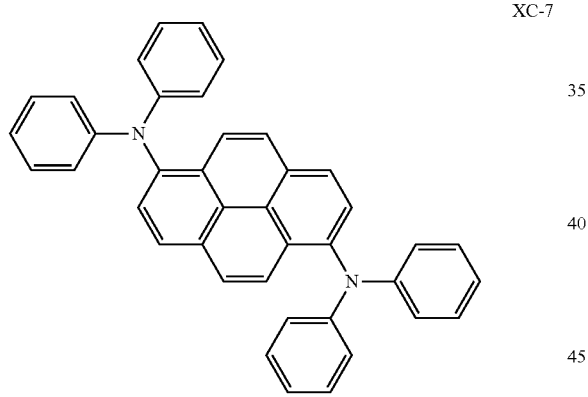
XC-8
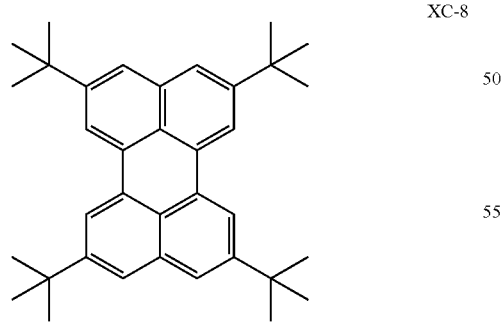
XC-9
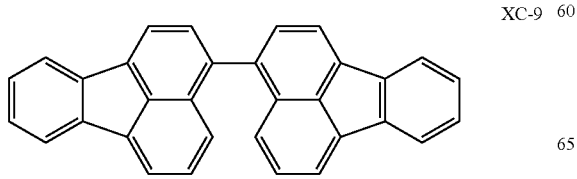
XC-10
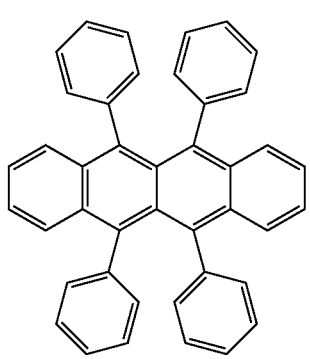
XC-11
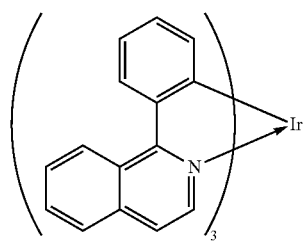
XC-12
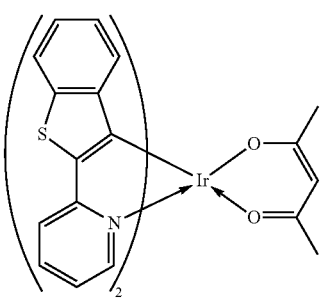
Electron Transporting Material
XD-1
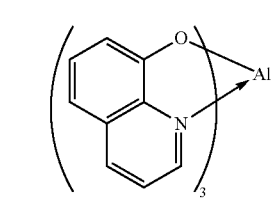
XD-2
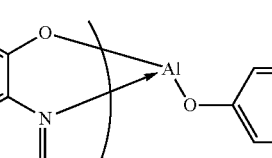
XD-3
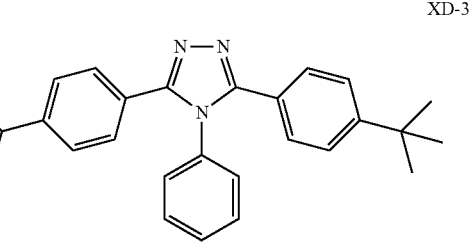

XD-4

XD-5

XD-6

Polymer Material

XE-1

XE-2

XE-3

XE-4

R: $C_6H_{13}$, $C_8H_{17}$, $C_{12}H_{25}$

XE-5

XE-6

XE-7

XE-8

XE-9

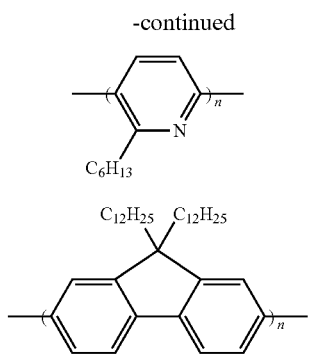

XE-10

XE-11

An anode material used in the organic light-emitting device of the present invention preferably has as large a work function as possible. Examples of the anode material that can be used include: metal elements such as gold, platinum, nickel, palladium, cobalt, selenium, and vanadium, and alloys thereof; and metal oxides such as tin oxide, zinc oxide, indium tin oxide (ITO), and indium zinc oxide. In addition, a conductive polymer such as polyaniline, polypyrrole, polythiophene, and polyphenylene sulfide can also be used. Each of those electrode substances may be used alone, or a plurality of the substances may be used in combination.

On the other hand, a cathode material used in the organic light-emitting device of the present invention preferably has a small work function. Examples of the cathode material that can be used include metal elements such as lithium, sodium, potassium, cesium, calcium, magnesium, aluminum, indium, silver, lead, tin, and chromium, and a plurality of alloys thereof. A metal oxide such as indium tin oxide (ITO) can also be used. In addition, a cathode may have a single layer constitution or a multilayer constitution.

The substrate used in the organic light-emitting device of the present invention is not particularly limited, but an opaque substrate such as a metal substrate, and a ceramic substrate or a transparent substrate such as glass, quartz, and a plastic sheet can be used. In addition, a color filter film, a fluorescent color conversion filter film, a dielectric reflection film and the like can be used for the substrate to control the emitted light.

Incidentally, the produced organic light-emitting device may be provided with a protective layer or an encapsulating layer for the purpose of preventing the device from contacting oxygen or moisture, and the like, for example. Examples of the protective layer include a diamond thin film, an inorganic material film made of, for example, a metal oxide or a metal nitride, a polymer film such as fluororesin, polyparaxylene, polyethylene, silicone resin, or polystyrene resin, and a photocurable resin and the like. In addition, the device may be covered with glass, a gas impermeable film, a metal, or the like, and the device itself can be packaged with an appropriate encapsulating resin.

The organic compound layer containing the fused polycyclic compound of the present invention can be produced by, for example, a vacuum evaporation method, a casting method, an applying method, a spin coating method, or an ink-jet method.

The organic light-emitting device of the present invention is applicable to a product which requires energy conservation and high luminance. As application examples, a display apparatus, an illumination apparatus, a light source of a printer, a backlight of a liquid crystal display apparatus, and the like are conceivable. As the display apparatus, an energy-saving, light-weight flat panel display with high visibility can be produced. Furthermore, as the light source of a printer, a laser light source portion of a laser beam printer that has been currently used widely can be replaced by the light-emitting device of the present invention. By disposing a device that can be addressed independently on an array and by conducting desired light exposure to a photosensitive drum, an image is formed. The volume of an apparatus can be reduced remarkably by using the organic light-emitting device of the present invention. Regarding the illumination apparatus and the backlight, the effect of saving energy brought about by the present invention can be expected.

The organic light-emitting device of the present invention may be used as a simple matrix type organic light-emitting device. In the case where the device is applied to a display, a TFT driving circuit driven by the active matrix system may be used to drive the device.

EXAMPLES

Hereinafter, the present invention is described specifically by way of examples. However, the present invention is not limited to those examples.

Example 1

Synthesis of Exemplified Compound AE-41

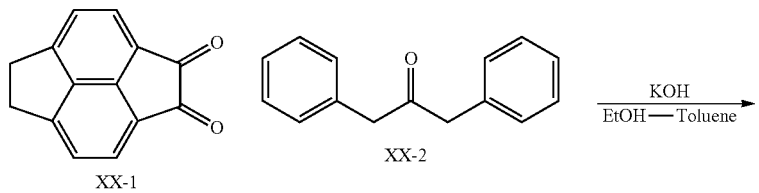

-continued
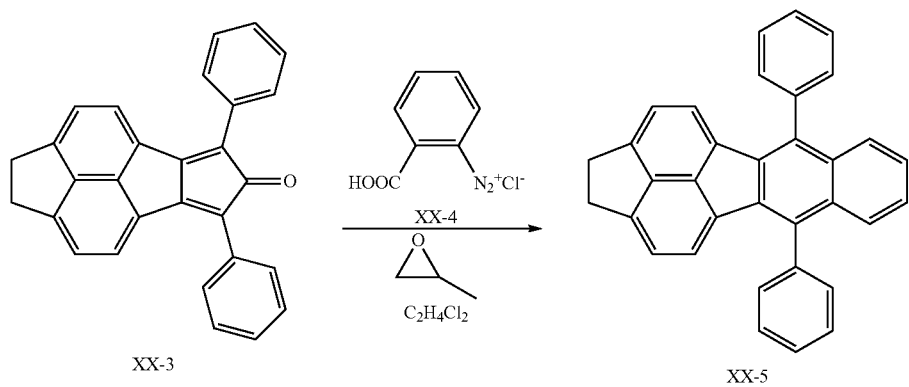
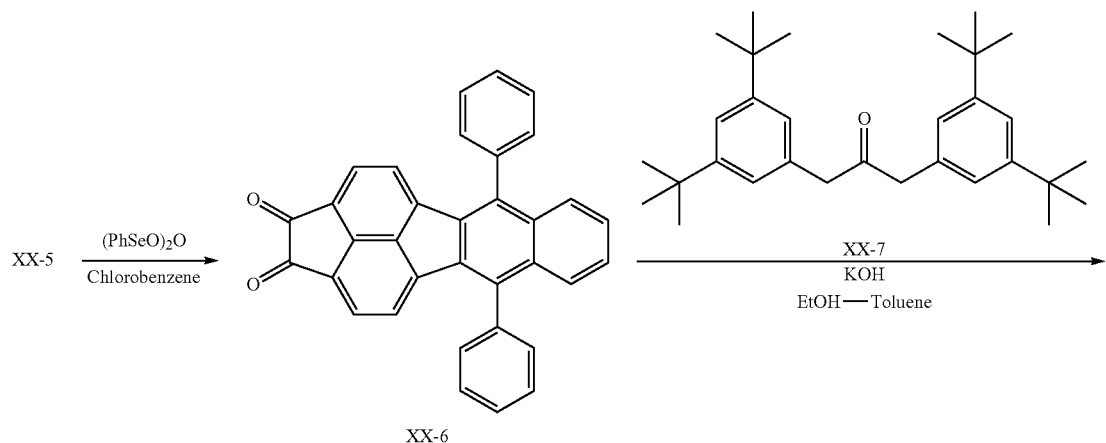
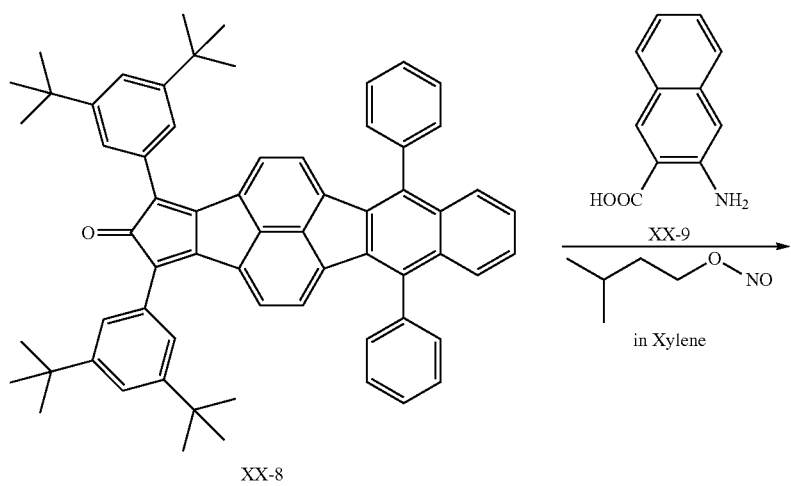

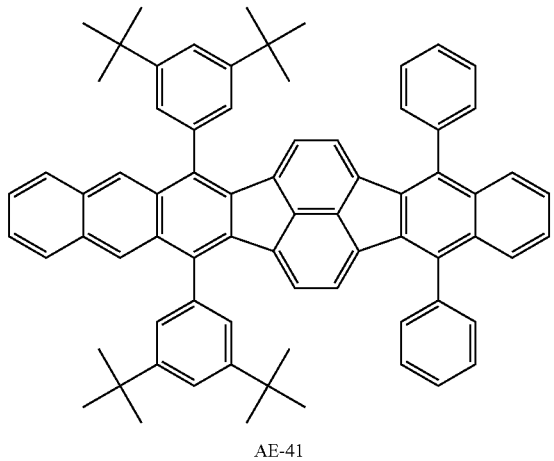

AE-41

(1) Reagents and solvents described below were placed in a 20 mL reaction vessel. Note that XX-1 is a compound synthesized according to Journal of American Chemical Society, 91, 918 (1969).
XX-1: 0.5 g (2.4 mmol)
XX-2: 0.5 g (2.4 mmol)
Toluene/ethanol mixed solvent (toluene:ethanol=1:10 (weight ratio)): 8 mL Next, 1 mL of 6N aqueous solution of potassium hydroxide was slowly added dropwise while the reaction solution was stirred. Subsequently, the reaction solution was heated to 75° C. and stirred at the temperature for 10 minutes. Then, the reaction solution was cooled to room temperature, and the precipitated crystal was filtrated. Thereafter, the crystal was sequentially washed with water and methanol, whereby 0.8 g of XX-3 (yield 86%) was obtained.

(2) Reagents and solvents described below were placed in a 50 mL reaction vessel.
XX-3: 0.8 g (2.1 mmol)
XX-4: 0.4 g (2.3 mmol)
Propylene oxide (0.5 g, 8.3 mmol)
Dichloroethane: 16 mL Next, the reaction solution was heated to 70° C. and stirred at the temperature for 1 hour. After completion of the reaction, the reaction solution was concentrated under reduced pressure, and the concentrate was separated and purified by silica gel chromatography (mobile phase: chloroform/hexane=1/2). The resultant was recrystallized from a chloroform/ethanol mixed solvent, whereby 0.7 g of XX-5 (1.56 mmol, yield 75%) was obtained as a yellow powder.

(3) Reagents and solvents described below were placed in a 300 mL reaction vessel.
XX-5: 3.0 g (6.97 mmol)
Chlorobenzene: 150 mL Next, 7.15 g (13.9 mmol) of benzeneboronic anhydride (70%) was added thereto, and the reaction solution was heated to 130° C. and stirred at the temperature for 24 hours. After completion of the reaction, the reaction solution was concentrated under reduced pressure, and the concentrate was separated and purified by silica gel chromatography (mobile phase: chloroform/hexane=1/1), whereby 3.0 g of XX-6 (6.55 mmol, yield 93%) were obtained as a yellow powder.

(4) Reagents and solvents described below were placed in a reaction vessel.
XX-6: 3.0 g (6.55 mmol)
XX-7: 2.7 g (6.55 mmol)
Toluene/ethanol mixed solvent (toluene:ethanol=1:10 (weight ratio)): 15 mL Next, 1 mL of 6N aqueous solution of potassium hydroxide was slowly added dropwise while the reaction solution was stirred. Subsequently, the reaction solution was heated to 75° C. and stirred at the temperature for 10 minutes. Then, the reaction solution was cooled to room temperature, and the precipitated crystal was filtrated. Thereafter, the crystal was sequentially washed with water and methanol, whereby 4.6 g of XX-8 (yield 82%) were obtained.

(5) Reagents and solvents described below were placed in a 50 mL reaction vessel.
XX-8: 857 mg (1 mmol)
XX-9: 224 mg (0.12 mmol)
Isoamyl nitrite (0.5 g, 8.3 mmol)
Xylene: 20 mL Next, the reaction solution was heated to 110° C. and stirred at the temperature for 1 hour. Next, the reaction solution was concentrated under reduced pressure, and the concentrate was separated and purified by silica gel chromatography (mobile phase: chloroform/hexane=1/3). The resultant was recrystallized from a xylene/ethanol mixed solvent, whereby 513 mg of AE-41 (0.54 mmol, yield 54%) was obtained as a yellow powder.

The structure of the compound was determined by mass spectrometry (MS) measurement and nuclear magnetic resonance spectrometry (NMR) measurement.

To be specific, 954 as M+ of the compound was confirmed by Matrix Assisted Laser Desorption/Ionization Mass Spectrometry (MALDI-MS) measurement. The measurement results by the nuclear magnetic resonance spectrometry are shown below.

$^1$H-NMR(CDCl$_3$, 500 MHz) σ(ppm): 8.12 (s, 2H), 7.78 (m, 2H), 7.62 (m, 8H), 7.54 (m, 6H), 7.43 (d, 4H), 7.35 (m, 2H), 7.32 (m, 2H), 6.32 (d, 2H), 6.26 (d, 2H), 1.40 (s, 36H).

Example 2

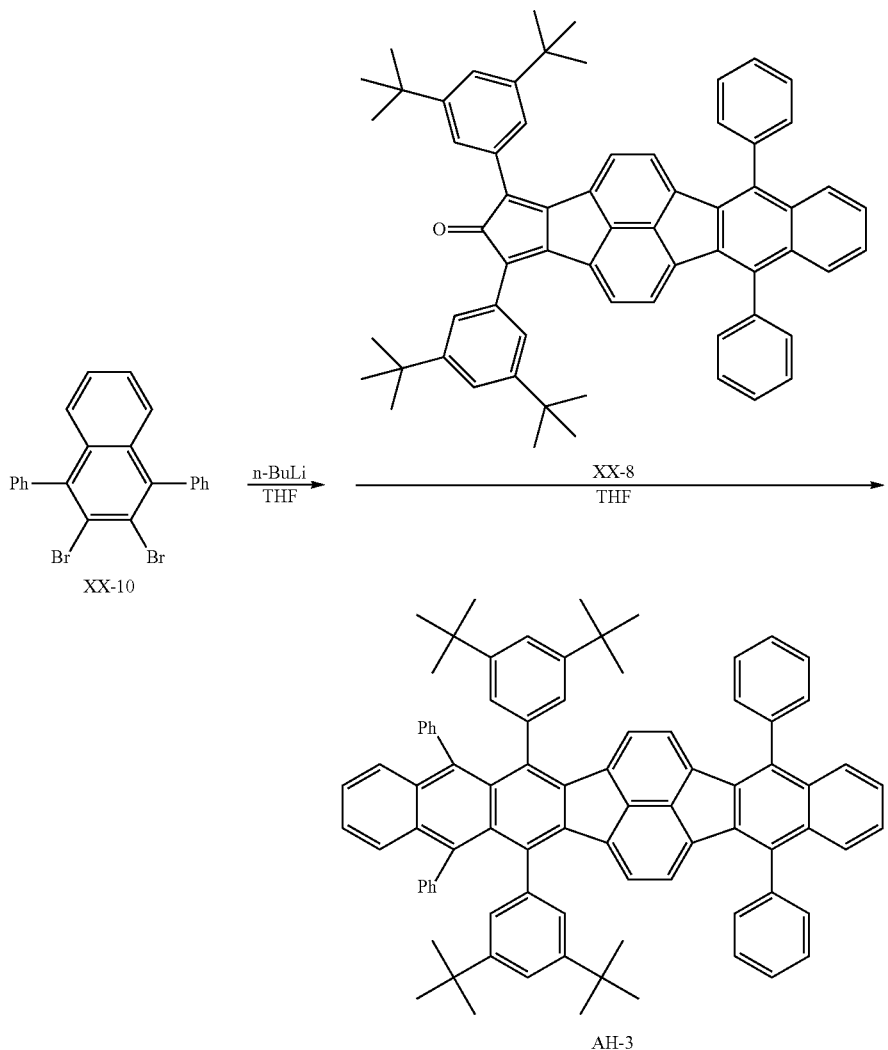

Reagents and solvents described below were placed in a 50 mL reaction vessel, and the internal atmosphere of the reaction vessel was replaced with nitrogen. Note that XX-10 is a compound synthesized according to Journal of Organic Chemistry, 55, 4190 (1990).
XX-10: 876 mg (2 mmol)
Anhydrous THF: 5 mL Next, the reaction solution was cooled to −78° C., and a solution of n-butyllithium hexane (1.6 M, 1.25 mL, 2 mmol) was added thereto. Then, the reaction solution was stirred at −78° C. for 30 minutes. Thereafter, XX-8 (857 mg, 1 mmol) was added to the reaction solution, and the reaction solution was heated to room temperature and stirred at room temperature for 12 hours. Next, the reaction solution was concentrated under reduced pressure, and the concentrate was separated and purified by silica gel chromatography (mobile phase: toluene/hexane=1/3). The resultant was recrystallized from a xylene/ethanol mixed solvent, whereby 450 mg (0.41 mmol, yield 41%) of AH-3 was obtained as a yellow powder.

The structure of the compound was determined by mass spectrometry (MS) measurement and nuclear magnetic resonance spectrometry (NMR) measurement.

To be specific, 1106 as M+ of the compound was confirmed by Matrix Assisted Laser Desorption/Ionization Mass Spectrometry (MALDI-MS) measurement. The measurement results by the nuclear magnetic resonance spectrometry are shown below.

$^1$H-NMR(CDCl$_3$, 500 MHz) σ(ppm): 7.55 (m, 8H), 7.46 (m, 4H), 7.29 (m, 2H), 7.22 (m, 2H), 7.15 (d, 4H), 7.02 (m, 10H), 6.79 (d, 2H), 6.01 (d, 2H), 5.46 (d, 2H), 1.22 (s, 36H).

Example 3

An organic light-emitting device having the configuration illustrated in FIG. 4 was produced by the following method.

First, film formation was performed using indium tin oxide (ITO) on a glass substrate (substrate 1) by sputtering, whereby an anode 2 was formed. In this case, the anode 2 had a thickness of 120 nm. Next, the substrate was ultrasonically cleaned sequentially with acetone and isopropyl alcohol (IPA), and the substrate was washed with boiled IPA and dried. Then, the substrate was cleaned with UV/ozone. The thus-processed substrate was used as a transparent conductive support substrate.

Next, film formation was performed using a 0.1 wt % solution of HTL-1 (shown below) in chloroform on the transparent conductive support substrate by a spin coating method, whereby a hole transport layer 5 was formed. In this case, the hole transport layer had a thickness of 11 nm.

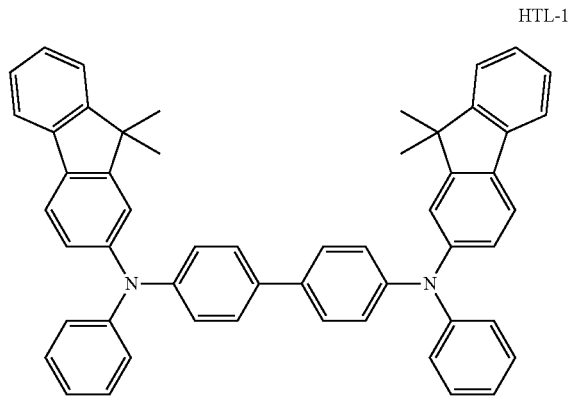

HTL-1

Next, continuous film formation was performed using other organic compound layers and an electrode layer by vacuum evaporation based on resistive heating in a vacuum chamber where the inner pressure was set to $10^{-5}$ Pa, whereby an organic light-emitting device was produced.

To be specific, first, coevaporation was performed using the following HOST-1 serving as a host and Exemplified Compound AE-41 serving as a guest on the hole transport layer 5 in such a manner that the weight concentration ratio of HOST-1 to Exemplified Compound AE-41 was 98:2, whereby an emission layer 3 was formed. In this case, the light-emitting layer 3 had a thickness of 30 nm. Next, film formation was performed using ETL-1 shown below on the emission layer 3, whereby an electron transport layer 6 was formed. In this case, the electron transport layer 6 had a thickness of 40 nm. Thereafter, film formation was performed using LiF on the electron transport layer 6, whereby a first metal electrode layer was formed. In this case, the first metal electrode layer had a thickness of 0.5 nm. Finally, film formation was performed using Al on the first metal electrode layer, whereby a second metal electrode layer was formed. In this case, the second metal electrode layer had a thickness of 150 nm. Note that the first metal electrode layer (LiF film) and second metal electrode layer (Al film) function as a cathode 4. Thus, the organic light-emitting device was obtained.

-continued

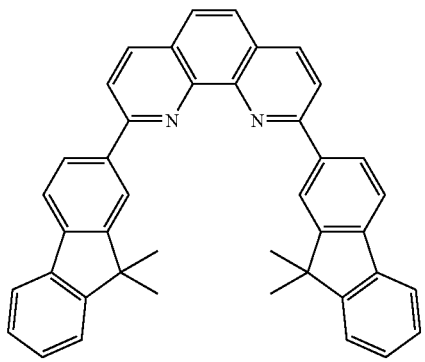

ETL-1

The characteristics of the resulting device were evaluated. As a result, the device of this example was found to have a current efficiency of 19 cd/A in the case of light emission at a luminance of 1,000 cd/m². In addition, continuous energization was performed in the device of this example at a current of 165 mA/cm². As a result, the time it takes for the initial luminance to decrease to its half value was found to be 1,100 hours.

The results reveal that the organic light-emitting device including the fused polycyclic compound of the present invention as a light-emitting material can emit light stably for a long period of time with high efficiency.

Example 4

A device was produced by following the same procedure as in Example 3 with the exception that Exemplified Compound AH-3 was used as a guest of the emission layer 3 instead of Exemplified Compound AE-41.

When a voltage of 6.0 V was applied to the organic light-emitting device of this example, emission of yellow-green light was observed. Moreover, when continuous energization was performed in the device in a nitrogen atmosphere, the device was confirmed to emit light stably even after 100-hours continuous energization.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions. This application claims the benefit of Japanese Patent Application No. 2008-200354, filed on Aug. 4, 2008, which is hereby incorporated by reference herein in its entirety.

The invention claimed is:

1. A fused polycyclic compound represented by the general formula [1]:

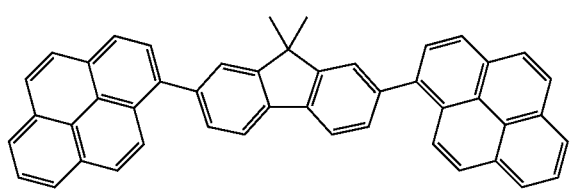

HOST-1

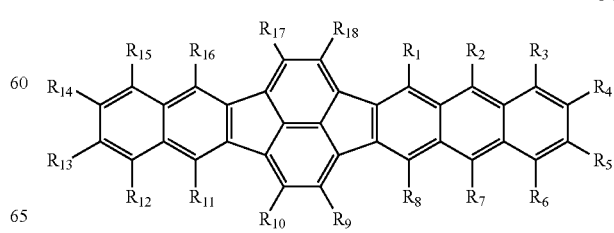

[1]

wherein $R_1, R_2, R_3, R_4, R_5, R_6, R_7, R_8, R_9, R_{10}, R_{11}, R_{12}, R_{13}, R_{14}, R_{15}, R_{16}, R_{17}$, and $R_{18}$ each represent, independently of one another, a hydrogen atom, a halogen atom, an alkyl group having 1 to 20 carbon atoms, a substituted amino group, a substituted or unsubstituted aryl group, or a substituted or unsubstituted heterocyclic group, provided that at least one of $R_1, R_2, R_3, R_4, R_5, R_6, R_7, R_8, R_9, R_{10}, R_{11}, R_{12}, R_{13}, R_{14}, R_{15}, R_{16}, R_{17}$, and $R_{18}$ is a substituted phenyl group represented by the general formula [2]:

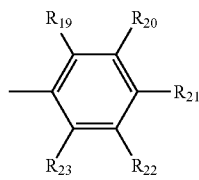

[2]

wherein $R_{19}, R_{20}, R_{21}, R_{22}$, and $R_{23}$ each represent, independently of one another, a hydrogen atom, a halogen atom, an alkyl group having 1 to 20 carbon atoms, a substituted amino group, a substituted or unsubstituted aryl group, or a substituted or unsubstituted heterocyclic group, provided that at least one of $R_{19}, R_{20}, R_{22}$, and $R_{23}$ is a halogen atom, an alkyl group having 1 to 20 carbon atoms, a substituted amino group, a substituted or unsubstituted aryl group, or a substituted or unsubstituted heterocyclic group.

2. The fused polycyclic compound according to claim 1, wherein at least one of $R_1, R_8, R_{11}$, and $R_{16}$ is the substituted phenyl group.

3. The fused polycyclic compound according to claim 1, wherein $R_1, R_8, R_{11}$, and $R_{16}$ are substituted or unsubstituted aryl groups.

4. An organic light-emitting device, comprising:
an anode;
a cathode; and
organic compound layers interposed between the anode and the cathode,
wherein at least one of the organic compound layers contains the fused polycyclic compound set forth in claim 1.

5. The organic light-emitting device according to claim 4, wherein the fused polycyclic compound is contained in a light-emitting layer.

6. The organic light-emitting device according to claim 5, wherein the light-emitting layer is formed of a host and a guest.

7. The organic light-emitting device according to claim 6, wherein the guest comprises the fused polycyclic compound.

8. The organic light-emitting device according to claim 4, which emits light by applying a voltage between the anode and the cathode.

* * * * *